(12) United States Patent
Mehta

(10) Patent No.: US 12,266,439 B2
(45) Date of Patent: Apr. 1, 2025

(54) THERAPEUTIC INTERVENTION METHODS, DEVICES, AND SYSTEMS

(71) Applicant: THE REGENTS OF THE UNIVERSITY OF CALIFORNIA, Oakland, CA (US)

(72) Inventor: Ravindra Mehta, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1508 days.

(21) Appl. No.: 16/485,103

(22) PCT Filed: Feb. 9, 2018

(86) PCT No.: PCT/US2018/017675
§ 371 (c)(1),
(2) Date: Aug. 9, 2019

(87) PCT Pub. No.: WO2018/148581
PCT Pub. Date: Aug. 16, 2018

(65) Prior Publication Data
US 2020/0043592 A1 Feb. 6, 2020

Related U.S. Application Data

(60) Provisional application No. 62/457,688, filed on Feb. 10, 2017.

(51) Int. Cl.
*G16H 20/40* (2018.01)
*A61M 1/16* (2006.01)
(Continued)

(52) U.S. Cl.
CPC .......... *G16H 20/40* (2018.01); *A61M 1/1603* (2014.02); *A61M 1/3403* (2014.02);
(Continued)

(58) Field of Classification Search
CPC ........ G16H 20/40; G16H 20/00; G16H 15/00; G16H 40/63; G16H 50/20; G16H 50/30;
(Continued)

(56) References Cited

U.S. PATENT DOCUMENTS

2003/0083585 A1* 5/2003 Oort .................. A61B 5/352
600/510
2006/0271407 A1* 11/2006 Rosenfeld ............ G16H 50/20
434/262
(Continued)

FOREIGN PATENT DOCUMENTS

WO 2015/136502 A1 9/2015
WO 2018/148581 A1 8/2018

OTHER PUBLICATIONS

Baldwin et al., "Role of Technology for the Management of AKI in Critically Ill Patients: From Adoptive Technology to Precision Continuous Renal Replacement Therapy", Aug. 26, 2016, ADQI Consensus, Blood Purif 2016;42:248-265. (Year: 2016).*

(Continued)

*Primary Examiner* — Mohamed Charioui
(74) *Attorney, Agent, or Firm* — Perkins Coie LLP

(57) ABSTRACT

Described herein are devices, systems, and methods used to assess an organ or organ system and determine a course of treatment for said organ, organ system, and/or patient.

21 Claims, 34 Drawing Sheets

(51) Int. Cl.

| | |
|---|---|
| *A61M 1/34* | (2006.01) |
| *A61M 1/36* | (2006.01) |
| *A61M 16/00* | (2006.01) |
| *A61M 60/139* | (2021.01) |
| *A61M 60/148* | (2021.01) |
| *A61M 60/178* | (2021.01) |
| *A61M 60/216* | (2021.01) |
| *A61M 60/295* | (2021.01) |
| *A61M 60/515* | (2021.01) |
| *A61M 60/531* | (2021.01) |
| *G16H 15/00* | (2018.01) |

(52) U.S. Cl.
CPC ........ *A61M 1/3689* (2014.02); *A61M 16/024* (2017.08); *A61M 60/139* (2021.01); *A61M 60/148* (2021.01); *A61M 60/178* (2021.01); *A61M 60/216* (2021.01); *A61M 60/295* (2021.01); *A61M 60/515* (2021.01); *A61M 60/531* (2021.01); *G16H 15/00* (2018.01); *A61M 1/1698* (2013.01); *A61M 2210/0693* (2013.01); *A61M 2210/1071* (2013.01); *A61M 2210/1082* (2013.01); *A61M 2210/125* (2013.01); *A61M 2230/04* (2013.01); *A61M 2230/208* (2013.01)

(58) Field of Classification Search
CPC .... A61M 1/1603; A61M 1/00; A61M 1/3403; A61M 1/3689; A61M 16/024; A61M 16/00; A61M 60/139; A61M 60/148; A61M 60/178; A61M 60/216; A61M 60/295; A61M 60/515; A61M 60/00; A61M 60/531; A61M 1/1698; A61M 2210/0693; A61M 2210/1071; A61M 2210/00; A61M 2210/1082; A61M 2210/125; A61M 2230/04; A61M 2230/00; A61M 2230/208; A61M 1/14; A61N 1/39
See application file for complete search history.

(56) References Cited

U.S. PATENT DOCUMENTS

| | | | |
|---|---|---|---|
| 2011/0053869 A1 | 3/2011 | Foker | |
| 2011/0270331 A1 | 11/2011 | Peters et al. | |
| 2012/0286157 A1 | 11/2012 | Fuhrmann et al. | |
| 2015/0023981 A1* | 1/2015 | De Kretser | C07K 16/22 514/44 R |

OTHER PUBLICATIONS

Ostermann et al., "Patient Selection and Timing of Continuous Renal Replacement Therapy", Aug. 26, 2016, ADQI Consensus, Blood Purif 2016;42:224-237. (Year: 2016).*
Grissom et al., "A Modified Sequential Organ Failure Assessment Score for Critical Care Triage", 2010, Cambridge University Press, pp. 277-284. (Year: 2010).*
Sffle et al., "Multiple organ failure in patients with thermal injury : Critical Care Medicine", 1993, Department of Surgery and the Intermountain Burn Center, University of Utah Health Science Center, Salt Lake City, UT. pp. 1-10. (Year: 1993).*
Office Action, dated Mar. 1, 2022 for Indian Patent Application No. 201917035344 (original and translation enclosed).
Extended European Search Report, dated Nov. 10, 2020, for European Patent Application No. 18751763.6.
International Search Report and Written Opinion, mailed Jul. 6, 2018, for International Application No. PCT/US2018/017675.
Canadian Examination Report for Canadian Patent Application No. 3,052,969, dated Nov. 21, 2023, 4 pages.
Alsous, Fadi , "Negative Fluid Balance Predicts Survival in Patients With Septic Shock", A retrospective pilot study. Chest 117: 1749-1754, Jul. 2000, 6 pp.
Bagshaw, S , "Survival following adult cardiac arrest in intensive care units: a 5-year retrospective analysis", Crit Care 14(Suppl 1):P324, 2010, 2 pp.
Bagshaw, Sean M., "A proposed algorithm for initiation of renal replacement therapy in adult critically ill patients", Crit Care 13: 317, Nov. 11, 2009, 8 pp.
Bagshaw, Sean M., "Early diagnosis of acute kidney injury", Curr Opin Crit Care 13: 638-644, 2007, 7 pp.
Bagshaw, Sean M., "Epidemiology of renal recovery after acute renal failure", Curr Opin Crit Care 12: 544-550, 2006, 7 pp.
Bagshaw, Sean M., "Review article: Renal Support in critical illness", Can J Anaesth 57: 999-1013, Oct. 8, 2010, 15 pp.
Bagshaw, Sean M., "Urinary biomarkers in septic acute kidney injury", Intensive care medicine 33, 1285-1296, May 9, 2007, 12 pp.
Bagshaw, Sean M., "When to start renal replacement hterapy in critically ill patients with acute kidney injury: comment on AKIKI and ELAIN", Critical care (London, England), Aug. 6, 2016, 3 pp.
Barbar, Saber Davide, "Impact on mortality of the timing of renal replacement therapy in patients with severe acute kidney injury in septic shock: the IDEAL-ICU study (initiation of dialysis early versus delayed in the intensive care unit): study protocol for a randomized", controlled trial; Trials 15, 270, Jul. 7, 2014, 10 pp.
Baumann, Terry J., "Minimum urine collection periods for accurate determination of creatinine clearance in critically ill patients", Clin Pharm. May 1987;6(5):393-8, May 1987, 6 pp.
Bell, Max , "Optimal follow-up time after continuous renal replacement therapy in actual renal failure patients stratified with the Rifle criteria", Nephrol Dial Transplant 20: 354-360, Dec. 14, 2004, 7 pp.
Bellomo, Rinaldo , "Blood Purification in the Intensive Care Unit: Evolving Concepts", World J Surgery 2001, 25: 677-683, Apr. 12, 2001, 7 pp.
Bellomo, Rinaldo , "Intensity of Continuous Renal-Replacement Therapy in Critically Ill Patients", N Engl J Med 361, 1627-1638, Oct. 22, 2009, 12 pp.
Bent, Paul , "Early and Intensive Continuous Hemofiltration for Severe Renal Failure After Cardiac Surgery", Ann Thorac Surg. 71(3):832-7., 2001, 6 pp.
Bouchard, Josee , "A Prospective International Multicenter Study of AKI in the Intensive Care Unit", Clin J Am Soc Nephrol, doi:10. 2215/CJN.04360514, Jul. 20, 2015, 19 pp.
Bouchard, Josee , "Comparison of methods for estimating glomerular filtration rate in critically ill patients with acute kidney injury", Nephrol Dial Transplant 25, 102-107, doi:10.1093/ndt/gfp392, Aug. 13, 2009, 6 pp.
Bouchard, Josee , "Fluid accumulation and acute kidney injury: consequence or cause", Curr Opin Crit Care 15: 509-513, 2009, 5 pp.
Bouchard, Josee , "Fluid accumulation, survival and recovery of kidney function in critically ill patients with acute kidney injury", Kidney Int 76: 422-427, May 13, 2009, 6 pp.
Bouman, Catherine S. C., "Effects of early high-volume continuous venovenous hemofiltration on survival and recovery of renal function in intensive care patients with acute renal failure: A prospective, randomized trial", Crit Care Med 30, 2205-2211, 2002, 7 pp.
Bouman, Catherine S. C., "Timing of renal replacement therapy in critically ill patients with acute kidney injury", Curr Opinion in Critical Care, 2007, 6 pp.
Cantarovich, Felix , "High-Dose Furosemide for Established ARF: A Prospective, Randomized, Double-Blind, Placebo-Controlled, Multicenter Trial", American Journal of Kidney Diseases, vol. 44, No. 3: pp. 402-409, Sep. 2004, 8 pp.
Cerda, Jorge , "Fluid Overload in Critically Ill Patients with Acute Kidney Injury", Blood Purif 29: 331-338, Feb. 19, 2010, 8 pp.
Cherry, Robert A., "Accuracy of Short-Duration Creatinine Clearance Determinations in Predicting 24-Hour Creatinine Clearance in Critically Ill and Injured Patients", J Trauma; 53:267-271., 2002, 5 pp.
Chertow, Glenn M., "Early to Dialyze Healthy and Wise?", JAMA, 315(20):21712172., May 2016, 2 pp.

(56) References Cited

OTHER PUBLICATIONS

Chou, Yu-Hsiang, "Impact of timing of renal replacement therapy initiation on outcome of septic acute kidney injury", Crit Care 15: R134, Jun. 6, 2011, 9 pp.

Clark, Edward, "Timing of initiation of renal replacement therapy for acute kidney injury: a survey of nephologists and intensivists in Canada", Nephrol Dial Transplant 27: 2761-2767, Nov. 19, 2011, 7 pp.

Clark, Edward, "Timing the initiation of renal replacement therapy for acute kidney injury in Canadian intensive care units: a multicentre observational study", Can J Anaesth 59: 861-870, Jun. 30, 2012, 10 pp.

Claure-Del Granado, Rolando, "Withholding and Withdrawing Renal Support in Acute Kidney Injury", Semin Dial 24: 208-214, 2011, 7 pp.

Clec'h, Christophe, "Efficacy of renal replacement therapy in critically ill patients: a propensity analysis", Crit Care 16:R236, Dec. 19, 2012, 9 pp.

Clec'h, Christophe, "Multiple-center evaluation of mortality associated with acute kidney injury in critically ill patients: a competing risks analysis", Crit Care 15: R128, May 17, 2011, 9 pp.

Clermont, Gilles, "Renal failure in the ICU: Comparison of the impact of acute renal failure and end-stage renal disease on ICU outcomes", Kidney Int 62: 986-996, Apr. 9, 2002, 11 pp.

Conil, Jean-Marie, "Assessment of renal function in clinical practice at the bedside of burn patients", Br J Clin Pharmaocology 63: 583-594, Dec. 7, 2006, 12 pp.

Consentino, F., "Risk factors influencing survival in ICU acute renal failure", Nephrol Dial Transplant 9(Suppl 4): 179-182, 1994, 1994, 4 pp.

Cruz, Dinna N., "Biomarker Strategies to Predict Need for Renal Replacement Therapy in Acute Kidney Injury", Seminars in Dialysis, In Press, 2011, 8 pp.

Cruz, Dinna N., "Clinical review: RIFLE and AKIN—time for reappraisal", Critical care (London, England) 13, 211, Jun. 25, 2009, 9 pp.

Cruz, Dinna N., "Neutrophil gelatinase-associated lipocalin: A promising biomarker for detecting cardiac surgery-associated acute kidney injury", J Thorac Cardiovasc Surg 139: 1101-1106, Nov. 2, 2009, 6 pp.

Cruz, Dinna N., "Plasma neutrophil gelatinase-associated lipocalin is an early biomarker for acute kidney injury in an adult ICU population", Intensive Care Med 36:444-451, Dec. 3, 2009, 8 pp.

Dermirkilic, Ufuk, "Timing of Replacement Therapy for Acute Renal Failure After Cardiac Surgery", J Card Surg.; 19(1):17-20, 2004, 4 pp.

Durmaz, Isa, "Prophylactic Dialysis in Patients With Renal Dysfunction Undergoing On-Pump Coronary Artery Bypass Surgery", Ann Thoracic Surg.; 75:859-64, Oct. 8, 2002, 6 pp.

Elahi, Maqsood, "Acute kidney injury following cardiac surgery: impact of early versus late haemofiltration on morbidity and mortality", Eur J Cardiothorac Surg 35: 854-863, Feb. 11, 2009, 10 pp.

Elahi, Maqsood M., "Early hemofiltration improves survival in post-cardiotomy patients with acute renal failure", Eur J Cardiothorac Surg.; 26(5): 1027-31, Jul. 23, 2004, 5 pp.

Elseviers, Monique M., "Renal replacement therapy is an independent risk factor for mortality in critically ill patients with acute kidney injury", Crit Care 14: R221, 2010, 9 pp.

Gaudry, Stephane, "Initiation Strategies for Renal-Replacement Therapy in the Intensive Care Unit", N Engl J Med 375, 122-133, Jul. 14, 2016, 12 pp.

Gettings, L.G., "Outcome in post-traumatic acute renal failure when continuous renal replacement therapy is applied early vs. late", Intensive care medicine, 25(8):805-813, May 20, 1999, 9 pp.

Gibney, Noel, "Timing of Initiation and Discontinuation of Renal Replacement Therapy in AKI: Unanswered Key Questions", Clin J Am Soc Nephrol 3: 876-880, Feb. 26, 2008, 5 pp.

Gibney, R.T. Noel, "When Should Renal Replacement Therapy for Acute Kidney Injury be Initiated and Discontinued?", Blood purification 26, 473-484, Sep. 22, 2008, 12 pp.

Granata, Antonio, "Vascular Access for Acute Extracorporeal Renal Replacement Therapies", Contrib Nephrol 142: 159-177, 2004, 19 pp.

Haase, Michael, "Accuracy of Neutrophil Gelatinase-Associated Lipocalin (NGAL) in Diagnosis and Prognosis in Acute Kidney Injury: A Systematic Review and Meta-analysis", Am J Kid Dis;54: 1012-24, Dec. 2009, 13 pp.

Herget-Rosenthal, S., "Serum cystatin C—a superior marker of rapidly reduced glomerular filtration after uninephrectomy in kidney donors compared to creatinine", Clinical nephrology 64, 41-46, Aug. 2005, 7 pp.

Herget-Rosenthal, Stefan, "Predictive Value of Tubular Proteinuria and Enzymuria in Nonoliguric Acute Tubular Necrosis", Clin Chemistry 50:3 552-558, Jan. 6, 2004, 7 pp.

Himmelfarb, Jonathan, "Evaluation and Initial Management of Acute Kidney Injury", Clin J Am Soc Nephrol 3, 962-967, Feb. 4, 2008, 11 pp.

Honore, Patrick M., "Prospective evaluation of short-term, high-volume isovolemic hemofiltration on the hemodynamic course and outcome in patients with intractable circulatory failure resulting from septic shock", Critical Care Medicine;28:3581-3587, 2000, 7 pp.

Hoste, Eric A.J., "Assessment of renal function in recently admitted critically ill patients with normal serum creatinine", Nephrol Dial Transplant 20: 747-753, Feb. 8, 2005, 7 pp.

Imai, Yumiko, "Injurious Mechanical Ventilation and End-Organ Epithelial Cell Apoptosis and Organ Dysfunction in an Experimental Model of Acute Respiratory Distress Syndrome", JAMA vol. 289 No. 16, Apr. 23, 2003, 9 pp.

Karvellas, Constantine J., "A comparison of early versus late initiation of renal replacement therapy in critically ill patients with acute kidney injury: a systematic review and meta-analysis", Crit Care 15: R72, Feb. 25, 2011, 10 pp.

Kellum, John A., "Kidney Attack", JAMA 307: 2265-2266, Jun. 6, 2012, 2 pp.

Kelly, K. J., "Distant Effects of Experiemental Renal Ischemia/Reperfusion Injury", J Am Soc Nephrol 14: 1549-1558, 2003, 10 pp.

Khosla, Nitin, "Preexisting Chronic Kidney Disease: A Potential for Improved Outcomes from Acute Kidney Injury", Clin J Am Soc Nephrol 4, 1914-1919., Sep. 23, 2009, 12 pp.

Khwaja, Arif, "KDIGO Clinical Practice Guidelines for Acute Kidney Injury", Kidney Int Suppl 2: 1-138, Aug. 7, 2012, 6 pp.

Koyner, Jay L., "Urinary cystatin C as an early biomarker of acute kidney injury following adult cardiothoracic surgery", Kidney Int;74(8):1059-69, Jul. 23, 2008, 11 pp.

Lameire, Norbert, "When to start dialysis in patients with acute kidney injury? When semantics and logic become entangled with expectations and beliefs", Crit Care 15: 171, Jul. 8, 2011, 2 pp.

Leite, Tacyanon T., "Timing of renal replacement therapy initiation by AKIN classification system", Crit Care 17: R62, Apr. 2, 2013, 9 pp.

Levy, Elliott M., "The Effect of Acute Renal Failure on Mortality: A Cohort Analysis", JAMA; 275:1489-1494, May 15, 1996, 6 pp.

Liangos, Orfeas, "Relationship of Urine Output to Dialysis Initiation and Mortality in Acute Renal Failure", Nephron Clin Pract; c56-c60, Dec. 30, 2004, 5 pp.

Liano, Fernando, "The specturm of acute renal failure in the intensive care unit compared with that seen in other settings", The Madrid Acute Renal Failure Study Group. Kidney Int Suppl 66: S16-S24, 1998, 10 pp.

Liu, Kathleen D., "Timing of Initiation of Dialysis in Critically Ill Patients with Acute Kidney Injury", Clin J Am Soc Nephrol 2006, 1(5):915-919, May 24, 2006, 5 pp.

Macedo, Etiene, "Fluid accumulation, recognition and staging of acute Kidney injury in critically-ill patients", Crit Care 14: R82, May 6, 2010, 7 pp.

Macedo, Etienne, "Early vs late start of dialysis: it's all about timing", Critical care (London, England) 14, 112, doi:10.1186/cc8199, Feb. 8, 2010, 3 pp.

Macedo, Etienne, "Long-Term Follow-Up of Patients after Acute Kidney Injury: Patterns of Renal Functional Recovery", PLoS One 7: e36388, May 4, 2012, 7 pp.

(56) References Cited

OTHER PUBLICATIONS

Macedo, Etienne, "Timing of Dialysis Initiation in Acute Kidney Injury and Acute-On-Chronic Renal Failure", Semin Dial 26, 675-681, doi:10.1111/sdi.12128, 2013, 7 pp.

Macedo, Etienne, "When Should Renal Replacement Therapy be Initiated for Acute Kidney Injury", Semin Dial 24: 132-137, 2011, 6 pp.

Malhotra, Rakesh, "Development and Validation of a Risk Score for Predicting Acute Kidney Injury in Intensive Care Unit Patients", In. Abstracts Kidney Week Philadelphia SA-OR003; J Am Soc Nephrol 25, 2014, 3 pp.

Mandelbaum, Tal, "Outcome of critically ill patients with acute kidney injury using the Acute Kidney Injury Network criteria", Crit Care Med vol. 39, No. 12, 2011, 6 pp.

Matson, J., "Blood filtration: new opportunities and the implications of systems biology", Critical Care and Resuscitation; 6: 209-17, 2004, 9 pp.

Mehta, Ravindra L., "Acute Kidney Injury Network: report of an initiative to improve outcomes in acute kidney injury", Care. Mar. 1, 2007;11(2):R31, Mar. 1, 2007, 8 pp.

Mehta, Ravindra L., "Current Status of Renal Replacement Therapy for Acute Renal Failure", A survey of US nephrologists. The National Kidney Foundation Council on Dialysis Am J Nephrol, May 5, 1998, 6 pp.

Mehta, Ravindra L., "Diuretics, Mortality, and Nonrecovery of Renal Function in Acute Renal Failure", JAMA 288:2547-2553, Nov. 7, 2002, 7 pp.

Mehta, Ravindra L., "Fluid balance and acute kidney injury: the missing link for predicting adverse outcomes?", Nat Clin Pract Nephrol 5: 10-11, Jan. 2009, 3 pp.

Mehta, Ravindra L., "Indications for Dialysis in the ICU: Renal Replacement vs. Renal Support", Blood Purif 19: 227-232, 2001, 7 pp.

Mehta, Ravindra L., "Nephrology Consultation in Acute Renal Failure: Does Timing Matter?", Am J Med. 113:456-461, Oct. 15, 2002, 6 pp.

Mehta, Ravindra L., "Renal-Replacement Therapy in the Critically Ill—Does Timing Matter?", The New England journal of medicine 375, 175-176, doi:10.1056/NEJMe1606125, Jul. 14, 2016, 2 pp.

Mehta, Ravindra L., "Spectrum of acute renal failure in the intensive care unit: The PICARD experience", Kidney Int 66, 1613-1621, doi:10.1111/j.1523-1755.2004.00927.x KID927 [pii], May 17, 2004, 9 pp.

Metnitz, Philipp G.H., "Effect of acute renal failure requiring renal replacement therapy on outcome in critically ill patients", Crit Care Med. Sep. 2002;30(9):2051-8., 2002, 8 pp.

Mink, S.N., "Early but not delayed continuous arteriovenous hemofiltration improves cardiovascular function in sepsis in dogs", Intensive Care Med. 1999, 25: 733-743, Apr. 23, 1999, 11 pp.

Molitoris, Bruce A., "Technology Insight: biomarker development in acute kidney injury-what can we anticipate?", Nature clinical practice 4, 154-165, Jan. 29, 2008, 12 pp.

Molnar, Miklos Z., "Timing of dialysis initiation in transplant-naive and failed transplant patients", Nat Rev Nephrol 8: 284-292, May 2012, 9 pp.

Ostermann, Marlies, "Correlation between parameters at initiation of renal replacement therapy and outcome in patients with acute kidney injury", Critical Care 2009, 13:R175 (doi:10.1186/cc8154), Nov. 4, 2009, 13 pp.

Ostermann, Marlies, "Renal replacement therapy in critically ill patients with acute kidney injury-when to start", Nephrol Dial Transplant 27: 2242-2248, Jan. 9, 2012, 7 pp.

Overberger, Pamela, "Management of Renal Replacement Therapy in Acute Kidney Injury: A Survey of Practitioner Prescribing Practices", CJASN 2007 2: 623-630, Jul. 2007, 15 pp.

Palevsky, Paul M., "Intensity of renal replacement therapy in acute kidney injury: perspective from within the Acute Renal Failure Trial Network Study", Crit Care.; 13(4): 310., Aug. 11, 2009, 6 pp.

Palevsky, Paul M., "Intensity of Renal Support in Critically Ill Patients with Acute Kidney Injury", N Engl J Med, Jul. 3, 2008, 14 pp.

Palevsky, Paul M., "Renal Replacement Therapy I: Indications and Timing", Crit Care Clin 21: 347-356, May 2005, 11 pp.

Pannu, Neesh, "Renal Replacement Therapy in Patients With Acute Renal Failure", JAMA;299(7):793-805. doi: 10.1001/jama.299.7.793., Feb. 20, 2008, 13 pp.

Payen, Didier, "A positive fluid balance is associated with a worse outcome in patients with acute renal failure", Crit Care 12: R74, Jun. 4, 2008, 7 pp.

Perianayagam, Mary C., "Serum Cystatin C for Prediction of Dialysis Requirement or Death in Acute Kidney Injury: A Comparative Study", Am J Kidney Dis 54:1025-1033, Aug. 7, 2009, 9 pp.

Rabindranath, Kannaiyan S., "Intermittent versus continuous renal replacement therapy for acute renal failure in adults (Review)", Cochrane Database Syst Rev. Jul. 18, 2007;(3):CD003773., 2008, 53 pp.

Ricci, Zaccaria, "Practice patterns in the management of acute renal failure in the critically ill patient: an international survey", Nephrol Dial Transplant.; 21(3):690-6, Dec. 2, 2005, 7 pp.

Ricci, Zaccaria, "The RIFLE classification for acute kidney injury definition", Am J Surg 198: 152-153, 2009, 2 pp.

Ricci, Zaccaria, "Timing, dose and mode of dialysis in acute kidney injury", Curr Opin Crit Care 17: 556-561, 2011, 6 pp.

Sakr, Yasser, "Sepsis and organ system failure are major determinants of post-intensive care unit mortality", J Crit Care 23: 475-483, 2008, 9 pp.

Seabra, Victor F., "Timing of Renal Replacement Therapy Initiation in Acute Renal Failure: A Meta-analysis", Am J Kidney Dis 52, 272-284, Jun. 19, 2008, 13 pp.

Shiao, Chih-Chung, "Late initiation of renal replacement therapy is associated with worse outcomes in acute kidney injury after major abdominal surgery", Critical Care, 13:R171, Oct. 30, 2009, 11 pp.

Singer, Mervyn, "The Third International Consensus Definitions for Sepsis and Septic Shock (Sepsis-3)", JAMA 315, 801-810, doi:10.1001/jama.2016.0287, Feb. 23, 2016, 10 pp.

Stel, Vianda S., "Residual renal function at the start of dialysis and clinical outcomes", Nephrol Dial Transplant (2009) 24: 3175-3182, Jun. 10, 2009, 8 pp.

Sugahara, Souichi, "Early start on continuous hemodialysis therapy improves survival rate in patients with acute renal failure following coronary bypass surgery", Hemodial Int 8: 320-325, 2004, 6 pp.

Sutherland, Scott M., "Fluid Overload and Mortality in Children Receiving Continuous Renal Replacement Therapy: The Prospective Pediatric Continuous Renal Replacement Therapy Registry", Am J Kidney Dis 55: 316-325, Dec. 31, 2009, 10 pp.

Teehan, Geoffrey S., "Update on Dialytic Management of Acute Renal Failure", J Intensive Care Med 18: 130-138, Nov. 22, 2002, 9 pp.

Thakar, Charuhas V, "Timing of dialysis initiation in AKI in ICU: international survey", Crit Care 16: R237, Dec. 19, 2012, 8 pp.

Uchino, Shigehiko, "What Is 'Best' RRT Practice?", Contrib Nephrol 165: 244-250, 2010, 7 pp.

Van Biesen, W., "Relationship between fluid status and its management on acute renal failure (ARF) in intensive care unit (ICU) patients with sepsis: A prospective analysis", J Nephrol 18: 54-60, Dec. 15, 2004, 9 pp.

Van Biesen, Wim, "Defining Acute Renal Failure: RIFLE and Beyond", Clin J Am Soc Nephrol 1: 1314-1319, 2006, 6 pp.

Venkataraman, Ramesh, "Adequacy of Dialysis in Acute Renal Failure", Semin Nephrol 25: 120-124, 2005, 5 pp.

Vincent, J. L., "The SOFA (Sepsis-related Organ Failure Assessment) score to describe organ dysfunction/failure", On behalf of the Working Group on Sepsis-Related Problems of the European Society of Intensive Care Medicine. Intensive care medicine 22, 707-710, Apr. 19, 1996, 4 pp.

Vincent, Jean-Louis, "Use of the SOFA score to assess the incidence of organ dysfunction/failure in intensive care units: Results of a multicenter, prospective study", Working group on "sepsis-related problems" of the European Society of Intensive Care Medicine. Crit Care Med 26, 1793-1800, 1998, 17 pp.

(56) References Cited

OTHER PUBLICATIONS

Vinsonneau, Christophe, "Continuous venovenous haemodiafiltration versus intermittent haemodialysis for acute renal failure in patients with multiple-organ dysfunction syndrome: a multicentre randomised trial", Lancet. Jul. 29, 2006;368(9533):379-85., Jul. 29, 2006, 7 pp.

Waikar, Sushrut S., "Declining Mortality in Patients with Acute Renal Failure, 1988 to 2002", J Am Soc Nephrol 17: 1143-1150, Jan. 15, 2006, 8 pp.

Waikar, Sushrut S., "Imperfect Gold Standards for Kidney Injury Biomarker Evaluation", J Am Soc Nephrol 23: 13-21, 2012, 9 pp.

Wald, Ron, "Chronic Dialysis and Death Among Survivors of Acute Kidney Injury Requiring Dialysis", JAMA 302: 1179-1185, Sep. 16, 2009, 7 pp.

Wald, Ron, "Comparison of standard and accelerated initiation of renal replacement therapy in acute kidney injury", Kidney Int 88, 897-904, doi:10.1038/ki.2015.184, Jul. 8, 2015, 8 pp.

White, Laura E., "Inflammatory Mechanisms of Organ Crosstalk during Ischemic Acute Kidney Injury", Int J Nephrol 2012: 505197, Mar. 10, 2011, 8 pp.

Wiedemann, HP, "Comparison of two fluid-managment strategies in acute lung injury", N Engl J Med 354: 2564-2575, 2006, 1 pp.

Wu, Vin-Cent, "Early Renal Replacement Therapy in Patients with Postoperative Acute Liver Failure Associated with Acute Renal Failure: Effect on Postoperative Outcomes", J Am Coll Surgery 2007, 205: 266-276, Apr. 9, 2007, 11 pp.

Zarbock, A., "Evidence-based renal replacement therapy for acute kidney injury", Minerva Anestesiol 75: 135-139, Mar. 2009, 5 pp.

Zarbock, Alexander, "Effect of Early vs Delayed Initiation of Renal Replacement Therapy on Mortality in Critically Ill Patients With Acute Kidney Injury", The ELAIN Randomized Clinical Trial. JAMA 315, 2190-2199, doi:10.1001/jama.2016.5828, May 22, 2016, 10 pp.

\* cited by examiner

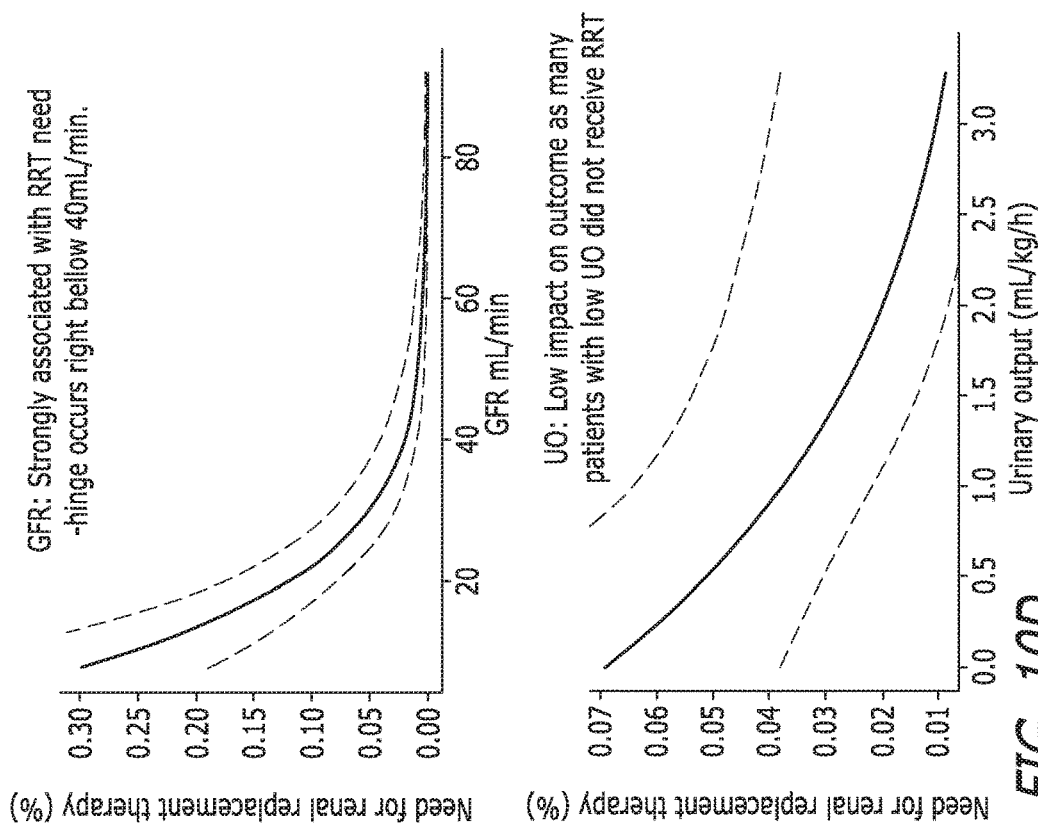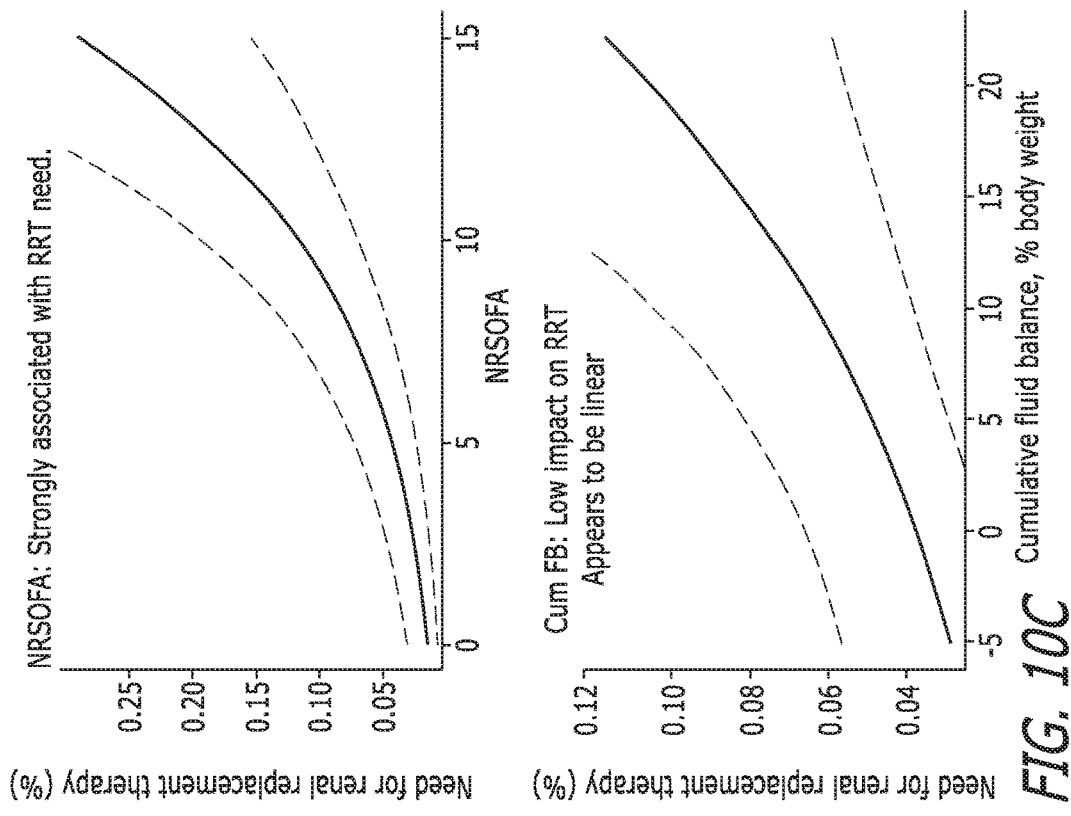

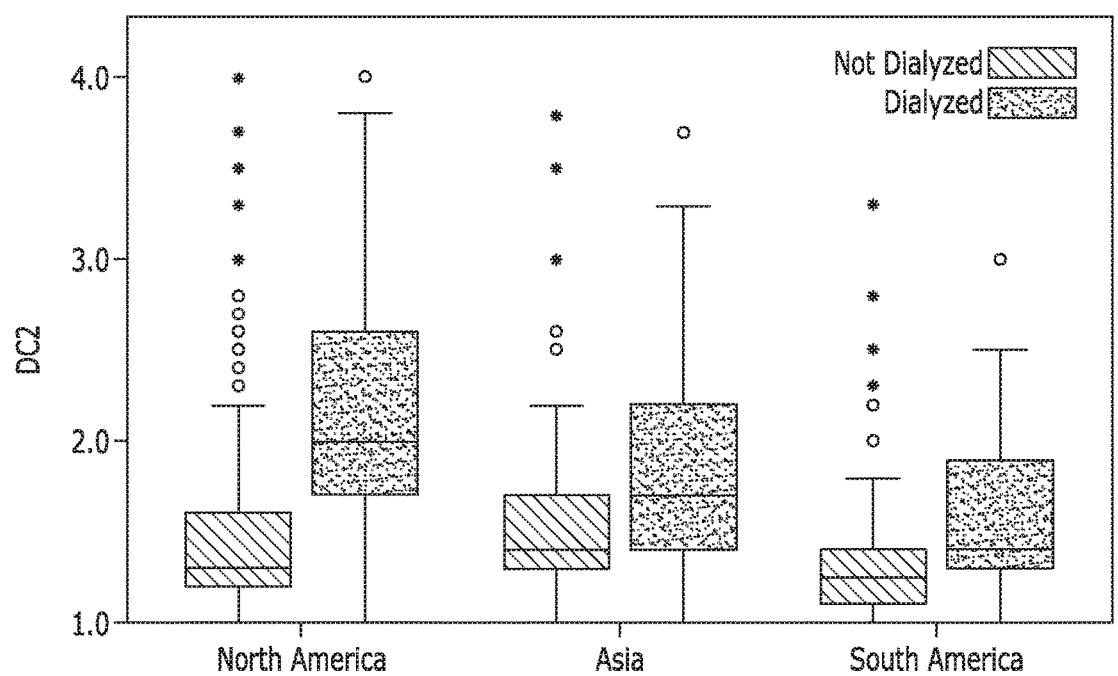
FIG. 15
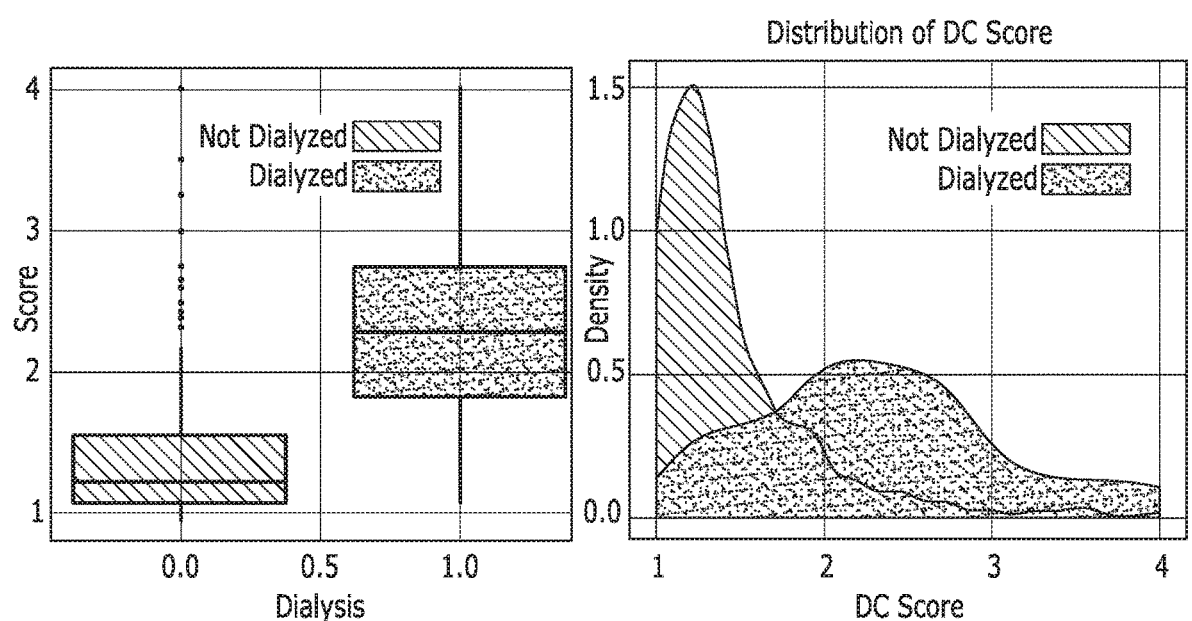
FIG. 16A
FIG. 16B

THERAPEUTIC INTERVENTION METHODS, DEVICES, AND SYSTEMS

PRIORITY CLAIM

This application is a national phase of PCT/US2018/017675, filed on Feb. 9, 2018, which claims priority to U.S. Provisional Patent Application No. 62/457,688, filed on Feb. 10, 2017, the entire disclosure of which are incorporated by reference herein.

FIELD

The present invention pertains to devices and methods for using those devices to assess an organ or organ system and determine a course of treatment for said organ, organ system, and/or patient.

BACKGROUND

Variation in care across physicians, and across care centers, is commonplace. A comprehensive approach for organ or organ system functional assessment and management is lacking. Accordingly, there is a need for a universally applicable system to guide application of individualized organ, or organ system, support care.

SUMMARY

Described herein generally are systems, devices, and methods that can guide application of individualized organ, or organ system, support care. The systems, devices, and methods can assist with timing of organ support based on individualized parameters that are commonly evaluated in a patient care setting.

In some embodiments, the devices, systems, and methods can be for monitoring a subject in need thereof for therapeutic intervention. In some embodiments, this monitoring is dynamic.

Also provided herein are devices, systems, and methods for providing at least one organ system support in a subject in need thereof. Also provided herein are devices, systems, and methods for treating at least one organ system related disease or dysfunction in a subject in need thereof. Also provided herein are devices, systems, and methods for monitoring at least one organ system related disease or dysfunction in a subject in need thereof.

In some embodiments, methods of treatment can include: obtaining a plurality of measurements; determining an organ demand score and an organ capacity score from the plurality of measurements. These scores can be used to calculate a demand:capacity ratio (also referred to herein as D/C or demand/capacity). Such D/C ratios can be calculated by a clinical points ratio calculation, a logistic ratio calculation, a logistic additive ratio calculation, clinical index product ratio calculation, a logistic product ratio calculation, or a combination thereof. In one embodiment, the D/C ratio is calculated by dividing the organ demand score by the organ capacity score to provide the D/C ratio. Based on the calculated D/C ratio a patient can be diagnosed as needing intervention based on the D/C ratio. Finally, organ support can be administered to the diagnosed patient when the D/C ratio is in a target range or terminating organ support to the diagnosed patient when the D/C ratio is above or below the target range.

In some embodiments, the organ system is an integumentary system, a muscular system, a skeletal system, a nervous system, a circulatory system, a lymphatic system, a respiratory system, an endocrine system, a urinary system, a reproductive system, a digestive system, or a combination thereof. In some embodiments, the organ system is an organ. In some embodiments, the organ is a muscle (e.g., skeletal muscle) a stomach, an intestine (e.g., small intestine, large intestine), a kidney, a bladder, a liver, a heart, a lung, a diaphragm, or a combination thereof.

In some embodiments, the organ is a kidney, a heart, a lung, a liver, or a combination thereof. In some embodiments, the organ system related disease is acute kidney injury.

BRIEF DESCRIPTION OF THE DRAWINGS

Embodiments of the present description are illustrated by way of example, and not by way of limitation, in the figures of the accompanying drawings and in which like reference numerals refer to similar elements, wherein:

FIG. 10A-D illustrate D/C parameters are associated with RRT requirement (Cohort 3)

FIG. 15 illustrates D/C at dialysis initiation or day of peak serum creatinine by region (Cohort 2).

FIG. 16A-B illustrates distribution of D/C ratios on day of dialysis or peak serum creatinine. Left panel shows the median and IQR (25-75) values and the right panel shows the distribution in non-dialyzed and dialyzed patients (Cohort 3)

FIG. 17A shows the median and IQR (25-75) values and FIG. 17B shows the distribution in non-dialyzed and dialyzed patients (Cohort 4).

DETAILED DESCRIPTION

Described herein generally are systems and devices to guide application of individualized organ, or organ system, support care. Methods of administering this individualized organ, or organ system, support care are also described.

Multiple organ dysfunction syndrome (MODS) is a common complication in critically ill patients. MODS is characterized by the development of progressive dysfunction in two or more organs or organ systems. The impact of an organ dysfunction can vary from mild clinical alterations in physiological parameters to the necessity for sophisticated equipment to support and temporarily replace organ function. Organ specific support has continued to evolve and clinicians now have a wide array of equipment and techniques for individual organs, e.g., left and right ventricular assist devices (VAD, LVAD, RVAD) and total heart devices for heart failure; extracorporeal membrane oxygenators (ECMO) and $CO_2$ removal (ECCOR) devices for supporting lung function; albumin based dialysis (MARS) for liver support; continuous (CRRT) and intermittent (IHD) dialysis for kidney failure and apheresis techniques to optimize immune function. It is common that these devices are used in combination and are applied at different time points and adjusted individually to meet goals of therapy.

Decisions about when to initiate these techniques and when to modify and discontinue organ support is usually based on clinical criteria and is determined by specialist teams that manage each specific device, e.g., cardiologists for the ventricular assist devices, nephrologist for dialysis. In order to deliver effective use of organ support, specialist teams require support from trained personnel, access to equipment, resources and effective communication among care providers. Therefore, establishing clear goals of care and defining appropriate timing of intervention for each organ support is essential for optimal patient management.

Figure 1:
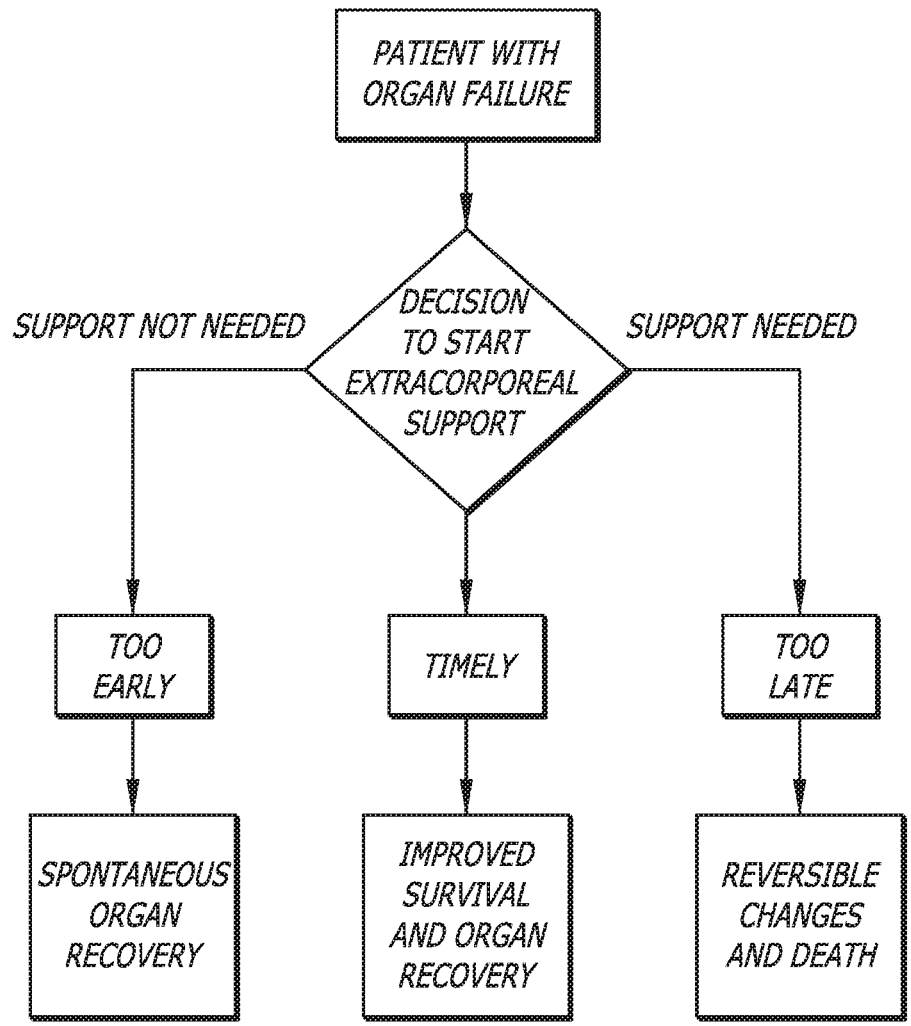
FIG. 1 illustrates a flow chart representation of the organ support dilemma.

Clinicians deciding when organ support is needed generally require a balancing of potential benefits with risks associated with support (FIG. 1). If support is started too early there is a concern that patients may not need the support, and organ or organ system improvement with conservative management may have otherwise occurred. Inherent risks associated with organ support need to be considered as the complexity of the procedures and the overall clinical condition of the patient increase the frequency of complications.

In some instances, for any dialysis procedure there is risk for placement of catheters to access the circulation and hypotension related to the dialysis complications.

On the other hand, if the support is offered too late, patient benefit from the procedure may decrease and the likelihood of irreversible organ or organ system failure increases. Thus, defining an optimal timing to initiate therapy is subject to variation and depends on how well the physician perceives patient need for organ or organ system support, most often based on the trends in the patient physiologic and lab parameters. Because of a lack of clear parameters to define timing intervention and a high risk of complication, most physicians tend to adopt a wait to see approach if not facing a life-threatening situation. Often this results in a delay in initiating therapy and may contribute to a lack of benefit, as it may be too late to improve organ or organ system function. The uncertainty of physician decisions is also influenced by the time available to consider the multiple data points of vital signs, lab studies and medications for each patient. This is particularly important in critically ill patients who have dynamic changes in organ or organ system function and require frequent assessments and interventions.

Electronic medical records can provide an ability to trend vital signs, lab studies and track medication use, which can improve data presentation and communication amongst caregivers. However, sheer data volume and the dynamic nature of critical illness add complexity to the timeliness of decision-making. The information overload, particularly for busy physicians, often makes it difficult to process all the data points, considering multiple points of data are derived from different sources. This is further influenced by which caregiver team is responsible for the extracorporeal support technique.

For instance, the cardiology and cardiac surgery team may provide the Intra-aortic balloon pump or LVAD for optimizing heart function, whereas dialysis is provided by the nephrology team. Each group may only focus on their particular organ dysfunction often resulting in distinctive approaches for timing of interventions. Additionally, there is increasing concern that a very high cost of care attributed to high overhead expenses (trained personnel and equipment); increased resource utilization (labs, pharmacy, imaging) and increased demand on services, may not be beneficial.

Variations in care delivery are recognized as an important factor contributing to high resource utilization and several approaches to standardize care delivery have been shown to improve patient care, reduce resource utilization, and improve patient outcomes. Several prospective randomized controlled studies have demonstrated that protocol-based strategies can reduce variation and cost of intensive care unit (ICU) medicine and improve morbidity and mortality in hospitalized patients. The availability of consensus guidelines has provided a tool for physicians to standardize care. However, acceptance of these guidelines and their applications across individual physicians and in different hospitals is highly variable.

A limitation of consensus guidelines is that they are based on population based metrics and may not reflect an individual patient's condition. The general guidelines require individualization but often contribute to variations, as they need to be adjusted. Individual physician choices and preferences are also influenced by local prevailing practices and available resources and contribute to the variations in care delivery. Consequently, variations in care across physicians and across centers are commonplace, particularly in situations where there is no consensus. In this context, access to a clinical decision support system has been shown to be of value for specific interventions. However, a comprehensive approach for organ functional assessment and management is still lacking. There is a great need for a universally applicable system to guide application for organ support for individualized care.

Approaches are described herein that can quantify factors that define the need for organ support in patients, e.g., critically-ill patients. This quantification can be by the devices, systems, and methods described.

At any given time, need for organ support depends on a balance between overall demand and the organ functional capacity. This balance is termed herein as a ratio of demand to capacity or D/C ratio. In some embodiments, the D/C ratio can be calculated by a clinical points ratio calculation, a logistic ratio calculation, a logistic additive ratio calculation, clinical index product ratio calculation, a logistic product ratio calculation, or a combination thereof. A mismatch of demand and capacity places stresses on the organ and, depending on the level of imbalance, can require that additional support be provided. Table 1 provides factors that contribute to demand and determine organ functional capacity that are useful for the devices, systems, and methods described herein.

TABLE 1

Factors influencing Demand and Capacity for Organ Function

| | Demand | | | Capacity | |
|---|---|---|---|---|---|
| Parameter | Factors | Measures | Parameter | Factors | Organ Specific Measures |
| Solute | Catabolic state Nutritional loading | Temperature Urea Nitrogen Appearance (UNA) Nitrogen Balance (NB) Protein Catabolic rate Acid-base and Electrolyte Balance | Underlying state of organ health | Functional Cardiac function Tissue Perfusion Inc vascular permeability Drug effects Other organ dysfunction Structural Pre-existing organ damage Acute organ injury | Heart: HR, BP. Cardiac output; Ejection fraction; cardiac enzymes; EKG changes Lung; Oxygenation; $CO_2$ removal; FeV1; pH, Imaging Liver: Bilirubin; Albumin; INR Kidney: - Urine volume; urine flow; BUN and Creatinine levels; Timed urinary clearances; kidney damage biomarkers Brain: Glasgow coma scores; cognitive function; neurological deficit Hematological: Platelets, Hemoglobin; WBC Overall functional status measures (EQ5, Charlson index) Imaging Ultrasound, CT and MRI scan, nuclear scans |
| Fluid | Volume for resuscitation and hemodynamic support Drugs and nutritional requirements | Daily fluid balance Cumulative fluid balance Fluid accumulation % of body wt | Process of Care | Dehydration Diuretics Sedation Paralytics Contrast Antibiotics Vasopressors | Kidney functional and damage markers Vasopressor index -Sedation score |
| Combined | Multi-organ failure | Scores: SOFA, Sepsis & Trauma | Organ Severity Stage | Etiology, duration, setting concomitant | Stage NYHA Stage 4, MELD Time in each Stage |

TABLE 1-continued

Factors influencing Demand and Capacity for Organ Function

| Demand | | | Capacity | | |
|---|---|---|---|---|---|
| Parameter | Factors | Measures | Parameter | Factors | Organ Specific Measures |
| | Sepsis, Trauma | | | risk factors and exposures, co-morbidities, functional status | Comorbidities |

Demand factors can include, but are not limited to a) the catabolic state that determines energy generation requirement to be met by liver and muscle; oxygen consumption to be met by heart and lung for tissue perfusion; and the solute load to be handled by the liver and the kidney; b) volume status including the overall amount of fluid in the body, as well as plasma and extracellular compartmental distribution, and c) demand placed by an individual organ dysfunction on other organs. Since all organs work in concert, the absence of function in one organ places an extra demand on the other organs, e.g., when the kidney fails there is accumulation of waste products that affects cardiac function (fluid overload, in heart, lung and brain). Additionally, some of the demand placed on the organs is iatrogenic, e.g., volume resuscitation for shock states and nutritional loading with enteral or parenteral solutions.

Capacity parameters can be specific for each organ and can represent functional elements required for homeostasis. Impaired capacity for any organ results from any underlying chronic disease states, e.g., hypertensive cardiomyopathy, diabetic nephropathy or chronic obstructive pulmonary disease (COPD) or from the acute disease process, e.g., sepsis or iatrogenic injury e.g. antibiotic nephrotoxicity. Additionally, strategies to support one organ may limit the inherent capacity of another organ to handle the demand, e.g., sedation for ventilator management reduces brain capacity, diuretics impairing renal concentration ability.

In some embodiments, at any given point, homeostasis can be achieved with a balance of demand and capacity for individual organs and in concert for all organs. Demand or capacity change in any organ or organ system can result in a mismatch that, depending on the degree and duration, may require other organs to respond appropriately. Most organs with inherent reserve capacity are able to increase capacity, e.g., the kidney can increase its glomerular filtration rate in response to a protein load. However, in most disease states the reserve capacity may be impaired from underlying chronic disease or is insufficient to meet the increased demand. The degree of demand/capacity mismatch determines the clinical symptom complex of organ dysfunction and depending on the severity and duration of the mismatch may trigger organ support.

Figure 2:
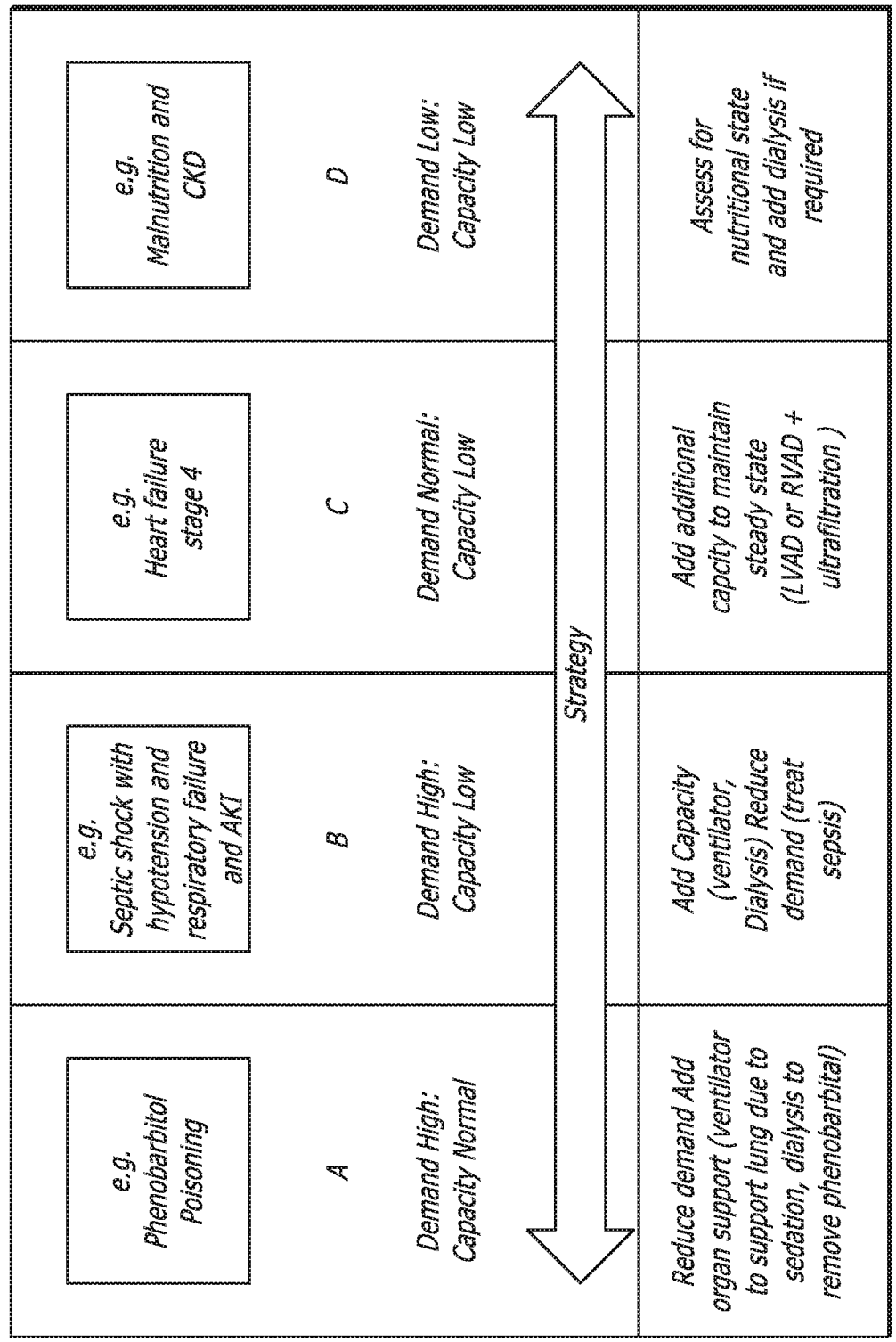
FIG. 2 illustrates demand v. capacity model to guide interventions for organ failure.

As illustrated in FIG. 2, patients can be classified into one of 4 category models based on the demand/capacity mismatch.

Model A: Demand increases and capacity is unchanged. For Model A, organ support can be provided to prevent toxicity to other organs and enhance capacity. In one embodiment, Model A can be a condition such as phenobarbital poisoning.

Model B: Demand same and capacity is reduced. For Model B, non-oliguric may need organ support to allow the organ to recover and prevent further damage. In some embodiments, capacity is added. In one embodiment, Model B can be a condition such as drug toxicity.

Model C: Demand increased and capacity reduced. For Model C, organs need to be supported until demand can be met. In one embodiment, Model C can be a condition such as sepsis and/or MOF.

Model D: Demand low and capacity low. For Model D, chronic conservative management may be required.

In some embodiments, the devices, systems, and methods described herein can assess mismatches of demand placed on any organ and available organ capacity. The devices, systems, and methods can then provide a quantifiable dynamic measure of organ support need. This model accounts for demand factors placed on any organ and the ability of the organ, individually or in concert with other organs, to handle the demand.

Kidney

In some embodiments, the devices, systems, and methods described herein can assist in determining if a patient is in need of renal intervention. In order to determine a demand-capacity index, kidney demand parameters and kidney capacity parameters can be compared.

Kidney demand parameters can include an organ failure assessment score, a fluid score, and a solute score. The organ failure assessment score can be points for non-renal organs based on SOFA categorization. The fluid score can be points based on accumulated fluid volumes. The solute score can be points based on catabolic state, catabolic rate, nitrogen balance, or a combination thereof.

Kidney capacity parameters can include a GFR score, a urine volume score, and a damage marker score. The GFR score can be points based on measured creatinine clearance or eGFR derived from a modified Jeliffe formula with creatinine corrected for fluid accumulation. The urine volume score can be points based on quantity of urine made in a specific time period of assessment. The specific time period of assessment can be about 1 hour, about 2 hours, about 3 hours, about 4 hours, about 6 hours, about 12 hours, about 24 hours, about 48 hours, between about 1 hour and about 48 hours, between about 2 hours and about 12 hours, between about 2 hours and about 6 hours, between about 6 hours and about 12 hours, or between about 6 hours and 24 hours. The damage marker score can be points based on specific biomarkers of kidney damage and their thresholds associated with severity. In some embodiments, the damage marker score points can be for a TIMP2*IGFBP (Nephrocheck) biomarker panel, scores (0.3-2) can be allocated points. In some embodiments, other biomarkers can be used, such as but not limited to, neutrophil gelatinase-associated lipocalin (NGAL).

The points for kidney demand parameters can be added to give a combined kidney demand score. Likewise, points for kidney capacity parameters can be added to give a combined kidney capacity score.

Then, a D/C ratio can be calculated. In some embodiments, the D/C ratio can be calculated by a clinical points ratio calculation, a logistic ratio calculation, a logistic additive ratio calculation, clinical index product ratio calculation, a logistic product ratio calculation, or a combination thereof. In one embodiment, the combined kidney demand score can be divided by the combined kidney capacity score to give a D/C ratio.

If the D/C ratio is low, conservative management can be provided to the patient. With conservative management, the D/C ratio as well as the clinical course of the patient can be monitored. If the D/C ratio and/or clinical course improve, removal of the patient from renal support can be considered. In such an improvement of D/C ratio and/or clinical course, the patient may have spontaneous reversal of renal function. If the D/C ratio and/or clinical course worsen, initiation of dialysis may be considered.

If the D/C ratio is in a target range, initiation of dialysis may be considered. After initiation dialysis, the D/C ratio as well as the clinical course of the patient can be monitored. If the D/C ratio and/or clinical course improve, a transition to a less invasive modality or even stopping therapy can be considered. With improvement, assessment for stopping therapy can be made as capacity parameters improve and patients can be weaned of dialysis with modality transitions e.g. CRRT switch to SLED or IHD. If the D/C ratio and/or clinical course worsen, a change in modality and/or an increase in therapy can be considered. Dose changes can involve changing frequency, duration of IHD or effluent volume in CRRT or adjustments and transitions of modality e.g. switch from IHD to CRRT.

If the D/C ratio is high, an assessment for futility can be performed. In some circumstances a family (or family member), a person with power of attorney, or a caregiver can make a decision based on a discussion with a physician. If the decision is that treatment is not futile or is not sure about futility, an offer of trial therapy can be offered. If the decision is that treatment is futile, an offer to transfer the patient to hospice care can be presented.

Figure 3:
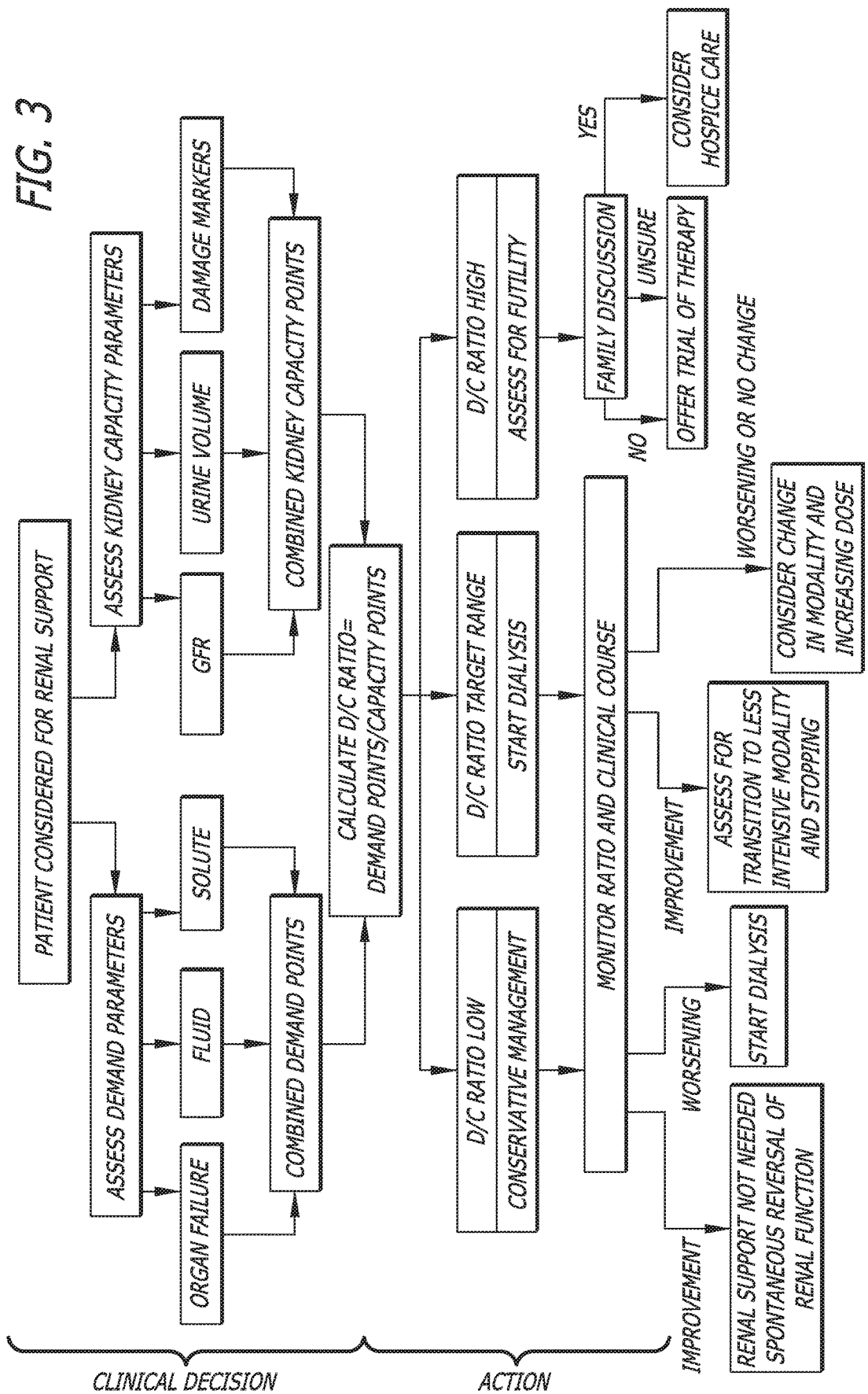
FIG. 3 illustrates a flow chart for utilization of the dynamic assessment of the demand-capacity mismatch to guide application of dialysis for renal support.

An exemplary flow chart for determining if a patient is in need of renal intervention is illustrated in FIG. 3. Other variations of this flow chart are within the scope of the present description.

In one embodiment, methods of treating kidney failure in a patient can include obtaining a plurality of measurements. The plurality of measurements can include at least a urine sample, a blood sample, a liquid input value, and a sequential organ failure assessment score for the patient. The methods can further include determining a kidney demand score from the plurality of measurements and determining a kidney capacity score from the plurality of measurements. Then, the kidney demand score can be divided by the kidney capacity score to provide a D/C ratio. Other calculation methods can be employed as described herein. The patient can be diagnosed as having kidney failure and needing intervention when the D/C ratio is in a target range. The methods can further include administering dialysis to the diagnosed patient.

In some embodiments, each of the at least one sequential organ failure assessment score, the at least one urine sample, the at least one blood sample, the at least one urine sample, the at least one blood sample, the at least one liquid input value, and the at least one sequential organ failure assessment score has a result that is given a score. The score can be in a range of 0 to 5 for each organ.

In some embodiments, the methods can further include diagnosing the patient as not needing intervention when the D/C ratio is in a low range. In other embodiments, the methods can further include diagnosing the patient as having kidney failure and intervention being futile when the D/C ratio is in a high range.

Lung

In some embodiments, the devices, systems, and methods described herein can assist in determining if a patient is in need of lung support. In order to determine a demand-capacity index, lung demand parameters and lung capacity parameters can be compared.

Lung demand parameters can include an organ failure assessment score, a fluid score, and a solute score. The organ failure assessment score can be points for non-lung organs based on SOFA categorization. The fluid score can be points based on accumulated fluid volumes. The solute score can be points based on catabolic state.

Lung capacity parameters can include an oxygenation score, a $CO_2$ removal score, a FeV1/pH score, and a damage marker and imaging score. The oxygenation score can be based on blood oxygenation based on a breath sample, a blood sample, and/or a pluseox reading. The $CO_2$ removal score can be based on blood oxygenation based on a breath sample, a blood sample, and/or a pluseox reading. The FeV1/pH score can be based on a Tiffeneau-Pinelli index, which is a calculated ratio used in the diagnosis of obstructive and restrictive lung disease. It represents the proportion of a person's vital capacity that they are able to expire in the first second of forced expiration to the full vital capacity. The damage marker and imaging score can be points based on specific biomarkers of lung damage and their thresholds associated with severity. The score can also be based on assessment of lung imaging, such as but not limited to x-rays.

The points for lung demand parameters can be added to give a combined lung demand score. Likewise, points for lung capacity parameters can be added to give a combined lung capacity score.

Then, a D/C ratio can be calculated. In some embodiments, the D/C ratio can be calculated by a clinical points ratio calculation, a logistic ratio calculation, a logistic additive ratio calculation, clinical index product ratio calculation, a logistic product ratio calculation, or a combination thereof. In one embodiment, the combined lung demand score can be divided by the combined lung capacity score to give a D/C ratio.

If the D/C ratio is low, conservative management can be provided to the patient. With conservative management, the D/C ratio as well as the clinical course of the patient can be monitored. If the D/C ratio and/or clinical course improve, removal of the patient from lung support can be considered. In such an improvement of D/C ratio and/or clinical course, the patient may have spontaneous reversal of lung function. If the D/C ratio and/or clinical course worsen, initiation of lung support may be considered.

If the D/C ratio is in a target range, initiation of lung support in the form of a ventilator, ECCOR, and/or ECMO may be considered. After initiation of lung support, the D/C ratio as well as the clinical course of the patient can be monitored. If the D/C ratio and/or clinical course improve, a transition to a less invasive modality or even stopping therapy can be considered. With improvement, assessment for stopping therapy can be made as capacity parameters improve and patients can be weaned of lung support with modality transitions. If the D/C ratio and/or clinical course worsen, a change in modality and/or an increase in therapy can be considered.

If the D/C ratio is high, an assessment for futility can be performed. In some circumstances a family (or family member), a person with power of attorney, or a caregiver can make a decision based on a discussion with a physician. If the decision is that treatment is not futile or is not sure about futility, an offer of trial therapy can be offered. If the decision is that treatment is futile, an offer to transfer the patient to hospice care can be presented.

Figure 4:
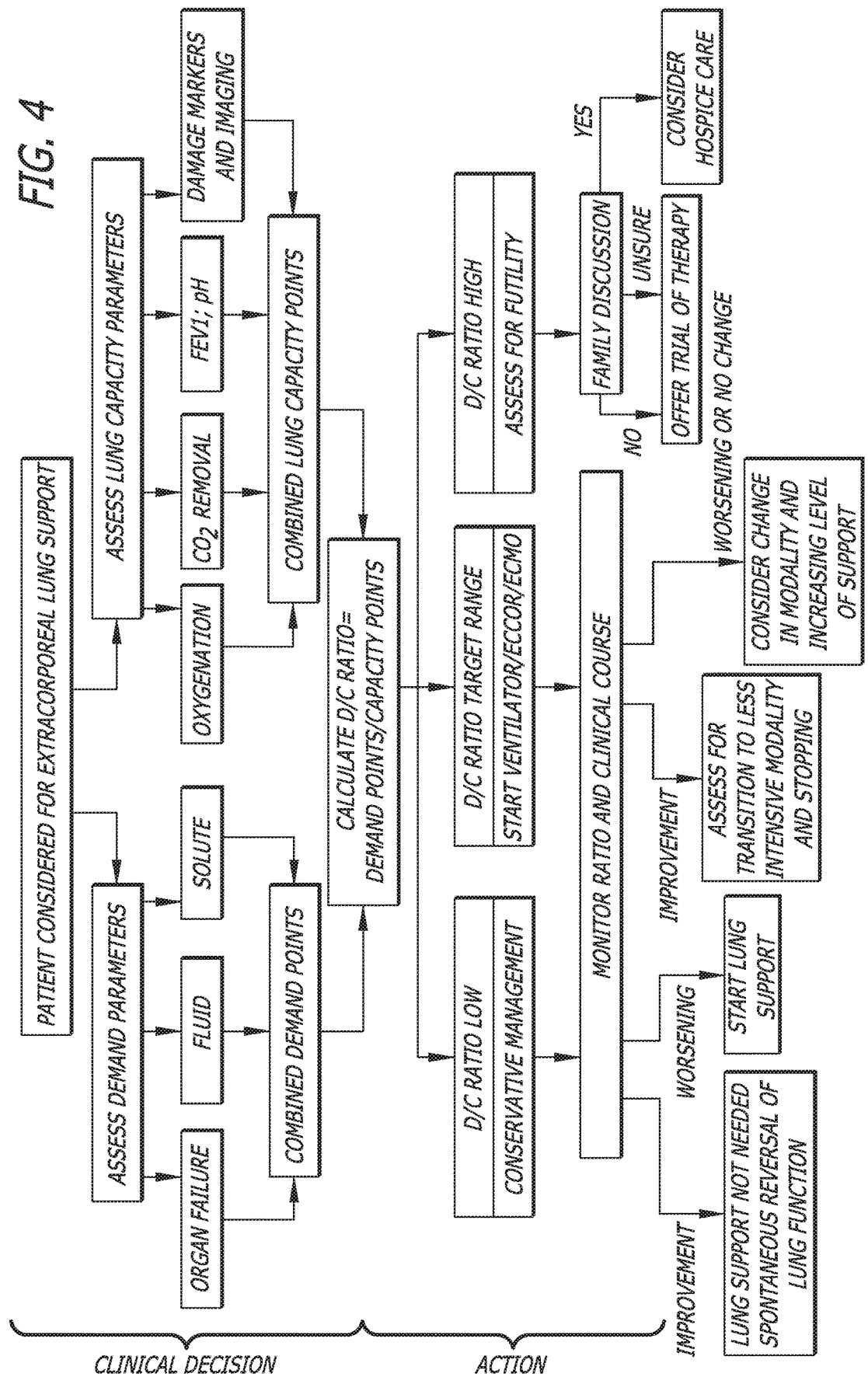
FIG. 4 illustrates a flow chart for utilization of the dynamic assessment of the demand-capacity mismatch to guide application of lung support.

An exemplary flow chart for determining if a patient is in need of lung intervention is illustrated in FIG. 4. Other variations of this flow chart are within the scope of the present description.

In one embodiment, methods of treating lung failure in a patient can include obtaining a plurality of measurements. The plurality of measurements can include at least a blood sample, a $pO_2$, a $CO_2$ removal value, a FeV1 test, a pH value, and a sequential organ failure assessment score. The methods can further include determining a lung demand score from the plurality of measurements and determining a lung capacity score from the plurality of measurements. Then, the lung demand score can be divided by the lung capacity score to provide a D/C ratio. Other calculation methods can be employed as described herein. The patient can be diagnosed as having lung failure and needing intervention when the D/C ratio is in a target range. The methods can further include administering a ventilator, ECCOR, ECMO, or a combination thereof to the diagnosed patient.

In some embodiments, each of the blood sample, the $pO_2$, the $CO_2$ removal value, the FeV1 test, the pH value, and a sequential organ failure assessment score has a result that is given a score. The score can be in a range of 0 to 5 for each organ.

In some embodiments, the methods can further include diagnosing the patient as not needing intervention when the D/C ratio is in a low range. In other embodiments, the methods can further include diagnosing the patient as having lung failure and intervention being futile when the D/C ratio is in a high range.

Heart

In some embodiments, the devices, systems, and methods described herein can assist in determining if a patient is in need of heart support. In order to determine a demand-capacity index, heart demand parameters and heart capacity parameters can be compared.

Heart demand parameters can include an organ failure assessment score, a fluid score, and a solute score. The organ failure assessment score can be points for non-heart organs based on SOFA categorization. The fluid score can be points based on accumulated fluid volumes. The solute score can be points based on catabolic state.

Heart capacity parameters can include a heart rate/EKG score, a blood pressure/mean arterial pressure (MAP) score, a cardiac output score, and a damage marker and imaging score.

The heart rate/EKG score can be based on pulse measurements performed manually or automatically using a machine such as but not limited to an EKG. The blood pressure/MAP score can be based on measurements performed manually or automatically using a machine. The cardiac output score can be based on sensing measurements and/or blood tests. The damage marker and imaging score can be points based on specific biomarkers of heart/cardiac damage and their thresholds associated with severity. The score can also be based on assessment of heart/cardiac imaging, such as but not limited to x-rays.

The points for heart demand parameters can be added to give a combined heart demand score. Likewise, points for heart capacity parameters can be added to give a combined heart capacity score.

Then, a D/C ratio can be calculated. In some embodiments, the D/C ratio can be calculated by a clinical points ratio calculation, a logistic ratio calculation, a logistic additive ratio calculation, clinical index product ratio calculation, a logistic product ratio calculation, or a combination thereof. In one embodiment, the combined heart demand score can be divided by the combined heart capacity score to give a D/C ratio.

If the D/C ratio is low, conservative management can be provided to the patient. With conservative management, the D/C ratio as well as the clinical course of the patient can be monitored. If the D/C ratio and/or clinical course improve, removal of the patient from heart support can be considered. In such an improvement of D/C ratio and/or clinical course, the patient may have spontaneous reversal of heart function. If the D/C ratio and/or clinical course worsen, initiation of heart support may be considered.

If the D/C ratio is in a target range, initiation of heart support in the form of a balloon pump, ventricular assist device (VAD), and/or heartmate may be considered. After initiation of heart support, the D/C ratio as well as the clinical course of the patient can be monitored. If the D/C ratio and/or clinical course improve, a transition to a less invasive modality or even stopping therapy can be considered. With improvement, assessment for stopping therapy can be made as capacity parameters improve and patients can be weaned of heart support with modality transitions. If the D/C ratio and/or clinical course worsen, a change in modality and/or an increase in therapy can be considered.

If the D/C ratio is high, an assessment for futility can be performed. In some circumstances a family (or family member), a person with power of attorney, or a caregiver can make a decision based on a discussion with a physician. If the decision is that treatment is not futile or is not sure about futility, an offer of trial therapy can be offered. If the decision is that treatment is futile, an offer to transfer the patient to hospice care can be presented.

Figure 5:
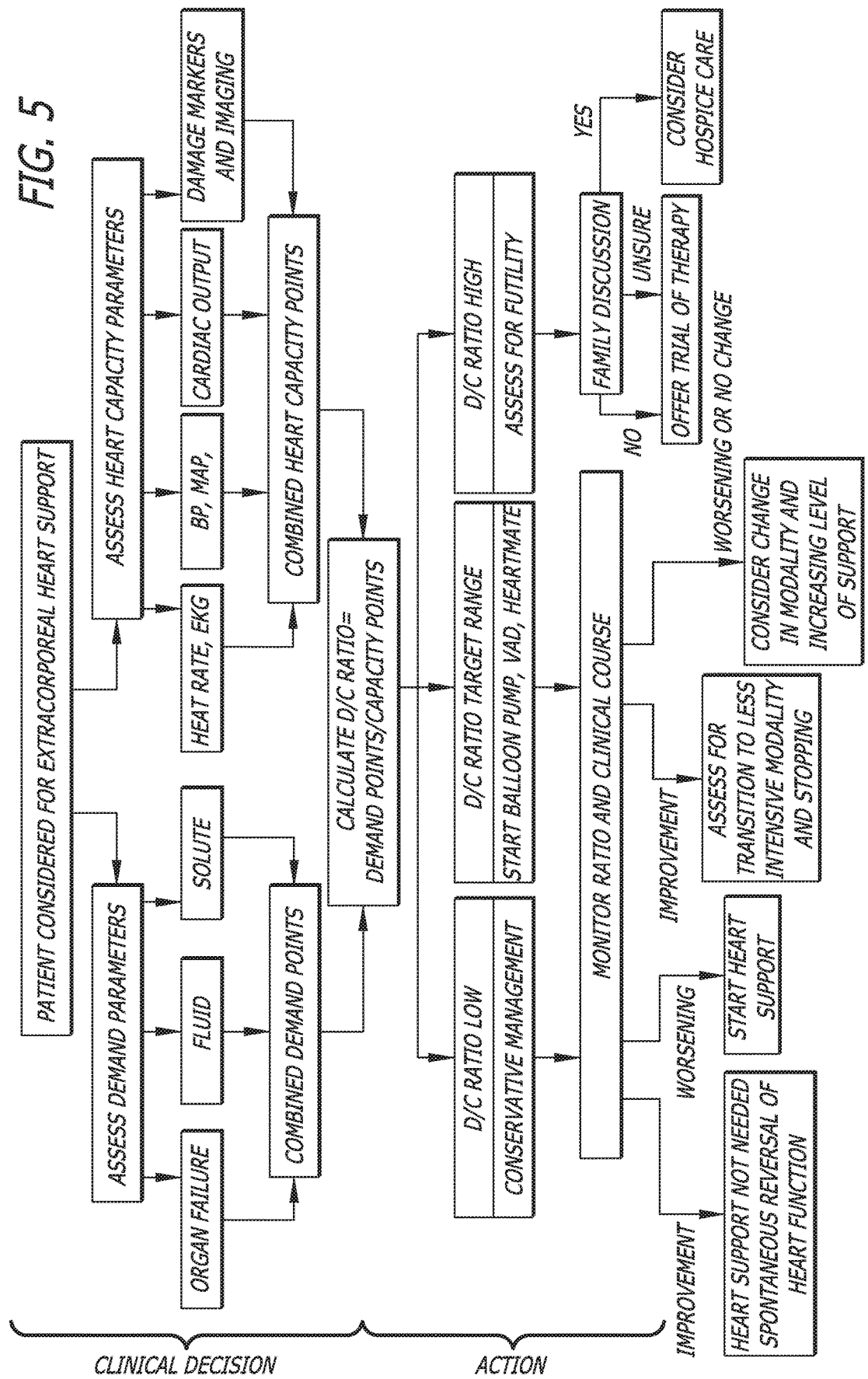
FIG. 5 illustrates a flow chart for utilization of the dynamic assessment of the demand-capacity mismatch to guide application of heart support.

An exemplary flow chart for determining if a patient is in need of heart or cardiac intervention is illustrated in FIG. 5. Other variations of this flow chart are within the scope of the present description.

In one embodiment, methods of treating heart failure in a patient can include obtaining a plurality of measurements. The plurality of measurements can include at least a heart rate, a blood pressure, a cardiac output, and a sequential organ failure assessment score. The methods can further include determining a heart demand score from the plurality of measurements and determining a heart capacity score from the plurality of measurements. Then, the heart demand score can be divided by the heart capacity score to provide a D/C ratio. Other calculation methods can be employed as described herein. The patient can be diagnosed as having heart failure and needing intervention when the D/C ratio is in a target range. The methods can further include administering a balloon pump, a VAD, a heartmate, or a combination thereof to the diagnosed patient.

In some embodiments, each of the heart rate, the blood pressure, the cardiac output, and the sequential organ failure assessment score has a result that is given a score. The score can be in a range of 0 to 5 for each organ.

In some embodiments, the methods can further include diagnosing the patient as not needing intervention when the D/C ratio is in a low range. In other embodiments, the methods can further include diagnosing the patient as having heart failure and intervention being futile when the D/C ratio is in a high range.

Liver

In some embodiments, the devices, systems, and methods described herein can assist in determining if a patient is in need of liver support. In order to determine a demand-capacity index, liver demand parameters and liver capacity parameters can be compared.

Liver demand parameters can include an organ failure assessment score, a fluid score, and a solute score. The organ failure assessment score can be points for non-liver organs based on SOFA categorization. The fluid score can be points based on accumulated fluid volumes. The solute score can be points based on catabolic state.

Liver capacity parameters can include a bilirubin score, an albumin score, a liver function test (INR) score, a Model for End-Stage Liver Disease (MELD) score, and a damage marker and imaging score.

The bilirubin score can be based on blood assay measurements. The albumin score can be based on blood assay measurements. The INR score can be based on blood testing to determine the thickness of blood. The MELD score can be based on a measurement of mortality risk in a patient with end-stage liver disease. It is used as a disease severity index to help prioritize allocation of organs for transplant. The damage marker and imaging score can be points based on specific biomarkers of liver damage and their thresholds associated with severity. The score can also be based on assessment of liver imaging, such as but not limited to x-rays.

The points for liver demand parameters can be added to give a combined liver demand score. Likewise, points for liver capacity parameters can be added to give a combined liver capacity score.

Then, a D/C ratio can be calculated. In some embodiments, the D/C ratio can be calculated by a clinical points ratio calculation, a logistic ratio calculation, a logistic additive ratio calculation, clinical index product ratio calculation, a logistic product ratio calculation, or a combination thereof. In one embodiment, the combined liver demand score can be divided by the combined liver capacity score to give a D/C ratio.

If the D/C ratio is low, conservative management can be provided to the patient. With conservative management, the D/C ratio as well as the clinical course of the patient can be monitored. If the D/C ratio and/or clinical course improve, removal of the patient from liver support can be considered. In such an improvement of D/C ratio and/or clinical course, the patient may have spontaneous reversal of liver function. If the D/C ratio and/or clinical course worsen, initiation of liver support may be considered.

If the D/C ratio is in a target range, initiation of liver support in the form of a molecular adsorbents recirculating system (MARS) and/or cell based liver support may be considered. After initiation of liver support, the D/C ratio as well as the clinical course of the patient can be monitored. If the D/C ratio and/or clinical course improve, a transition to a less invasive modality or even stopping therapy can be considered. With improvement, assessment for stopping therapy can be made as capacity parameters improve and patients can be weaned of liver support with modality transitions. If the D/C ratio and/or clinical course worsen, a change in modality and/or an increase in therapy can be considered.

If the D/C ratio is high, an assessment for futility can be performed. In some circumstances a family (or family member), a person with power of attorney, or a caregiver can make a decision based on a discussion with a physician. If the decision is that treatment is not futile or is not sure about futility, an offer of trial therapy can be offered. If the decision is that treatment is futile, an offer to transfer the patient to hospice care can be presented.

Figure 6:
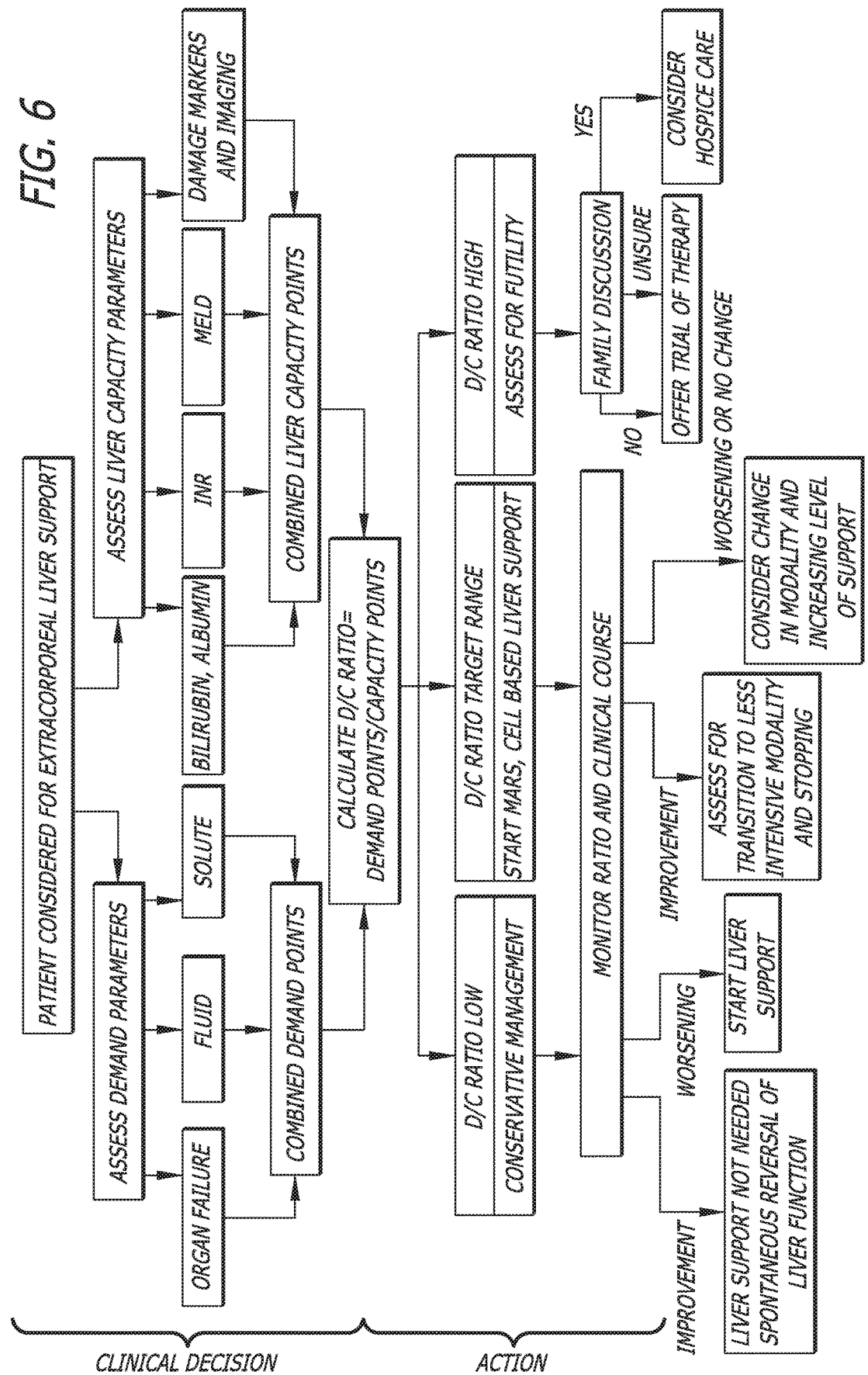
FIG. 6 illustrates a flow chart for utilization of the dynamic assessment of the demand-capacity mismatch to guide application of liver support.

An exemplary flow chart for determining if a patient is in need of liver intervention is illustrated in FIG. 6. Other variations of this flow chart are within the scope of the present description.

In one embodiment, methods of treating liver failure in a patient can include obtaining a plurality of measurements. The plurality of measurements can include at least a blood sample, an INR value, and a sequential organ failure assessment score. The methods can further include determining a liver demand score from the plurality of measurements and determining a liver capacity score from the plurality of measurements. Then, the liver demand score can be divided by the liver capacity score to provide a D/C ratio. Other calculation methods can be employed as described herein. The patient can be diagnosed as having liver failure and needing intervention when the D/C ratio is in a target range. The methods can further include administering molecular adsorbents recirculating system (MARS), cell based liver support, or a combination thereof to the diagnosed patient.

In some embodiments, each of the blood sample, the INR value, and the sequential organ failure assessment score has a result that is given a score. The score can be in a range of 0 to 5 for each organ.

In some embodiments, the methods can further include diagnosing the patient as not needing intervention when the D/C ratio is in a low range. In other embodiments, the methods can further include diagnosing the patient as having liver failure and intervention being futile when the D/C ratio is in a high range.

Multiple Organ Systems

Figure 7:
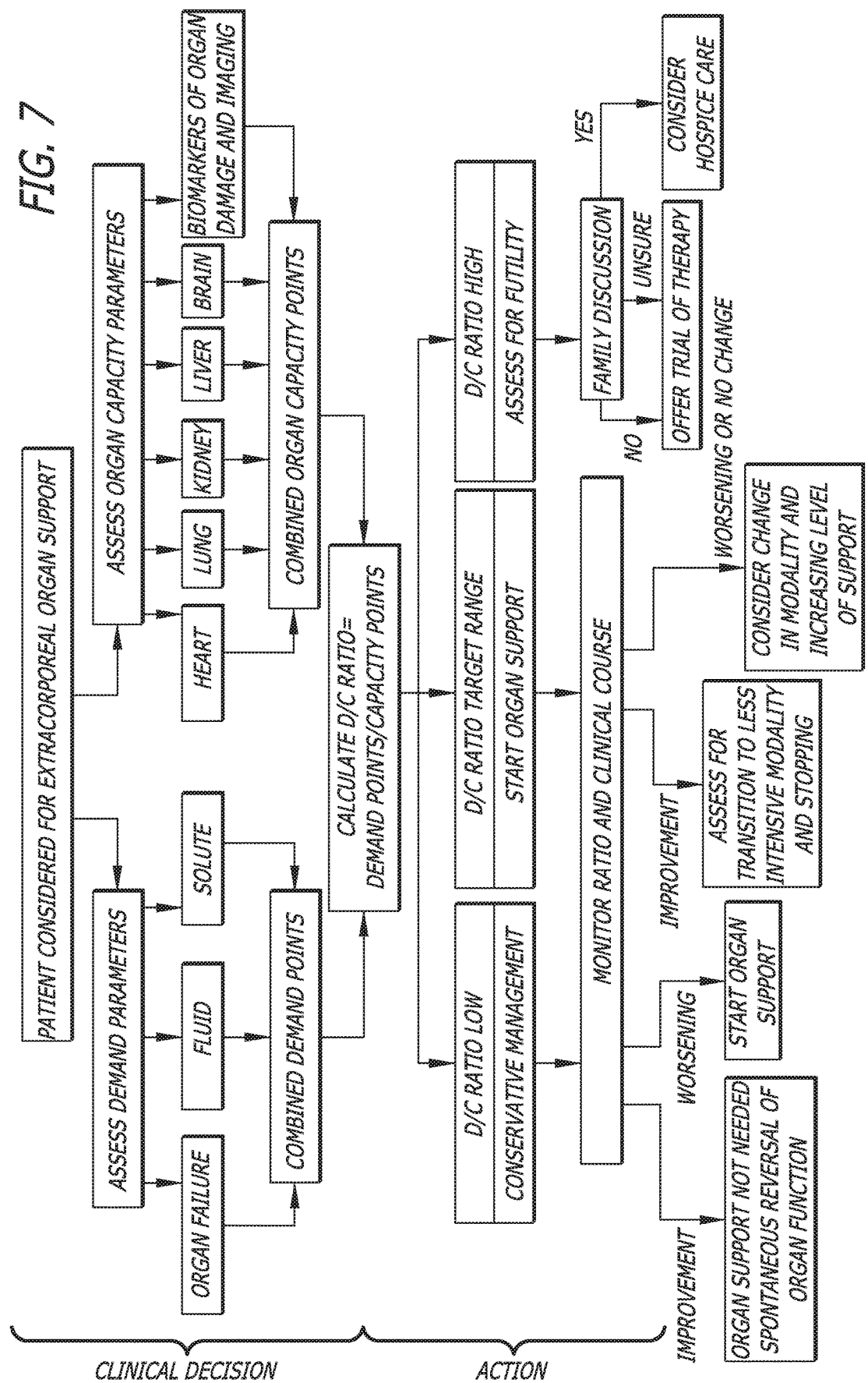
FIG. 7 illustrates a flow chart for utilization of the dynamic assessment of the demand-capacity mismatch to guide application of organ support.

In some embodiments, the devices, systems, and methods described herein can assist in determining if a patient is in need of organ support. Organ support can include a combination of organ systems, such as but not limited to the heart, the lungs, the kidneys, the liver, and the brain. In order to determine a demand-capacity index, demand parameters and capacity parameters for a combination of organ system can be compared. An example combination of organ systems is illustrated in FIG. 7.

Demand parameters can include an organ failure assessment score, a fluid score, and a solute score. The organ failure assessment score can be points for organs based on SOFA categorization. The fluid score can be points based on accumulated fluid volumes. The solute score can be points based on catabolic state.

Capacity parameters can include capacity parameters for each organ system. Kidney capacity parameters can include a GFR score, a urine volume score, and a tubular function score. Heart capacity parameters can include a heart rate/EKG score, a blood pressure/mean arterial pressure (MAP) score, and a cardiac output score. Lung capacity parameters can include a $pO_2$ score, an oxygenation score, a $CO_2$ removal score, and a FeV1/pH score. Liver capacity parameters can include a bilirubin score, an albumin score, a liver function test (INR) score, and a Model for End-Stage Liver Disease (MELD) score. Brain capacity parameters can include a Glasgow coma scale (GCS) score and a neuro deficit score. Further, a damage marker score can include assessment of biomarkers of organ damage. An imaging score can include scores from images of different organ systems. Images can include x-rays, ultrasounds, CT scans, MRIs, photographs, topographical scans, CAT scans, and the like.

The points for demand parameters can be added to give a combined demand score. Likewise, points for capacity parameters can be added to give a combined capacity score.

Then, a D/C ratio can be calculated. In some embodiments, the D/C ratio can be calculated by a clinical points ratio calculation, a logistic ratio calculation, a logistic additive ratio calculation, clinical index product ratio calculation, a logistic product ratio calculation, or a combination thereof. In one embodiment, the combined demand score can be divided by the combined capacity score to give a D/C ratio.

If the D/C ratio is low, conservative management can be provided to the patient. With conservative management, the D/C ratio as well as the clinical course of the patient can be monitored. If the D/C ratio and/or clinical course improve, removal of the patient from organ support can be considered. In such an improvement of D/C ratio and/or clinical course, the patient may have spontaneous reversal of organ function. If the D/C ratio and/or clinical course worsen, initiation of organ support may be considered.

If the D/C ratio is in a target range, initiation of organ support may be considered. After initiation of organ support, the D/C ratio as well as the clinical course of the patient can be monitored. If the D/C ratio and/or clinical course improve, a transition to a less invasive modality or even stopping therapy can be considered. With improvement, assessment for stopping therapy can be made as capacity parameters improve and patients can be weaned of organ support with modality transitions. If the D/C ratio and/or clinical course worsen, a change in modality and/or an increase in therapy can be considered.

If the D/C ratio is high, an assessment for futility can be performed. In some circumstances a family (or family member), a person with power of attorney, or a caregiver can make a decision based on a discussion with a physician. If the decision is that treatment is not futile or is not sure about futility, an offer of trial therapy can be offered. If the decision is that treatment is futile, an offer to transfer the patient to hospice care can be presented.

An exemplary flow chart for determining if a patient is in need of organ intervention is illustrated in FIG. 7. Other variations of this flow chart are within the scope of the present description.

In one embodiment, methods of treating organ failure in a patient are described. The methods can include obtaining a plurality of measurements. In some embodiments, the methods can further include determining an organ demand score from the plurality of measurements, determining an organ capacity score from the plurality of measurements, and dividing the organ demand score by the organ capacity score to provide a D/C ratio. Other calculation methods can be employed as described herein. The patient can be diagnosed as having organ failure and needing intervention when the D/C ratio is in a target range. If in the target range, organ support can be administered.

In some embodiments, the at least one heart output measurement includes a heart rate, a blood pressure, or a cardiac output.

In some embodiments, the at least one blood sample is used to determine blood pH, bilirubin levels, albumin levels, or a combination thereof.

In some embodiments, the organ failure is heart failure, lung failure, kidney failure, liver failure, brain failure, or a combination thereof.

In some embodiments, each of the at least one sequential organ failure assessment score, the at least one urine sample, the at least one blood sample, the at least one urine sample, the at least one blood sample, the at least one liquid input value, the at least one heart output measurement, and the at least one sequential organ failure assessment score has a result that is given a score. In some embodiments, the score is in a range of 0 to 5 for each organ.

In some embodiments, the organ support is molecular adsorbents recirculating system (MARS), cell based liver support, a balloon pump, a ventricular assist device (VAD), a heartmate, a ventilator, an ECMO, an ECCOR, dialysis, or a combination thereof.

In some embodiments, the plurality of measurements includes at least one urine sample, at least one blood sample, at least one liquid input value, at least one heart output measurement, at least one sequential organ failure assessment score for the patient, or a combination thereof.

In some embodiments, the methods can further include diagnosing the patient as not needing intervention when the D/C ratio is in a low range or diagnosing the patient as having organ failure and intervention being futile when the D/C ratio is in a high range.

In some embodiments, each organ's capacity parameter can be characterized by point scores with a range of 0-5 wherein 0 equates to complete organ failure and 5 equates to a fully functional organ for each parameter included in capacity. In other embodiments, the range can be 0 to 10, 0 to 20, 0 to 50, 0 to 100, or any other range that provides acceptable results.

In some embodiments, each organ's parameter of dysfunction severity can be expressed as a point score from 0-5 with 0 representing a normal organ and 5 a severely injured organ for each parameter included for the organ. In other embodiments, the range can be 0 to 10, 0 to 20, 0 to 50, 0 to 100, or any other range that provides acceptable results.

In some embodiments, demand parameters can be characterized by demand points computed based on the criteria for each of these parameters using the same scale of 0-5 for each parameter. In other embodiments, the range can be 0 to 10, 0 to 20, 0 to 50, 0 to 100, or any other range that provides acceptable results.

In some embodiments, the total demand placed on the organ can equate to catabolic demand points plus fluid demand points plus each additional organ demand points based on each organ's dysfunction severity to give total demand points.

In some embodiments, to assess organ support need, a ratio of total demand points/organ capacity points can be calculated.

In some embodiments, each organ can contribute to both the demand and capacity calculations. However, to compute the mismatch models scores are assigned in opposite directions when the organ is considered in the demand or capacity side.

In some embodiments, when considering adding dialysis, kidney are considered as the organ that needs to be supported with dialysis, so a low capacity score of 0 equates to anuric patients. If assessing need for ventilator support for the lung, an anuric patient can contribute 5 points on the demand side. So, depending on which organ support is needed, the models represent the mismatch for an individual organ. The same models will be utilized to assess the need for combined organ support.

Table 2 illustrates parameters that can be utilized for assessing the capacity and demand contributions for each organ with assigned point scores.

TABLE 2

Organ Specific Parameters to Assess Demand Capacity Components

| Range | CS* | DS# | Range | CS | DS | Range | CS | DS |
|---|---|---|---|---|---|---|---|---|
| Metabolic ||||||||| 
| Temperature ||| pH ||| Serum sodium (mMol/L) |||
| >40.9 | 0 | 5 | >7.69 | 0 | 4 | >179 | 0 | 4 |
| 39-40.9 | 2 | 3 | 7.60-7.69 | 2 | 3 | 160-179 | 1 | 3 |
| 38.5-38.9 | 4 | 1 | 7.50-7.59 | 3 | 1 | 155-159 | 3 | 2 |
| 36-38.4 | 5 | 0 | 7.33-7.49 | 4 | 0 | 150-154 | 3 | 1 |
| 34-35.9 | 3 | 1 | 7.25-7.32 | 3 | 2 | 130-149 | 4 | 0 |
| 32-33.9 | 4 | 2 | 7.15-7.24 | 3 | 3 | 120-129 | 3 | 2 |
| 30-31.9 | 2 | 3 | <7.15 | 0 | 4 | 111-119 | 1 | 3 |
| <30 | 1 | 4 ||||  <111 | 0 | 4 |
| Phosphate (mg/dL) ||| Nitrogen Balance (NB) (g/day) ||| Protein Cataboic Rate (PCR G/kg/day) |||
| <0.3 | 0 | 3 | >-8 | 0 | 4 | <0.4 | 0 | 3 |
| 1.0-1.9 | 2 | 2 | -5--8 | 2 | 3 | 0.4-0.5 | 2 | 2 |
| 2.0-2.4 | 3 | 1 | -4--1 | 3 | 1 | 0.6-0.8 | 3 | 1 |
| 2.5-3.0 | 4 | 0 | 0-3 | 4 | 0 | 0.9-1.1 | 4 | 0 |
| 3.0-3.5 | 3 | 1 | 4-5 | 3 | 2 | 1.2-1.5 | 3 | 1 |
| 3.5-4.0 | 2 | 2 | 6-7 | 3 | 3 | 1.6-2.0 | 2 | 2 |
| 4.0-5.0 | 1 | 3 | >7 | 0 | 4 | 2.1-2.5 | 1 | 3 |
| >5.0 | 0 | 4 |||| >2.5 | 0 | 4 |
| Energy requirements (kcal/kg) ||| Glucose levels (mg/dL) ||| Serum Potassium (mMol/L) |||
| <20 | 0 | 3 | <40 | 0 | 3 | <2.0 | 0 | 3 |
| 20-24 | 2 | 2 | 40-59 | 2 | 2 | 2.0-2.4 | 2 | 2 |
| 25-29 | 3 | 1 | 60-79 | 3 | 1 | 2.5-3.4 | 3 | 1 |
| 30-34 | 4 | 0 | 80-109 | 4 | 0 | 3.5-4.9 | 4 | 0 |
| 35-39 | 3 | 1 | 110-159 | 3 | 1 | 5.0-5.4 | 3 | 1 |
| 40-45 | 2 | 2 | 160-499 | 2 | 2 | 5.5-5.9 | 2 | 2 |
| >45 | 1 | 3 | >=500 | 1 | 3 | 6.0-6.9 | 1 | 3 |
|  |  |  |  |  |  | >=7.0 | 0 | 4 |
| Respiratory |||||||||
| Respiratory Rate ||| Oxygenation (use PaO2 if FiO2 < 50%, otherwise use A-a gradient) ||| PaO2/FiO2 |||
| >179 | 0 | 4 | A-a g >499 | 0 | 4 | <400 | 4 | 1 |
| 140-179 | 2 | 3 | A-a g 350-499 | 2 | 3 | <300 | 3 | 2 |
| 110-139 | 3 | 2 | A-a g 200-349 | 3 | 2 | <200 and MV& | 2 | 3 |
| 70-109 | 4 | 0 | A-a gr <200 * | 4 | 0 | <100 and MV | 1 | 4 |
| 55-69 | 3 | 2 | PaO2 = 61-70 | 3 | 1 ||||
| 40-54 | 2 | 3 | PaO2 = 55-60 | 2 | 3 ||||
| <40 | 0 | 4 | PaO2 <55 | 0 | 4 ||||
| Cardiovascular |||||||||
| Mean arterial pressure (mmHg) ||| Heart rate (beats per min) ||| Vasopressor use |||
| >159 | 0 | 4 | >179 | 0 | 4 | dop ≤ 5 or dob (any dose) | 3 | 2 |
| 130-159 | 2 | 3 | 140-179 | 2 | 3 ||||
| 110-129 | 3 | 2 | 110-139 | 3 | 2 | dop > 5 OR epi ≤ 0.1 OR nor epi ≤ 0.1 | 2 | 3 |
| 70-109 | 4 | 0 | 70-109 | 4 | 0 ||||
| 50-69 | 3 | 2 | 55-69 | 3 | 2 | dop > 15 OR epi > 0.1 OR nor > 0.1 | 1 | 4 |
| <50 | 0 | 4 | 40-54 | 2 | 3 ||||
| Kidney |||||||||
| Urine Volume ||| Estimated GFR ||| Fluid Balance as % of Body Weight |||
| <100 | 1 | 5 | 0-5 | 1 | 1 | 0-5% | 5 | 0 |
| 100-400 | 2 | 4 | 5.1-10 | 2 | 2 | 5-10% | 4 | 1 |
| 401-1000 | 3 | 3 | 10.1-15 | 3 | 3 | 10-15% | 3 | 2 |
| 1001-1500 | 4 | 2 | 15.1-30 | 4 | 4 | 15-20% | 2 | 3 |
| >1500 | 5 | 1 | >30 | 5 | 5 | >20% | 1 | 5 |
| Hematological |||||||||
| Hematocrit (%) ||| WBC (total/cmm in 1000's) ||| Platelets × 10³/µl |||
| >59.9 | 0 | 4 | >59.9 | 0 | 4 | <20 | 0 | 4 |
| 50-59.9 | 3 | 2 | 50-59.9 | 3 | 2 | <150 | 3 | 1 |

TABLE 2-continued

Organ Specific Parameters to Assess Demand Capacity Components

| 46-49.9 | 3 | 1 | 46-49.9 | 3 | 1 | <100 | 3 | 2 |
|---|---|---|---|---|---|---|---|---|
| 30-45.9 | 4 | 0 | 30-45.9 | 4 | 0 | <50 | 2 | 3 |
| 20-29.9 | 3 | 2 | 20-29.9 | 3 | 2 | <20 | 0 | 4 |
| <20 | 0 | 4 | | | | | | |

Liver

| Bilirubin (mg/dl) [μmol/L] | | | INR | | | Albumin (g/L) | | |
|---|---|---|---|---|---|---|---|---|
| 1.2-1.9 [>20-32] | 4 | 1 | <1.2 | 4 | 0 | >35 | 3 | 1 |
| 2.0-5.9 [33-101] | 3 | 2 | 1.2-1.6 | 3 | 1 | 28-35 | 2 | 2 |
| 6.0-11.9 [102-204] | 2 | 3 | 1.7-2.3 | 2 | 2 | <28 | 1 | 3 |
| >12.0 [>204] | 1 | 4 | 2.4-3.5 | 1 | 3 | | 0 | 4 |
| | | | >3.6 | 0 | 4 | | | |

In some embodiments, the D/C ratio is provided. In other embodiments, the D/C ratio can be determined. As described, the D/C ratio describes a mismatch of demand to capacity at any given time. Factors can be quantified based on measurements, done on a dynamic basis. Each organ can be assessed separately for its performance, and its contribution to overall homeostasis.

In some embodiments, individual components of the demand and capacity paradigm can also provide information on patient needs. Demand and capacity components can be addressed individually. For example, if the demand is largely due to the cumulative fluid balance then that parameter can be addressed with specific maneuvers to remove more fluid with dialysis.

Further, when assigning demand and/or capacity scores, particular components can more easily be identified as issues. For example, when a physician receives lab results, various reported values may not trigger interest in any particular result. However, when converted into the demand: capacity paradigm, outlying data become more identifiable and can be addressed as needed.

In some embodiments, the D/C ratio for any given organ or set of organs can be determined on a dynamic basis. In some embodiments, the D/C ratio can be determined on a regular interval. For example, in some embodiments, the D/C ratio can be calculated every second, every minute, every five minutes, every 30 minutes, every hour, or every day. In other embodiments, the D/C ratio can be determined as needed to make a therapy decision.

In some embodiments, the devices and/or systems can be integrated with biomarkers that can provide a decision support platform that is dynamic and responsive to change. This dynamic and responsive support platform can inform clinicians of need to intervene, window of opportunity to intervene with, and/or best options to utilize.

In some embodiments, the D/C ratio can be calculated every time new data is provided.

In some embodiments, therapy decisions can be dynamically based on calculated D/C ratios. For example, changes in D/C ratio over time can assist in determining therapy decisions.

If D/C ratio improves, the type of therapy or the magnitude of therapy may be adjusted. In some embodiments, a less intensive modality of treatment or a lesser dose may be provided. In other embodiments, termination of treatment may be required.

If D/C ratio worsens or does not change, the type of therapy or the magnitude of therapy may be adjusted or a decision regarding futility can be assessed. In some embodiments, a more intensive modality of treatment or a greater dose may be provided. In other embodiments, termination of treatment may be required because the treatment is not working and may be futile.

In some embodiments, when using dynamic D/C ratios, percentage of change can assist in therapy decisions. For example, a 25% reduction in D/C ratio may suggest a different course of action than a 50% reduction in D/C ratio. Likewise, a 25% increase in D/C ratio may suggest a different course of action than a 50% increase in D/C ratio. Thus, a user can provide different therapy decisions based on the percent change in D/C ratio.

In some embodiments, D/C ratios are calculated for organ systems even if in a low range or if intervention is not likely. This calculation can be considered preventative. In some embodiments, patients' D/C ratios care dynamically calculated even if no organ support is needed. In such an embodiment, if a D/C ratio enters a target range or even begins to elevate, intervention can be established as needed rather than waiting for obvious signs.

In some embodiments, D/C ratios can be established and dynamic D/C ratios calculated on otherwise healthy individuals.

In some embodiments, dynamic D/C ratios can be used for patients undergoing surgery. Often patients undergoing surgery may not be responsive or able to alert staff that a problem exists. If a system is dynamically determining D/C ratios as described herein, organ support can be provided as needed.

In some embodiments, different organ systems can be added to or removed from a dynamic D/C ratio determination. For example, kidney, lung, heart, liver organ system D/C ratios can be determined dynamically and one or more system can be removed from the dynamic calculation if that system's D/C ratio enters a low range and is considered not to need further intervention. Conversely, one or more system can be added to the dynamic calculation if that system's D/C ratio enters a target range and is considered to need further intervention.

In some embodiments, each organ's contribution to demand and capacity can be based on the SOFA score. Thus, in some embodiments, an organ system is not removed from the calculation, but rather the organ support technique for an individual organ maybe adjusted. In some embodiments, when an organ no longer needs attention, it can be moved from the demand portion of the paradigm to the capacity portion of the paradigm. Likewise, when an organ needs attention, it can be moved from the capacity portion of the paradigm to the demand portion of the paradigm.

In some embodiments, the methods described for quantifying the D/C ratio or mismatch can be utilized as a decision support system to help physicians decide the need for extracorporeal support. These methods can reduce variations in care, optimize resource management, and/or improve patient centered outcomes.

In some embodiments, when multiple organs are down, more than one form of support maybe required, e.g., combination of ECMO and ECCOR with dialysis for respiratory and kidney failure or a left or right ventricular assist device (LVAD or RVAD) with dialysis for heart failure and kidney injury. In these situations, the overall capacity of the organs can be enhanced with external devices. As organ failures improve, support for individual organs can be adjusted independently based on demand capacity mismatch differences.

In one embodiment, ventilator management can continue in absence of dialysis and similarly dialysis could continue in absence of ventilator management.

In some embodiments, the demand/capacity mismatch model described herein can be used to define need for intervention in patients in need of therapeutic intervention. Therapeutic intervention can be for one or more organ systems and/or conditions.

In some embodiments, the organ system is an integumentary system, a muscular system, a skeletal system, a nervous system, a circulatory system, a lymphatic system, a respiratory system, an endocrine system, a urinary system, a reproductive system, a digestive system, or a combination thereof. In some embodiments, the organ system is an organ. In some embodiments, the organ is a muscle (e.g., skeletal muscle) a stomach, an intestine (e.g., small intestine, large intestine), a kidney, a bladder, a liver, a heart, a lung, a diaphragm, or a combination thereof. In other embodiments, the organ is a kidney, a heart, a lung, a liver, or a combination thereof. In some embodiments, the organ system related disease is acute kidney injury.

In one embodiment, the demand/capacity mismatch model described herein can be used to define need for dialysis in patients with kidney dysfunction. In critically ill patients, acute kidney injury (AKI) is associated with mortality rates in excess of 50%, despite remarkable improvements in the overall intensive care treatment and availability of new Renal Replacement Therapy (RRT) methods. Potential modifiable factors that could impact the clinical course and outcomes of patients with severe AKI include dialysis dose, modality, and timing of dialysis initiation. During the last decade, several large randomized clinical trials of dialysis dose and modality have failed to demonstrate a survival benefit. Few randomized trials and meta-analysis suggested that early RRT initiation may have a beneficial effect on survival two. In a single center ELAIN trial, results showed a marked mortality benefit at 90 days for patients initiated on early dialysis (CRRT) within 8 hrs of reaching at Stage II AKI in comparison to patients who had delayed initiation within 12 hrs of reaching Stage III AKI (mortality 39.3% in the early group 54.7% in the delayed group (P=0.03) absolute risk reduction of −15.4% (95% CI, −28.1% to −2.6%). Inclusion criteria required a plasma NGAL level of >150 ng/mL to establish ongoing kidney damage.

In contrast, another study reported the results from an AKIKI multicenter study in 31 French ICU'S. Patients were randomly assigned to either immediate renal-replacement therapy (early strategy) or a delayed strategy in which such therapy was initiated if patients had development of severe hyperkalemia, uremia, metabolic acidosis, pulmonary edema, or severe oliguria that persisted for more than 72 hours after randomization. More than half the patients were treated with intermittent hemodialysis. The primary outcome, mortality at 60 days, was similar in the two groups (48.5% in the early-strategy group and 49.7% in the delayed strategy group, P=0.79). However, 49% of the patients in the delayed-strategy group never received dialysis. While dialysis could be avoided in almost half the patients, those who ultimately required dialysis in the delayed group had worsening metabolic and clinical status when they started dialysis. Although the differences were insignificant when adjusted for baseline severity of illness (Simplified Acute Physiology Score [SAPS] III), the patients who did not receive renal-replacement therapy had the lowest severity-of-illness scores at baseline and had the lowest mortality (37.1%), followed by patients who received therapy early (48.5%) and the patients who received therapy late (61.8%).

These two studies and the design of ongoing clinical trials suggest that a reproducible approach for evaluating patients who need dialysis in the ICU setting has not been achieved. Given the current knowledge in this field, there is no adequate evidence to propose any particular biomarker or multi-markers as criteria to start. Studies evaluating time of initiation of RRT have demonstrated serum creatinine (sCr) and BUN levels are relatively insensitive as a target criterion for starting RRT. The heterogeneous definitions of earlier intervention in these studies highlight the need for better parameters to define the need for renal support. Timing of renal support should be based on various biomarkers of AKI as these will likely provide earlier indications of ongoing renal damage prior to elevation of sCr or urine output has been suggested. Previous single center studies have shown improved prediction of RRT need based on cystatin C as a functional marker of AKI in comparison to the performance of the Liano score. Recent studies have also proposed NGAL, IL-18 and KIM-1 as additional biomarkers predicting RRT. However, the positive predictive value is quite low (0.12 for NGAL).

In the absence of any standardized criteria of when to initiate dialysis, there is currently a significant variance in the timing of commencement of dialysis for patients with AKI particularly in the ICU setting. This has an impact on patient outcomes, and thus the total cost of care. Timely commencement of dialysis for such patients can help significantly improve outcomes for patients and reduce cost. Evidence to date highlights a need for dynamic risk-stratification tools to identify patients who will or will not need renal replacement therapy for management of their acute kidney injury.

In some embodiments, timely application of renal-replacement therapy may consider individual patient characteristics, process-of-care elements, and/or logistics to achieve therapeutic goals.

The present devices, systems, and methods utilize a demand/capacity ratio or index to quantify factors that define the need to support critically-ill patients with RRT. Based on the principle that at any given time, the need for renal support depends on the balance between the demand and the renal functional capacity, a mismatch of demand and capacity places a stress on the kidney and, depending on the level of imbalance, requires additional renal support to be provided. Factors have been identified that contribute to demand and determine renal excretory capacity.

As illustrated in Table 3, factors can be quantified based on simple measurements, done on a dynamic basis. A tool has been created to evaluate the demand/capacity mismatch and it is expressed as the mismatch of demand to capacity at any given time.

TABLE 3

Factors contributing to increased demand and altered renal functional capacity.

| | Demand | | | Capacity | |
|---|---|---|---|---|---|
| Parameter | Factors | Measures | Parameter | Factors | Measures |
| Solute | Catabolic state Nutritional loading | Urea Nitrogen Appearance (UNA) Negative Nitrogen Balance (NNB) Protein Catabolic rate Acid-base and Electrolyte Balance | GFR | Hemodynamic Cardiac function Tissue Perfusion Inc vascular permeability Drug effects Other organ dysfunction Structural Pre-existing kidney damage Acute kidney injury | Timed urinary clearances Measured iothalamate clearances Surrogate serum markers (BUN, Creatinine, cystatin C) Imaging Renal scan, MRI scan |
| Fluid | Volume for resuscitation and hemodynamic support Drugs and nutritional requirements | Daily fluid balance Cumulative fluid balance Fluid accumulation % of body wt | Urine output | Process of care Dehydration Diuretics | Urine volume Urine flow |
| Combined | Multi-organ failure Sepsis, Trauma | Scores: SOFA, Sepsis & Trauma | AKI Stage | Etiology, duration, setting concomitant risk factors and exposures, co-morbidities, CKD, functional status | Stage 1-3 Time in each Stage comorbidities functional status measures (EQ5, Charlson index) |

Table 4 details calculations for the demand capacity model for renal support. Data shown below demonstrates that the D/C ratio is strongly associated with the need for renal support and importantly appears to show predictive validity.

TABLE 4

Calculation of Demand and Capacity for Kidney Models.

| | Demand | | | Capacity | |
|---|---|---|---|---|---|
| Parameter | Measures | Comments | Parameter | Measurement | Comments |
| Organ Failure | SOFA scores | Overall SOFA and non-renal SOFA scores at day of peak and day of dialysis initiation | sCr | Fluid balance(FB) adjusted creat = sCr × CF | Correction factor (CF) = [hospital admission weight (kg) × 0.6 + Σ (daily fluid balance)]/hospital admission weight × 0.6 |
| Fluid | Daily fluid Balance Cumulative fluid balance Fluid accumulation % of body wt | Daily fluid balance computed from all intakes and outputs Cumulative fluid balance reflects net balance from admission Fluid accumulation % of body wt: (Σ daily (fluid intake (L) − total output (L))/body weight (in kilograms)) × 100. Baseline body weight was based on initial hospital admission weight. | GFR | aMDRD and Modified Jelliffe GFR The adjusted sCr was substituted for the measured sCr in the Jelliffe equation to compute the Modified Jelliffe GFR and the equations were indexed to 1.73 m² BSA | Abbreviated MDRD (aMDRD) = 186 × [serm creatinine(mg/dL)]$^{-1.154}$ × [age]$^{-0.203}$ × [0.742 if patient is female] × [1.21 if patient is African-American]. Jelliffe Eq: ((Volume of distribution × (sCr on day 1 − sCr on day 2)) + creatinine production) × 100/1440/average sCr. Creatinine production (mg/day) = 29.305 − (0.203 × age) × weight × (1.037 − (0.0338 × average Cr)) × correction for gender (0.85 for males and 0.765 for females). |

TABLE 4-continued

Calculation of Demand and Capacity for Kidney Models.

| Demand | | | Capacity | | |
|---|---|---|---|---|---|
| Parameter | Measures | Comments | Parameter | Measurement | Comments |
| Solute | Catabolic state | Urea nitrogen appearance rate: [BUN2 − BUN1] × 0.6 × BW + [BUN1 + BUN2] × BUN2 Nitrogen Balance (NB): Total Nitrogen intake − UNA/day Protein catabolic Rate (PCR): ((0.97 × UNA) × 6.25)/BW in Kg Energy requirements: Males*: 66.5 + (13.7 × BW in kg) + (5.0 × Ht. in cm) − (6.8 × age) × SF × AF Females*: 655 + (9.6 × BW in kg) + (1.8 × Ht in cm) − (4.7 × age in Yrs.) Electrolyte and acid base derangements | Urine Output | Urine Volume | In patients with a urinary output less than 100 mL in 24 hours, the GFR was considered zero. |

In some embodiments, five different models can be used to evaluate performance of the Demand Capacity Index for the kidney. Initially four variables were considered for inclusion in the model: urinary output (UO), cumulative fluid balance (CFB), non-renal SOFA score and glomerular filtration rate (GFR—assessed by the modified Jelliffe equation). UO and CFB were computed as mL/kg/h and percentage of change in baseline body weight, respectively.

Capacity Components

Urine Output and GFR

In patients with a urinary output less than 100 mL in 24 hours, the GFR was considered zero. Patients presenting a volume higher than 100 mL we quantified the urine volume and stratified based on the ranges described in Table 2. In patients with UOP>100 mL/24 hrs, GFR (in mL/min) was estimated using the Jelliffe equation for unstable kidney function. This equation has been validated in patients with non-steady state kidney function.

To calculate GFR by Jelliffe, the volume of distribution of sCr can be multiplied by the difference between the sCr measured the first day (initial creatinine) and the second day and creatinine production is added to this product:

((Volume of distribution×(sCr on day 1−sCr on day 2))+creatinine production)×100/1440/average sCr.

This simplified equation is accurate for sCr measured every 24 hours. When sCr is rising, sCr on day 2 can be used instead of average sCr. The volume of distribution in deciliters can be estimated to equal 0.4×weight (kg)×10. Body weight is defined as initial hospital admission weight. Creatinine production (mg/day) can be computed using the equation:

29.305−(0.203×age))×weight×(1.037−(0.0338×average Cr))×correction for gender (0.85 for males and 0.765 for females).

Since this equation takes into account sCr fluctuations and creatinine production over time, but not fluid balance variations, which can also significantly influence serum creatinine measurements, every sCr can be adjusted according to the cumulative daily fluid balance using the equation:

Adjusted creatinine=sCr×correction factor

Correction factor=[hospital admission weight (kg)× 0.6+Σ(daily fluid balance)]/hospital admission weight×0.6.

The adjusted sCr was substituted for the measured sCr in the Jelliffe equation to compute the Modified Jelliffe GFR. Jelliffe and Modified Jelliffe equations were indexed to 1.73 m2 body surface area.

Demand Components

Cumulative Fluid Balance

Fluid balance was computed for each day using the sum of daily fluid intake (L) from which we subtracted total output (L). To quantify cumulative fluid balance in relation to body weight, we used the following formula:

(Sum of daily (fluid intake (L)−total output (L))/ body weight (in kilograms))×100.

The term "percentage of fluid accumulation" is used to define the percentage of cumulative fluid balance adjusted for body weight. Baseline body weight was based on initial hospital admission weight.

Assessment (SOFA) and Non Renal SOFA Scores

An assigned point score was calculated for each organ based on the SOFA scoring system that is illustrated in Table 5. This scoring system was initially developed to characterize organ dysfunction in septic patients and is widely utilized to assess the severity of organ dysfunction and for predicting outcomes. A recent variation of this scoring system (Quick SOFA; qSOFA) has been proposed for use in classifying patients with sepsis.

Urea Nitrogen Appearance (UNA), Protein Catabolic Rate (PCR) and Nitrogen Balance (NB)

Protein nitrogen appearance (PNA) estimated from urea nitrogen appearance (UNA) can reflect dietary protein intake and is an important index of nutrition and metabolic status. It can estimate the metabolic demand in critically ill patients. The daily nitrogen balance (NB) computed from the total nitrogen intake and UNA can reflect the underlying state of protein catabolism and has been correlated with the need for dialysis. Critically ill patients can often have large negative nitrogen balance which may be difficult to correct despite aggressive nutritional replacement. Protein catabolic rate (PCR) can be calculated from the UNA and reflects the catabolic state and the nutritional support that is being provided.

Basal Metabolic Rate

Resting energy expenditure can be correlated to the size of the body cell mass and is independent of age and sex. The variables used to calculate basal metabolic rates in the Harris-Benedict equation are height, weight, age, and sex. In critically ill patients, basal metabolic rate can be increased according to disease severity and presence of fever. The adjusted Harris-Benedict equation can utilize stress factor that accounts for disease severity and fever. IF: injury factor—1.0—Normal, Minor Surgery; 1.2—Long Bone Fracture; 1.0-1.2—Burn Post Graft; 1.3—COPD, Malnourished; 1.4—Severe Head Injury; 1.5-50% Burns; 1.0-1.5—Cancer; 1.6—Ventilator; 1.2-1.6—Major Surgery, Multiple Trauma, 0-20% Burns Pre Graft; 1.2-1.7—Acute Sepsis; 1.5-2.0—20-40% Burn Pre Graft; 2.0-50% Burn; AF: activity factor: 1.1 for each °C.>37° C. Compared to indirect calorimetry (IC), the equation can predict metabolic energy expenditure. This updated equation can be used to calculate the basal metabolic rate and total calories.

Cumulative Fluid Balance

Fluid balance for each day can be calculated using the sum of daily fluid intake (L) from which we subtracted total output (L). To quantify cumulative fluid balance in relation to body weight, the following formula can be used:

(Sum of daily (fluid intake (L)−total output (L))/
body weight (in kilograms))×100.

The term "percentage of fluid accumulation" can be used to define the percentage of cumulative fluid balance adjusted for body weight. In some embodiments, baseline body weight can be based on initial hospital admission weight.

TABLE 5

Sequential (Sepsis-Related) Organ Failure Assessment Score

| System | Score | | | | |
|---|---|---|---|---|---|
| | 0 | 1 | 2 | 3 | 4 |
| Respiration $P_{aO2}/F_{IO2}$, mmHg (KPa) | ≥400 (53.3) | <400 (53.3) | <300 (40) | <200 (26.7) with respiratory support | <100 (13.3) with respiratory support |
| Coagulation Platelets, ×10³/μL | ≥150 | <150 | <100 | <50 | <20 |
| Liver Bilirubin, mg/dL (μmol/L) | <1.2 (20) | 1.2-1.9 (20-32) | 2.0-5.9 (33-101) | 6.0-11.9 (102-204) | >12.0 (204) |
| Cardiovascular | MAP ≥ 70 mmHg | MAP < 70 mmHg | Dopamine <5 or dobutamine (any dose)[b] | Dopamine 5.1-15 or epinephrine ≤0.1 or norepinephrine ≤0.1[b] | Dopamine >15 or epinephrine ≤0.1 or norepinephrine ≤0.1[b] |
| Central Nervous System Glasgow Coma Scale Score[c] | 15 | 13-14 | 10-12 | 6-9 | 6 |
| Renal Creatinine, mg/dL (μmol/L) Urine Output, mL/d | <1.2 (110) | 1.2-1.9 (110-170) | 2.0-3.4 (171-299) | 3.5-4.9 (300-440) | >5.0 (440) |

Abbreviations:
$F_{IO2}$, fraction of inspired oxygen;
MAP, mean arterial pressure;
$P_{aO2}$, partial pressure of oxygen
[b]Catecholamine doses are given as μg/kg/min for at least 1 hour.
[c]Glasgow Coma Scale Scores range from 3-15; higher score indicates better neurological function.

Solute Components

Model 1—Demand/Capacity Clinical Points Ratio

In this model, the point scores can be assigned for each component of demand and capacity domains based on clinical rational. Low UO and low GFR can be given lower values (Table 6). SOFA and CFB higher values meaning worst clinical scenario.

The points were added and expressed as a ratio of D/C:

D/C ratio=(NRSOFA+PCFB)/(GFR+UO).

Thus, the D/C ratio ranges from 1-10.

TABLE 6

Points for Demand/Capacity parameters in Model 1.

| Points Demand | SOFA | FB as % BW |
|---|---|---|
| 5 | 0-3 | 0-5% |
| 6 | 4-7 | 5-10% |
| 7 | 8-11 | 10-15% |
| 8 | 12-15 | 15-20% |
| 10 | ≥16 | >20% |

| Points Capacity | eGFR Jelliffe | Urine Volume |
|---|---|---|
| 1 | 0-5 | <100 |
| 2 | 5.1-10 | 100-400 |
| 3 | 10.1-15 | 401-1000 |
| 4 | 15.1-30 | 1001-1500 |
| 5 | >30 | >1500 |

Model 2—D/C Logistic Regression Ratio

In the logistic regression score, points to the parameters given based on the logistic regression model predicting need for dialysis using the UCSD patients in the (see Cohort 3 description in the preliminary results section C below). All four variables were included on a logistic regression model and the relative importance of each of the variables to the whole model was assessed. The method provides a decomposition of the linear regression model variance into non-negative contributors. Ten thousand bootstrap replications were applied to ensure the average results. Relative importance of each contributor was as follow: 35% for non-Renal SOFA (NRSOFA); 30% for GFR; 25% for CFB and 10% for UO. The score was previously defines as a zero-to-ten scale. Therefore, the average importance of each component was stratified on the 0-10 scale, resulting on the following number of points for each component: 3.5 points for NRSOFA, 3 points for GFR, 2.5 points for CFB and 1 point for UO.

Subsequently, the range of each variable was divided in quartiles in order to distribute the point inside the range of each variable. Points were attributed to each quartile taking the coefficient of the logistic regression into account. Visual inspection was also performed of the association between variables and probability of need for dialysis in order to evaluate non-linear associations that could be present. After inspecting the UO component of the score, this variable was stratified in only three strata (and not four using the quartiles), since UO greater than 1 mL/kg/h were not associated with increased need for dialysis and dividing the 0-1 mL/kg/h in more than two parts would make the score more cumbersome and would not improve performance. Therefore, UO was stratified as: bellow 0.5, between 0.5-1.0 and greater than 1.0 mL/kg/h.

Visual inspection also showed that the association between CFB and need for dialysis was non-linear, with an increased risk for patients with negative CFB and lowest risk found for CFB close to zero. Therefore, differently from the other components, which had increasing or decreasing points, points in CFB component were lower for the middle part of the range in order to account for non-linearity. Resulting scores are shown in Table 7. Low UO and low GFR are given lower values. SOFA and CFB higher values meaning worst clinical scenario. Uses sum of the parameters points prior to computing the ratio. Range is 0.1 to 10.

TABLE 7

Points for Demand/Capacity parameters in Model 2.

| Value | Points | Value | Points |
|---|---|---|---|
| Urinary Output | | NRSOFA | |
| <0.5 mL/kg/h | 1 | ≤2 | 0 |
| ≥0.5 and <1 mL/kg/h | 0.5 | >2 and ≤5 | 1 |
| ≥1 mL/kg/h | 0 | >5 and ≤8 | 2 |
|  |  | >8 | 3.5 |
| GFR | | CFB | |
| ≤20 | 3 | <0% | 0 |
| >20 and ≤30 | 2 | >0 and ≤2.5% | 0.5 |
| >30 and ≤50 | 1 | >2.5 and ≤5% | 0 |
| >50 | 0 | >5% | 1 |

Model 3—D/C Logistic Additive Ratio

In the additive models, points were given to parameters based on the logistic regression done for Model 2, without adjusting for the relative importance of each of the variables. The sum of demand and capacity parameters was used to derive the score, where low UO and low GFR are given higher values and SOFA and CFB higher values meaning worst clinical scenario. The calculation is:

$a$D/C=NRSOFA+PCFB+GFR+UO and the scores range from 1-9 (see Table 8).

TABLE 8

Points for Demand/Capacity parameters in Model 3.

| Value | Points | Value | Points |
|---|---|---|---|
| Urinary Output | | NRSOFA | |
| ≤0.4 mL/kg/h | 1 | 0-5 | 0 |
|  |  | 5-10 | 1.5 |
| >4 mL/kg/h | 0 | >10 | 2.5 |
| GFR | | CFB | |
| ≤10 | 4 | <5% | 0 |
| >10 and <20 | 3 | >0 and ≤10% | 1 |
| >20 and <30 | 2 | >10% | 1.5 |
| ≥30 | 0 |  |  |

Model 4—D/C Clinical Index Product Ratio

Utilizing the same points derived from Model 1, the product of demand and capacity was applied and divided to create a ratio. The equation is:

$p$D/C=(NRSOFA*PCFB)/(GFR*UO).

Model 5—D/C Logistic Product Ratio

Utilizing the same points from the logistic regression of model 2, the product of demand and capacity was applied and divided to create a ratio. The equation is:

$p$D/C_Ir=(NRSOFA*PCFB)/(GFR*UO).

TABLE 9

Summary of Clinical Index Models

| Model | Characteristics | Calculation | Range |
|---|---|---|---|
| 1-D/C clinical points ratio | Give points to parameters based on clinical status Uses sum of demand and capacity parameters and divide them creating a ratio | D/C = (NRSOFA + PCFB)/(GFR + UO) | 0.1-20 |
| 2-D/C logistic ratio | Give points to parameters based on the logistic regression of demand capacity components Uses sum of the parameters points and express as a ratio | D/C_lr = (NRSOFA + PCFB)/(GFR + UO) | 0.1-10 |
| 3-D/C logistic additive ratio | Assign points to parameters based on the logistic regression of demand capacity components Uses sum of the parameters points as a score | aD/C = NRSOFA + PCFB + GFR + UO | 1-9 |
| 4-D/C clinical index product ratio | Give points to parameters based on clinical status Uses product of demand and capacity points and divide them creating a ratio | pD/C = (NRSOFA * PCFB)/(GFR * UO) | 1-100 |
| 5-D/C logistic product ratio | Give points to parameters based on the logistic regression of demand capacity components Uses product of demand and capacity parameters and divide them creating a ratio | pD/C_lr = (NRSOFA * PCFB)/(GFR * UO) | 0.025 to 72 |

In some embodiments, methods of treating an organ system dysfunction or an organ system disease in a subject in need thereof can include administering continuous organ system replacement therapy to the subject. In some embodiments, the subject has a clinical Index (CI) value of at least about 1.0 (e.g., at least about 1.5, e.g., at least about 1.8, e.g., at least about 1.9, e.g., at least about 2.0, e.g., at least about 2.5), about 1.0 to about 1.5, about 1.5 to about 1.8, or about 1.5 to about 1.9, wherein the CI value is determined using an algorithm.

In some embodiments, methods for initiating continuous organ system replacement therapy in a subject in need thereof can include administering continuous organ system replacement therapy to the subject if the subject has a Clinical Index (CI) value of at least about 1.0 (e.g., at least about 1.5, e.g., at least about 1.8, e.g., at least about 1.9, e.g., at least about 2.0, e.g., at least about 2.5), about 1.0 to about 1.5, about 1.5 to about 1.8, or about 1.5 to about 1.9, wherein the CI value is determined using an algorithm.

A method of treating acute kidney injury (AKI) in a subject in need thereof, comprising administering continuous renal replacement therapy (CRRT) to the subject, wherein the subject has a Clinical Index (CI) value of at least about 1.0 (e.g., at least about 1.5, e.g., at least about 1.8, e.g., at least about 1.9, e.g., at least about 2.0, e.g., at least about 2.5), about 1.0 to about 1.5, about 1.5 to about 1.8, or about 1.5 to about 1.9, wherein the CI value is determined by an algorithm.

A method for initiating continuous renal replacement therapy (CRRT) in a subject in need thereof, comprising administering continuous renal replacement therapy (CRRT) to the subject if the subject has a Clinical Index (CI) value of at least about 1.0 (e.g., at least about 1.5, e.g., at least about 1.8, e.g., at least about 1.9, e.g., at least about 2.0, e.g., at least about 2.5), about 1.0 to about 1.5, about 1.5 to about 1.8, or about 1.5 to about 1.9, wherein the CI value is determined by an algorithm.

An organ system dysfunction monitoring device or system can include a display screen; and one or more processing units configured to receive one or more parameters. In some embodiments, the one or more parameters can include a SOFA parameter, a PCFB parameter, a GFR parameter, a UO parameter, or a combination thereof.

In some embodiments, the SOFA parameter is the sepsis-related sequential organ failure assessment score parameter of a patient with an organ system dysfunction. In some embodiments, the PCFB parameter is a cumulative fluid balance parameter of the patient. In some embodiments, the GFR is a glomerular filtration rate parameter of the patient. In some embodiments, the UO parameter is a urinary output parameter of the patient.

In some embodiments, the monitor generates a clinical index (CI) value by processing the SOFA parameter, the PCFB parameter, the GFR parameter, and/or the UO parameter using an algorithm.

In some embodiments, the monitor displays the generated CI value on the display screen.

In one embodiment, the algorithm is a ratio of [(SOFA+PCFB)/(GFR+UO)]; wherein points to the SOFA, PCFB, GFR, and UO parameters are based on clinical status.

In one embodiment, the algorithm is a ratio of [(NRSOFA+PCFB)/(GFR+UO)]; wherein points to the NRSOFA, PCFB, GFR, and UO parameters are based on clinical status.

In one embodiment, the algorithm is a sum of [SOFA+PCFB+GFR+UO]; wherein points to the SOFA, PCFB, GFR, and UO parameters are based on the logistic regression of demand capacity components.

In one embodiment, the algorithm is a sum of [NRSOFA+PCFB+GFR+UO]; wherein points to the NRSOFA, PCFB, GFR, and UO parameters are based on the logistic regression of demand capacity components.

In one embodiment, the algorithm is a ratio of [(SOFA*PCFB)/(GFR*UO)]; wherein points to the SOFA, PCFB, GFR, and UO parameters are based on clinical status.

In one embodiment, the algorithm is a ratio of [(NRSOFA*PCFB)/(GFR*UO)]; wherein points to the NRSOFA, PCFB, GFR, and UO parameters are based on clinical status.

In one embodiment, the algorithm is a ratio of [(SOFA*PCFB)/(GFR*UO)]; wherein points to the SOFA, PCFB, GFR, and UO parameters are based on the logistic regression of demand capacity components.

In one embodiment, the algorithm is a ratio of [(NRSOFA*PCFB)/(GFR*UO)]; wherein points to the NRSOFA, PCFB, GFR, and UO parameters are based on the logistic regression of demand capacity components.

In some embodiments, the SOFA is a sepsis-related sequential organ failure assessment score of the patient, PCFB is a cumulative fluid balance of the patient, GFR is a glomerular filtration rate of the patient, and/or UO is a urinary output of the patient. In some embodiments, the SOFA a non-renal SOFA (NRSOFA).

An acute kidney injury monitoring device or system can include a display screen; and one or more processing units configured to receive one or more parameters. In some embodiments, the one or more parameters can include a NRSOFA parameter, a PCFB parameter, a GFR parameter, a UO parameter, or a combination thereof.

In some embodiments, the NRSOFA parameter is the non-renal sepsis-related sequential organ failure assessment score parameter of a patient with an acute kidney injury. In some embodiments, the PCFB parameter is a cumulative fluid balance parameter of the patient. In some embodiments, the GFR is a glomerular filtration rate parameter of the patient. In some embodiments, the UO parameter is a urinary output parameter of the patient.

In some embodiments, the monitor generates a clinical index (CI) value by processing the NRSOFA parameter, the PCFB parameter, the GFR parameter, and/or the UO parameter using an algorithm.

In some embodiments, the monitor displays the generated CI value on the display screen.

In some embodiments, the devices, systems, and methods described herein can represent a simple tool set to improve clinical care. In some embodiments, data can be automatically updated within a device or system and provide a physician with an up to date therapy/intervention recommendations based on calculations described herein. In some embodiments, therapy/intervention is automatically provided by a device or system.

In some embodiments, the devices, systems, and methods described herein can track effects of interventions and assist in defining next steps. In some embodiments, as index changes, if goals are being achieved, prognostic information can be provided on organ performance based on alterations in biomarker profile and clinical criteria.

In some embodiments, the devices, systems, and methods described herein can be used to monitor patients through continuum of care i.e. from ICU to hospital ward to outpatient based on sensor technology to capture the pertinent information.

In some embodiments, devices can perform the algorithms and methods described herein. Devices can attain inputs from various organ assessment instruments. These inputs can be programmed manually by an individual or can be programmed automatically by a system(s).

Figure 8:
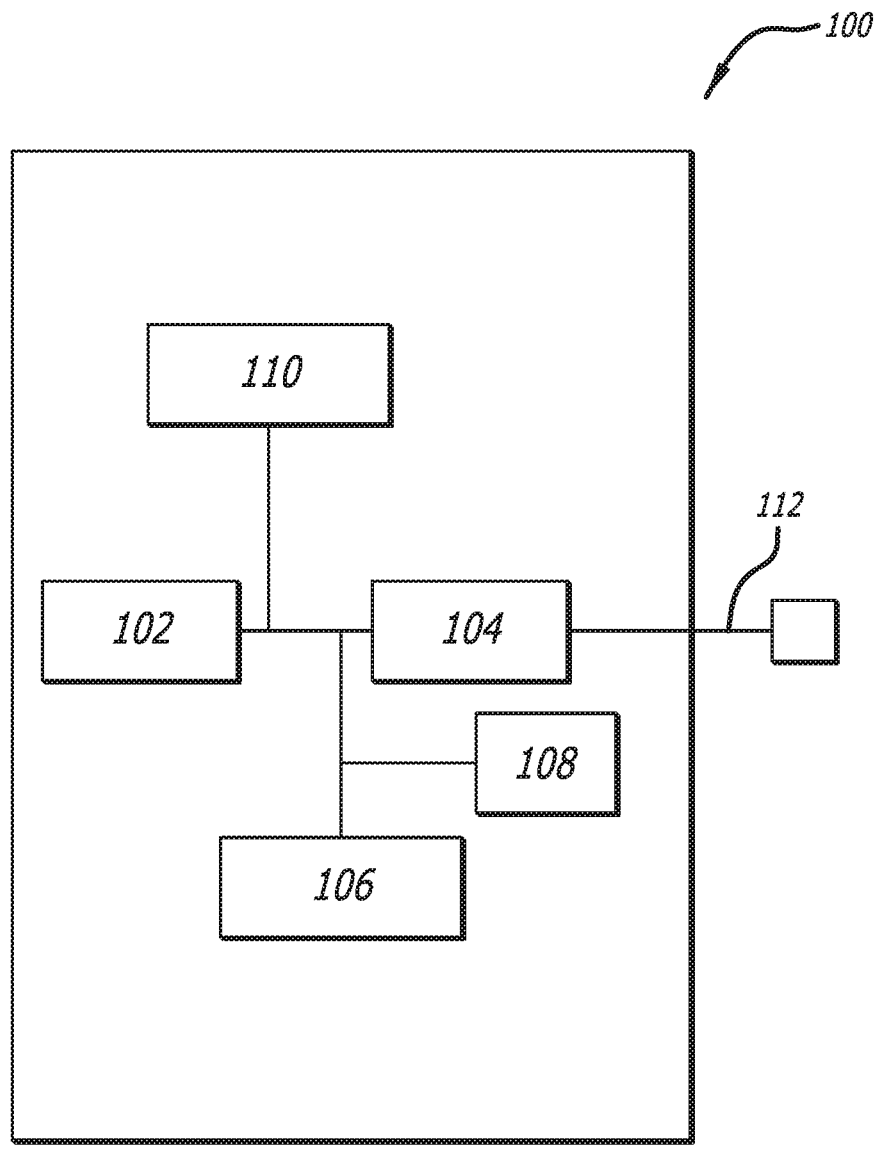
FIG. 8 illustrates a block diagram of a device as described herein.
Figure 9A:
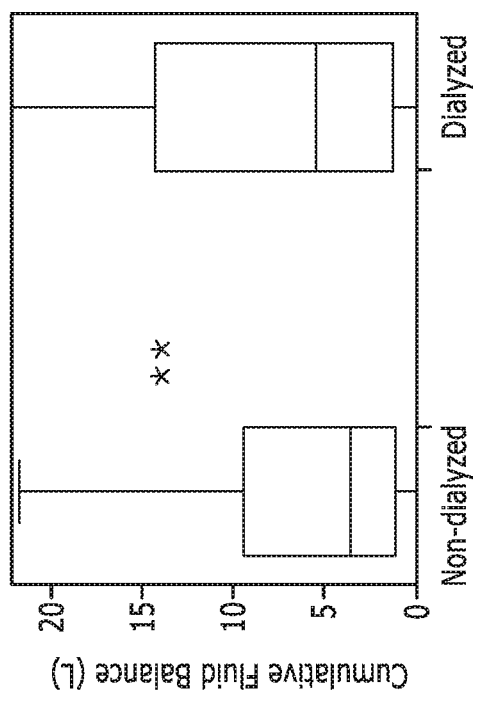
FIG. 9 illustrates demand and capacity parameters on day of peak sCr, Non-renal SOFA (A); cumulative fluid balance (B); eGFR (C) and UO (D) in dialyzed and non-dialyzed patients in Cohort 1.
Figure 9B:
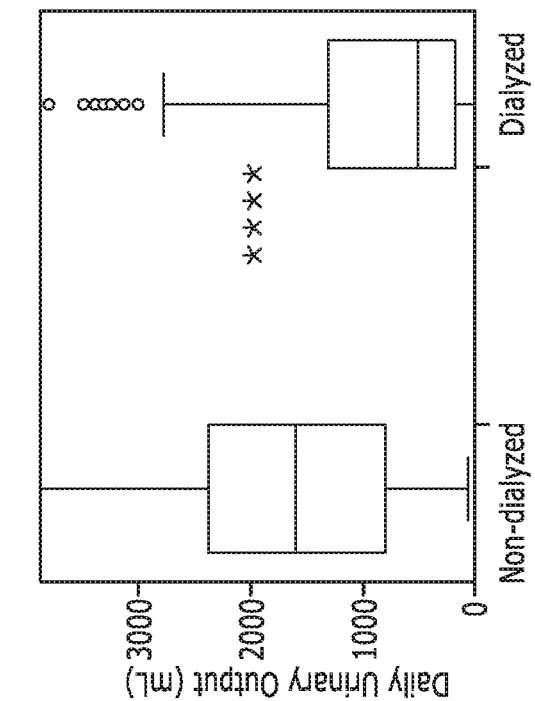
Figure 9C:
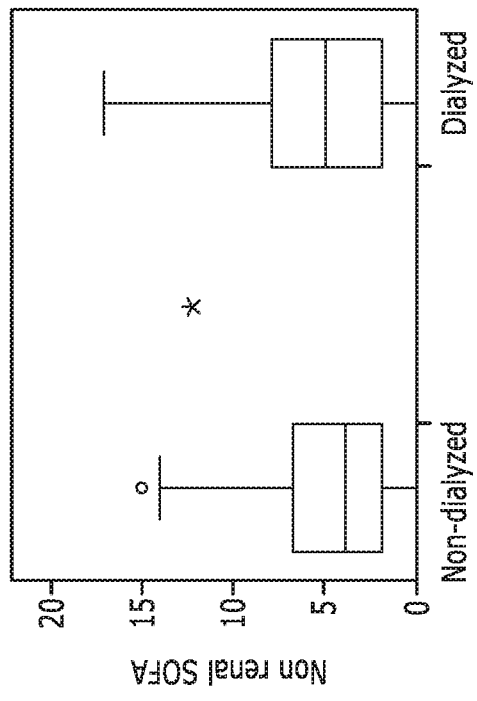
Figure 9D:
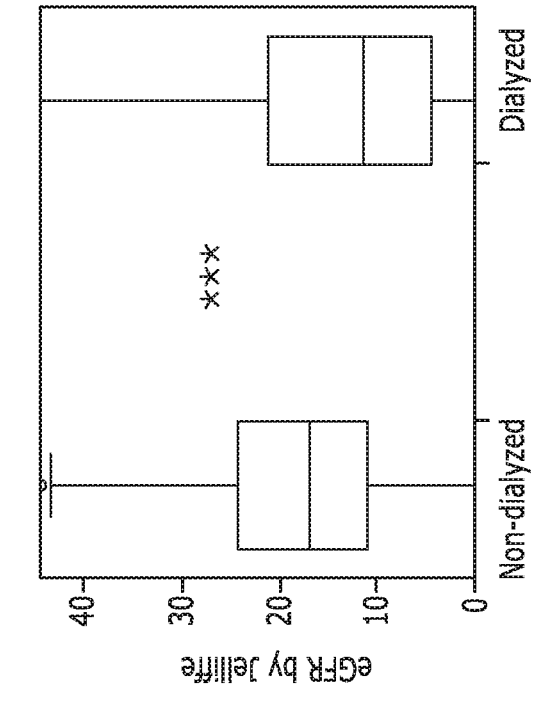

In one embodiment illustrated in FIG. 8, devices can include an algorithm(s) stored in memory 102 and executed by a processor(s) 104 in a computing device 100 such as but not limited to a cellular phone, a personal digital assistant, a laptop computer, a tablet computer, or a smart phone.

In other embodiments, the computing device can be a custom built device that includes memory 102, a processor(s) 104, an input device 106, and an indicator(s) 108. In some embodiments, the device can include a screen 110.

A device can interact with a large number of users at a plurality of different measuring and/or diagnostic systems. Accordingly, the devices can include one or more network connections 112. In some embodiments, the one or more network connections 112 can be wired and/or wireless. Conversely, a device may include memory, a processor, and a single network connection.

In some embodiments, a network connection can be to infrastructure that interfaces with organ support systems. In some embodiments, the devices can interface with organ support systems to initiate, terminate increase, or decrease a particular therapy. In some embodiments, this intervention can be automatic. In other embodiments, this intervention can be manually performed or instructed by, for example, a physician.

It should be appreciated that device users may include any person or entity which uses the presently disclosed devices and may include a wide variety of parties. In some embodiments, the users may refer to various different entities, including patients, physicians, administrative users, mobile device users, private individuals, and/or commercial partners.

In one embodiment, devices may include at least one processor 104 electrically connected by an address/data bus 114 to memory 102 or at least one memory device, other computer circuitry, and at least one interface circuit. The processor may be any suitable processor, such as a microprocessor from the INTEL®, AMD®, NVIDIA®, BROADCOM®, MARVEL®, ORACLE CORPORATION®, IBM®, APPLE®, ALTERA®, APOLLO®, ARM®, ATMEL®, DATA GENERAL®, SONY®, TOSHIBA®, FREESCALE SEMICONDUCTOR®, GOOGLE®, HITACHI®, MIPS TECHNOLOGIES®, NATIONAL SEMICONDUCTORS, NEC®, RCA®, TEXAS INSTRUMENTS®, VIA®, WESTERN DIGITAL®, or the like. The processor may include one or more microprocessors, central processing units (CPUs), computing devices, microcontrollers, digital signal processors, or like devices or any combination thereof. Memory includes volatile memory and non-volatile memory. In some embodiments, memory stores algorithm(s) that interact with the other devices in system as described herein. Memory may also store digital data indicative of documents, files, programs, web pages, etc. retrieved from measuring and/or diagnostic systems and/or loaded via an input device.

Input device 106 may be at least one of a keyboard, mouse, touch screen, track pad, track ball, isopoint, image sensor, character recognition, barcode scanner, and a voice recognition system.

Indicator 108 can be a light or lights that indicate a status of the device based on an algorithm result. For example, an algorithm result that includes a high D/C ratio may display a red indicator. Conversely, an algorithm result that includes a low D/C ratio may display a green indicator. In some embodiments, an algorithm result that includes a high D/C ratio may display a color indicator other than green or red. Any combination of colors can be used.

Screen 110 may be a cathode ray tube (CRTs), a liquid crystal display (LCD), a light emitting diode (LED) display, an organic LED (OLED) display, or any other suitable type of display device. The screen may be configured to generate visual displays during operation of the device. A user interface may be displayed on the screen and include prompts for human input from a user including links, buttons, tabs, checkboxes, thumbnails, text fields, drop down boxes, etc., and may provide various outputs in response to the user inputs, such as text, still images, videos, audio, and animations.

In some embodiments, the devices, systems, and methods described herein can include data extraction/integration tools to source data from EHR and/or other clinical systems. Such tools can have robust security to be compliant with HIPAA and any other applicable standards. The tools can include predictive analytics algorithms to parse relevant data and determine recommended approach. Further still, the tools can include a presentation layer that can present relevant information and system recommendations to the physician (e.g., nephrologist) as decision support data, with ability to optionally focus on relevant supporting detail. The presentation layer can include a virtual dashboard that presents system recommendations as well as allows for some basic "what if" type analysis that the doctor can use to simulate anticipated outcomes.

In some embodiments, the devices, systems, and methods described herein can be deployed as a web based application for bedside usages, as well as a smartphone/tablet deployed version aimed at kidney care professionals. In some embodiments, over time, extensive benchmarks may become available by aggregating data over all patients in the system; a platform of the best options for patient care can be created and continually refined (feedback loop); a link to a database of comparative benchmark data can be provided that can be assessed on-demand to support decision making; and/or a link to relevant research can be provided that can provide greater insight to support the recommended actions.

In some embodiments, the devices, systems, and methods described herein can be applied to platforms that can be applied to define timing of intervention for other organ systems. Other organ systems can include, but are not limited to lung support with ventilator, heart failure support with ventricular assist devices, liver support with extracorporeal liver support devices, and Hematological and immunological support with Apheresis techniques.

In some embodiments, the devices, systems, and methods described can determine a D/C ratio that represents an imbalance between organ function and a patient's demand.

In some embodiments, the devices, systems, and methods described can calculate D/C ratio scores in multiple ways and predict organ support need.

In some embodiments, the D/C ratio is a dynamic parameter that progressively increases in AKI patients who need intervention and correlates with organ support need, mortality and composite outcome adverse outcomes.

In some embodiments, the devices, systems, and methods described can assess, calculate, and/or determine hinge points in D/C ratio scores that correlate with outcomes to establish a lower boundary below which high likelihood of survival and recovery without organ support, an upper boundary above which high likelihood of death with or without organ support or non-recovery, or both.

In some embodiments, the devices, systems, and methods described can assist a physician's decisions for initiating organ support. These decisions can be influenced by a combination of clinical factors, perceived severity of illness, likelihood of benefit, and logistic factors. The D/C ratio can discriminate well and may reduce uncertainty by a quantitative assessment of clinical and process of care factors that influence the decision.

In some embodiments, sequential assessment of CI allows evaluation of timing of organ support initiation using patient's characteristics as a parameter.

In some embodiments, the devices, systems, and methods described can use a D/C ratio to compare center and physician patterns regarding organ support initiation and modality choice.

In some embodiments, the devices, systems, and methods described can calculate D/C ratio scores based on simple clinical parameters that are routinely assessed in ICU. In some embodiments, these clinical parameters can be incorporated in EMR for an alert system and combined with a risk score for identifying high risk for organ damage and/or failure.

In some embodiments, the demand capacity imbalance quantification can be used for informing timing of intervention, adjustments in dose of organ support, transitions in therapy modality, and/or stopping organ support for efficacy and futility.

Example 1

Our studies utilized three resources; the PICARD study database, an ongoing multicenter Registry of AKI in ICU patients and data from UCSD ICU patients.

Cohort Description

Cohort 1 Project to Improve Care in Acute Renal Disease (PICARD) Study Database

The PICARD prospective observational study enrolled 618 critically-ill patients who underwent a nephrology consultation for AKI in the ICU at 5 academic medical centers in North America over a 30 month period. AKI was defined as an increase in sCr≥0.5 mg if baseline sCr was <1.5 or an increase in sCr≥1.0 if baseline was 1.5 and <5.0 mg/dl. Patients were followed through their hospital discharge or death. Detailed clinical and lab data including fluid intake and output and fluid balance, severity of illness (SOFA and Apache III) and sepsis status were recorded daily. Details of process of care including medications and RRT procedures and outcomes were recorded. This rich database has been utilized to develop the initial CI models.

Cohort 2 International AKI Registry

Over the last 10 years we have conducted a prospective multicenter, international Registry of patients with AKI in the ICU. Patients are screened at admission to ICU and up to 7 days following ICU admission. Patients who meet the AKIN criteria for AKI (SCr increase>0.3 mg/dL within a 48 hr interval) are consented for enrollment and data captured in a web-based database supported by the O'Brien Center in San Diego. Patients are followed through their ICU stay and, if dialyzed, details of the RRT procedures are recorded. Similar to the PICARD database, the Registry includes detailed information on co-morbidities, risk factors for AKI, clinical and lab data, fluid balance status, severity of illness scores and outcomes through hospital discharge (Table 10).

TABLE 10

Number of patients in the registry cohort with data for D/C calculation by region.

|  | North America | Asia | South America | Total |
| --- | --- | --- | --- | --- |
| −48 h | 78 | 29 | 26 | 133 |
| −24 h | 132 | 43 | 40 | 215 |
| day of dialysis initiation | 240 | 68 | 73 | 381 |

TABLE 10-continued

Number of patients in the registry cohort with data for D/C calculation by region.

|  | North America | Asia | South America | Total |
|---|---|---|---|---|
| +24 h | 196 | 50 | 56 | 302 |
| +48 h | 159 | 49 | 50 | 258 |

We analyzed 381 patients with AKI from 5 international centers with complete data to allow the computation of one or more days of CI values. As in the PICARD cohort, the Demand and Capacity parameters were calculated sequentially utilizing the day of peak sCr (in all patients) and day of RRT (in dialyzed patients) as reference points to ascertain the progressive change in the demand and capacity parameters. The peak sCr was used as an indicator of the worst level of renal function.

Of the 338 patients, 11% were dialyzed during the observation period. The in-hospital mortality rate was 24% (dialyzed: 53% vs. non-dialyzed: 20%; p<0.001). In contrast with the PICARD cohort that only included AKI patients with nephrology consultation, the Registry cohort uses a more sensitive AKI definition (AKIN criteria), and includes patients with a broader AKI spectrum. In the Registry cohort, with a wider range of AKI severity, the differences in CI was even greater between dialyzed and non-dialyzed patients and a better predictor of the need for RRT on the day of peak sCr. Additionally, in the Registry data, changes in the CI ratio were computed from AKI diagnosis and hence could be used to define an intervention point.

Cohort 3 UCSD ICU Cohort

In order to validate the findings from the PICARD and AKI registry cohorts, we analyzed data from 1269 ICU patients admitted from May to July 2014 at UCSD Hillcrest Medical center. Sixteen percent of patients developed AKI during ICU stay and 7% were dialyzed. In this cohort we assessed the progression of CI of all patients during the ICU stay, and compared the progression of the clinical index between dialyzed and non-dialyzed patients.

Cohort 4 UCSD ICU Cohort

In order to validate the findings from the previous UCSD cohort 3, the cohort was increased to include patients from Jan. 1, 2014 to Nov. 30, 2016 and patients from a center in Muenster, Germany. Cohort 4 had 11,440 encounters from 10,258 patients with complete information to calculate D/C ratios. A total of 923 patients (9%) were dialyzed and 8.1% died during hospitalization. As in Cohort 3, the progression of CI of all patients was assessed during the ICU stay, and compared the progression of the clinical index between dialyzed and non-dialyzed patients.

The Cohort 4 risk score is multiplied by 10.

Proof of Concept Data

The Components Used in Calculation of D/C Ratio are Related to Actual Utilization of Dialysis The Demand and Capacity parameters were calculated on day of peak sCr (in all patients) and day of RRT (in dialyzed patients). The peak sCr was used as an indicator of the worst level of renal function. There were significant differences in the individual components in dialyzed and non-dialyzed patients. At day of peak sCr, demand parameters were higher and capacity parameters were lower in patients that needed RRT (FIG. 9A-D) (Cohort 1). These findings were replicated in Cohort 3 with increases in the non-renal SOFA score and the amount of fluid accumulation (Demand parameters) and decreased urine output and fluid adjusted GFR (Capacity parameters) were associated with the need for dialysis (FIG. 10A-D).

Figure 11:
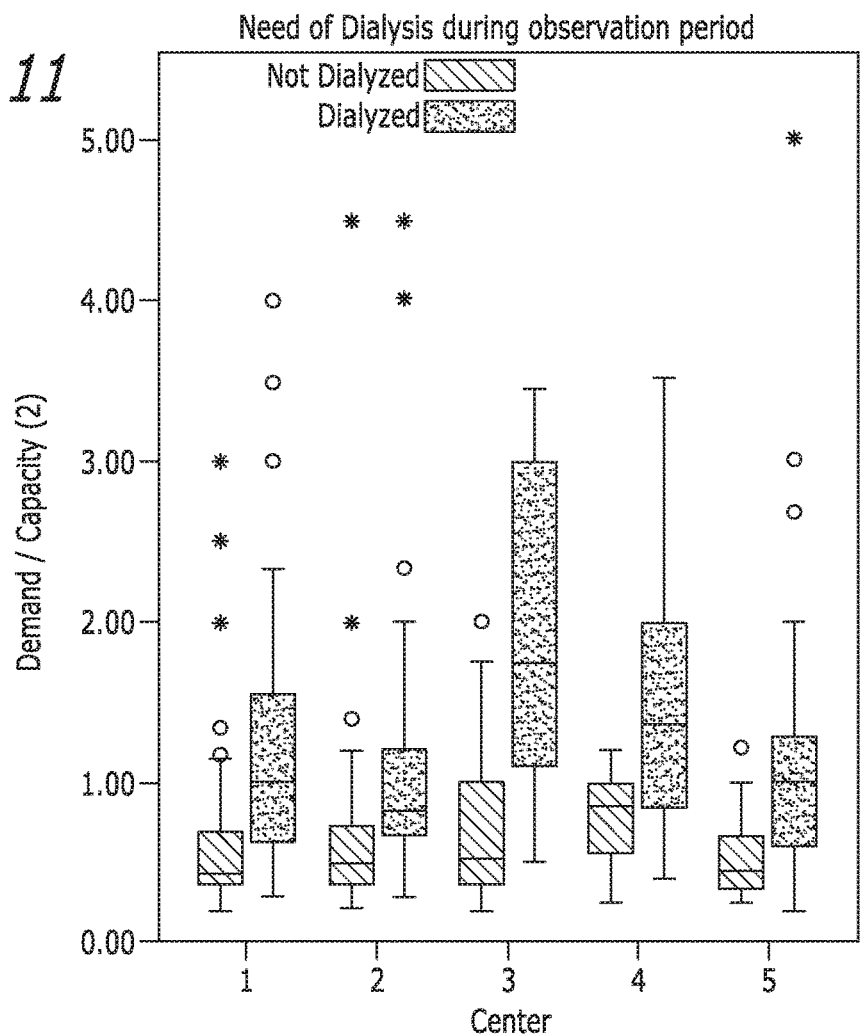
FIG. 11 illustrates D/C ratio across different centers.
Figure 12:
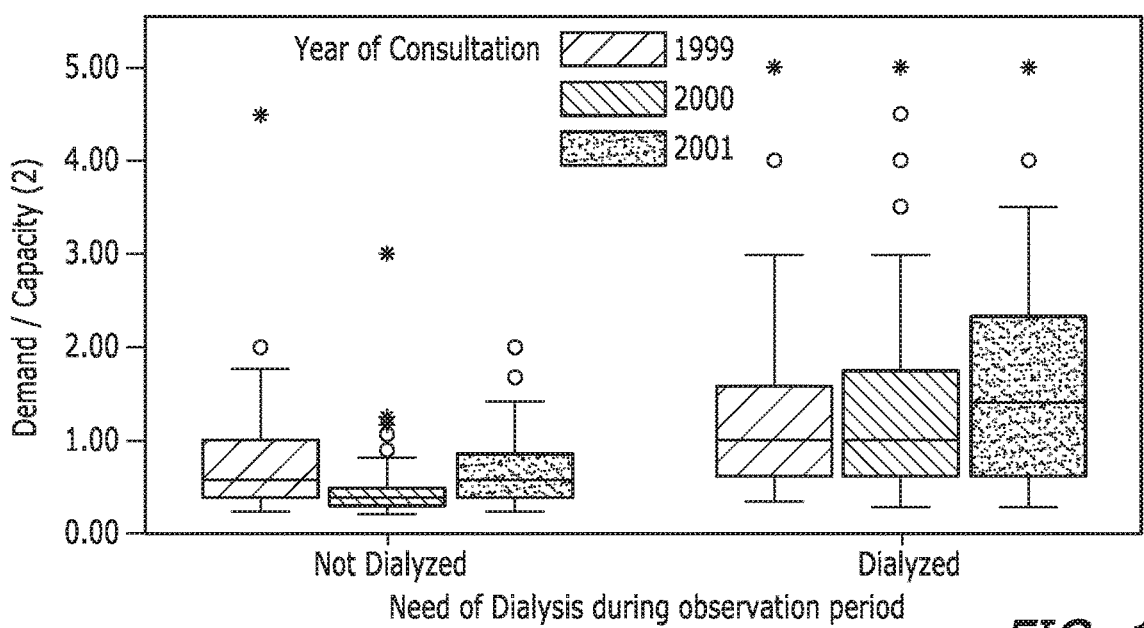
FIG. 12 illustrates a box plot of D/C ratios across the study years (Cohort 1).

The Demand Capacity Mismatch can be Quantified and Predicts Dialysis Utilization On the day of peak sCr the D/C ratios were significantly different in dialyzed and non-dialyzed patients (Cohort 1) (FIG. 11). These differences were seen across all 5 centers in the cohort and were similar across the 3 years of the study (FIG. 12) showing that the parameters are replicable.

Figure 13:
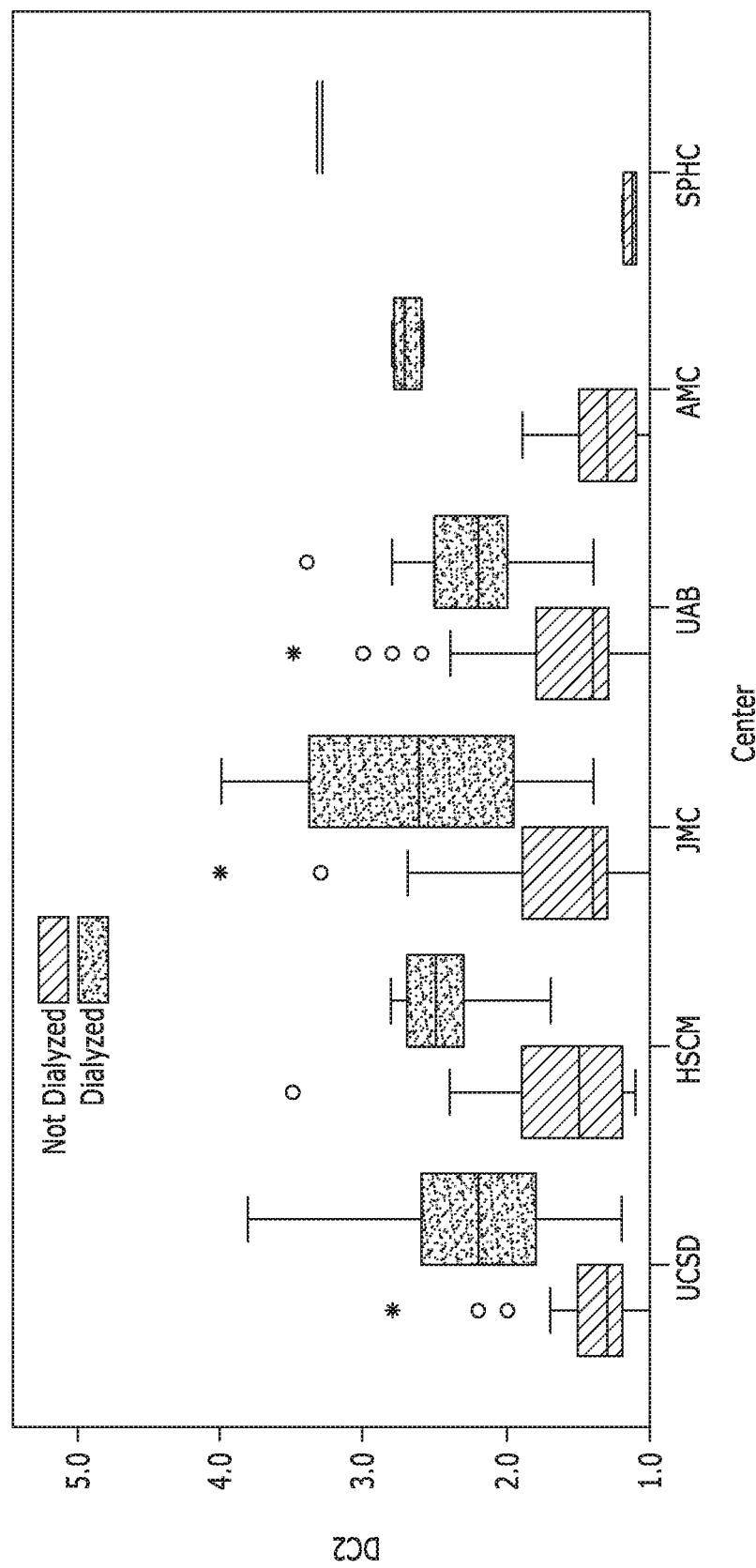
FIG. 13 illustrates the ratio at dialysis initiation or day of peak serum creatinine across different centers in North America (Cohort 2).
Figure 14:
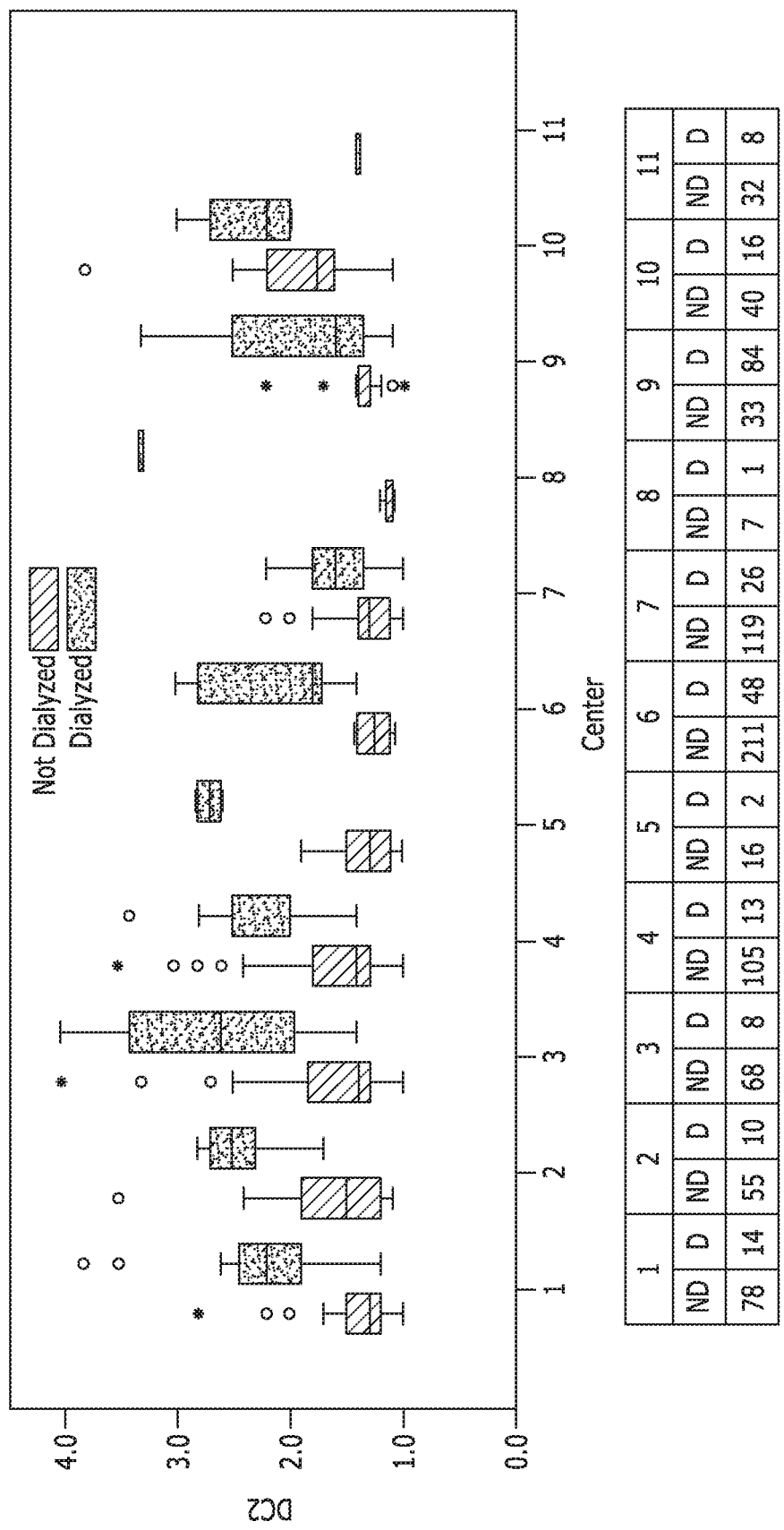
FIG. 14 illustrates D/C at dialysis initiation or day of peak serum creatinine across international centers (Cohort 2).
Figure 17B:
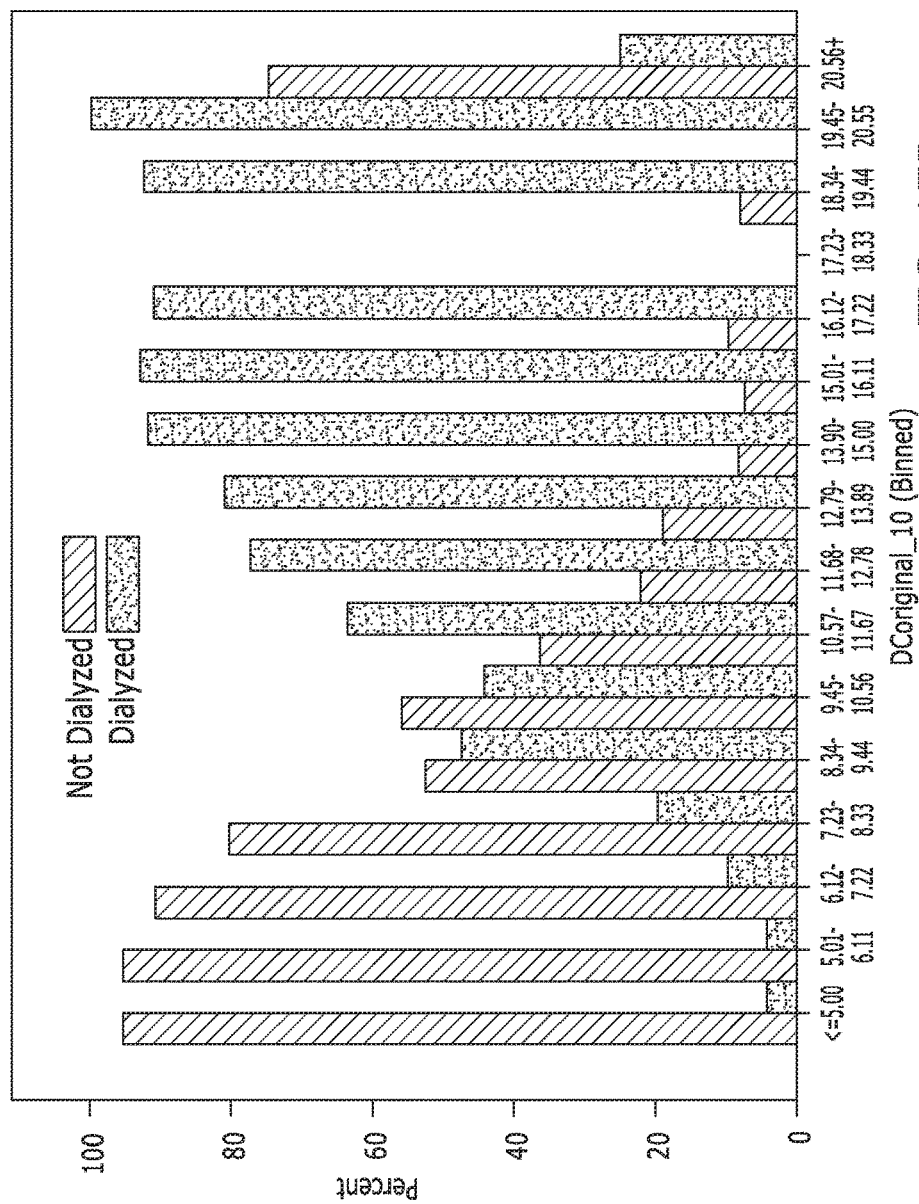
FIGS. 17A and 17B illustrate distribution of D/C ratios on day of dialysis or peak serum creatinine.
Figure 17A:
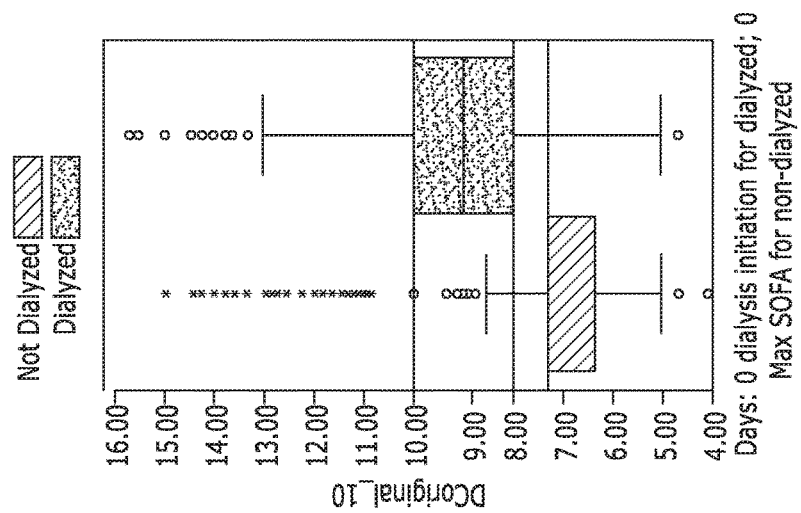

The differences in D/C ratios among dialyzed and non-dialyzed patients was similarly seen across centers in the USA and internationally in Cohort 2 (FIG. 13 and FIG. 14).

Similar results were obtained in patients across different regions (FIG. 15). Non-dialyzed patients have lower D/C ratio and a tighter distribution than non-dialyzed patients (FIGS. 16A-B and 17A-B).

Figure 18:
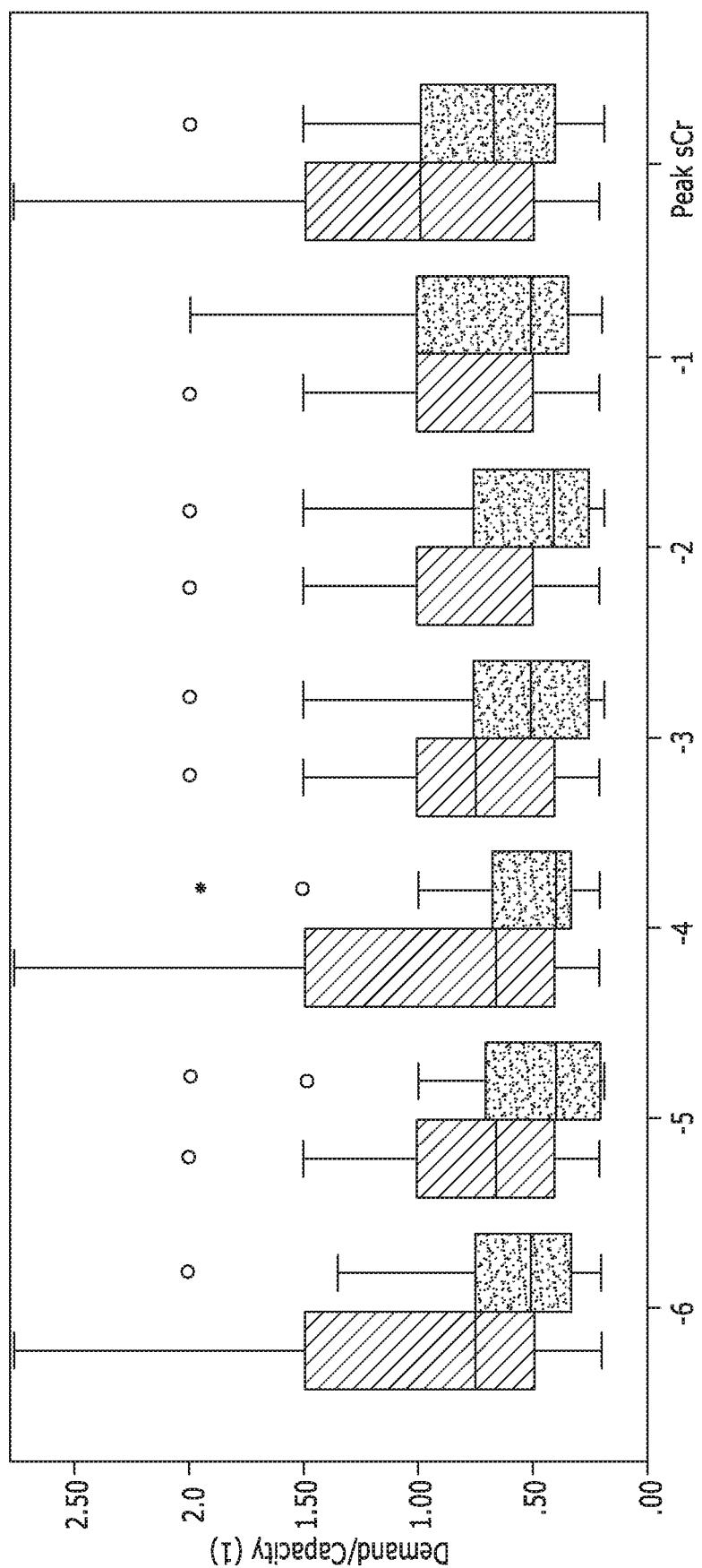
FIG. 18 illustrates progression of D/C ratio until day of peak serum creatinine in dialyzed and non-dialyzed patients (Cohort 1).

The Demand Capacity Mismatch can be Dynamically Monitored and its Progression is Associated with Dialysis Need and the Modality Used In Cohort 1 and Cohort 2, we calculated the Demand and Capacity parameters sequentially utilizing the day of peak sCr (in all patients) and day of RRT (in dialyzed patients) as reference points to ascertain the progressive change. The D/C ratio progressively increased to the peal serum creatinine in patients who were ultimately dialyzed and remained stable or decreased in non-dialyzed patients (FIG. 18).

Figure 19:
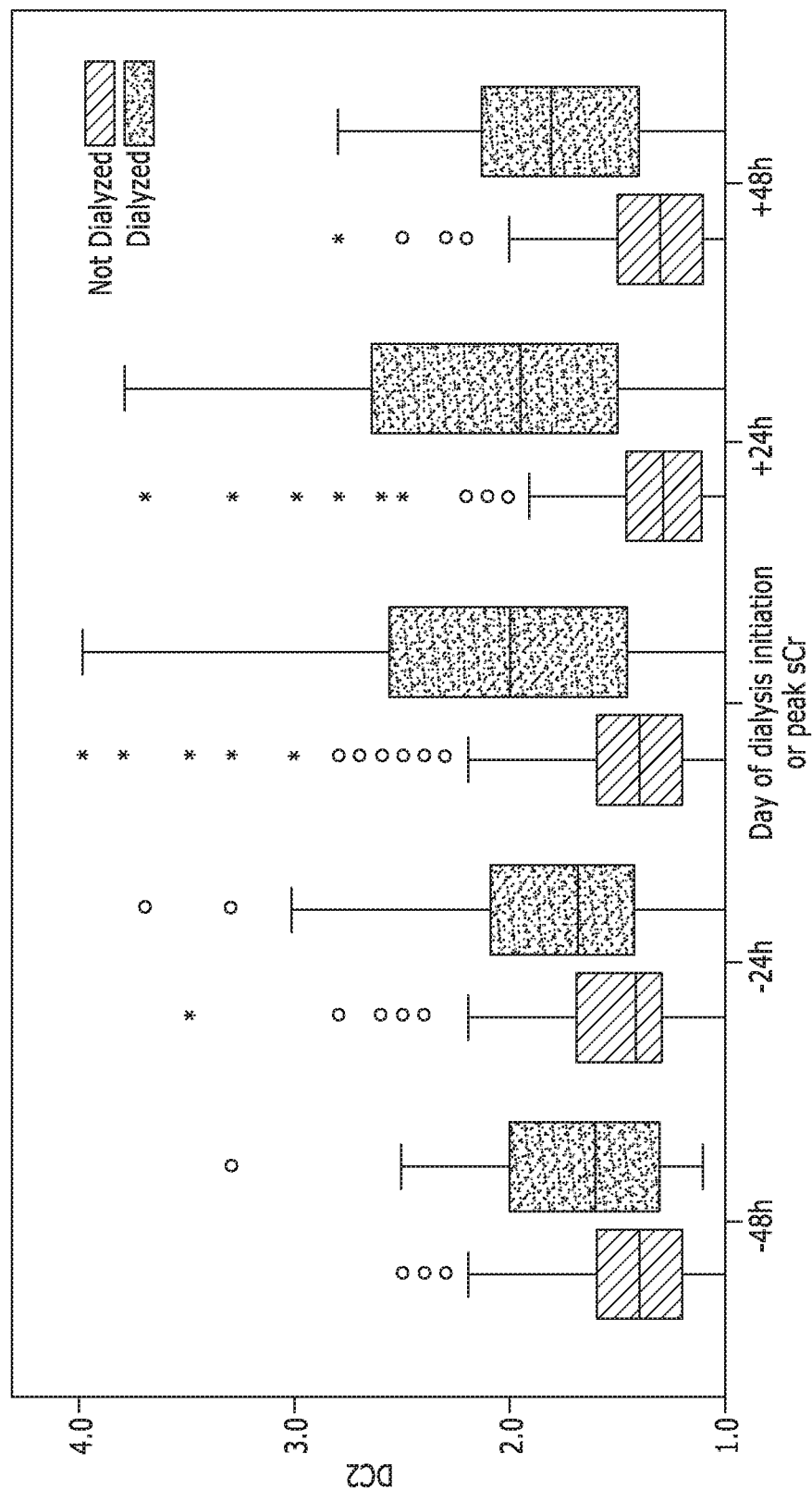
FIG. 19 illustrates progression of clinical index in dialyzed vs non-dialyzed patients using the dialysis initiation or day of peak serum creatinine as reference time point (Cohort 2).
Figure 20:
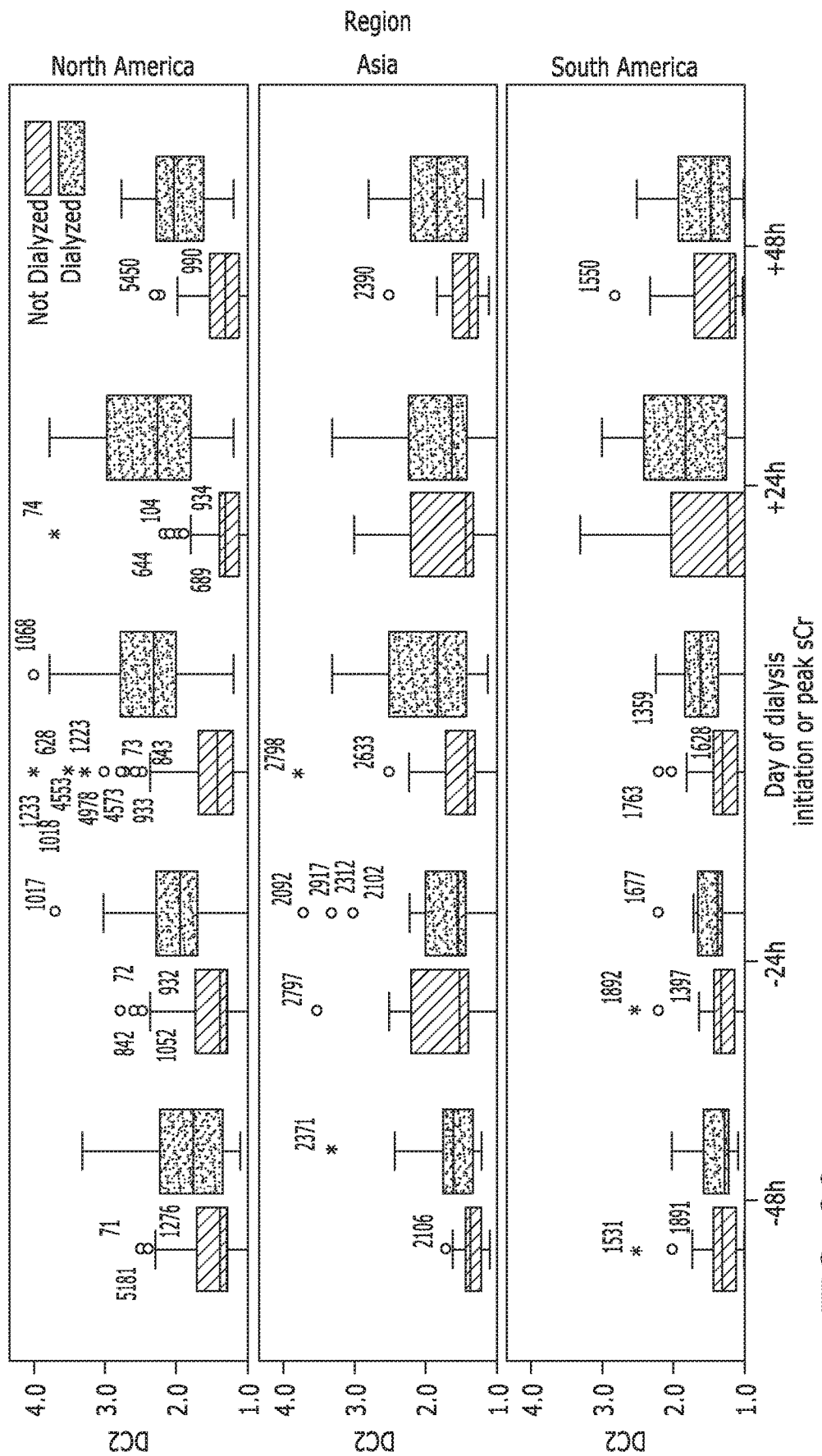
FIG. 20 illustrates progression of D/C ratio in different regions (Cohort 2).

When tracked for 48 hrs before to 48 hrs after the peak serum creatinine or initiation of dialysis, the non-dialyzed and dialyzed patients showed different trajectories of the D/C ratio (FIG. 19, Cohort 2) that were seen across all regions (FIG. 20, Cohort 2).

Figure 21:
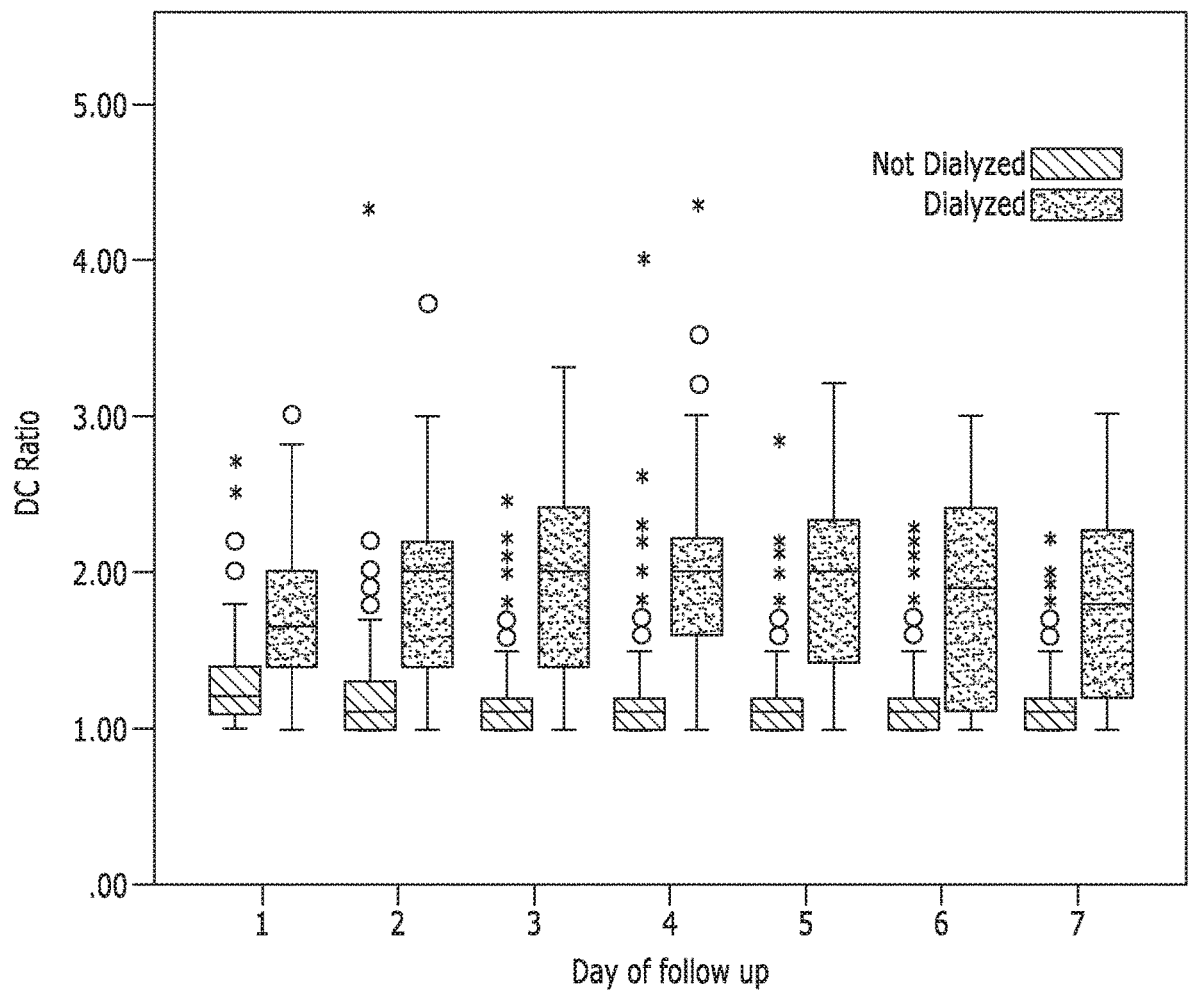
FIG. 21 illustrates progression of D/C ratio in dialyzed and non-dialyzed patients during first 7 days of ICU stay (Cohort 3).
Figure 22:
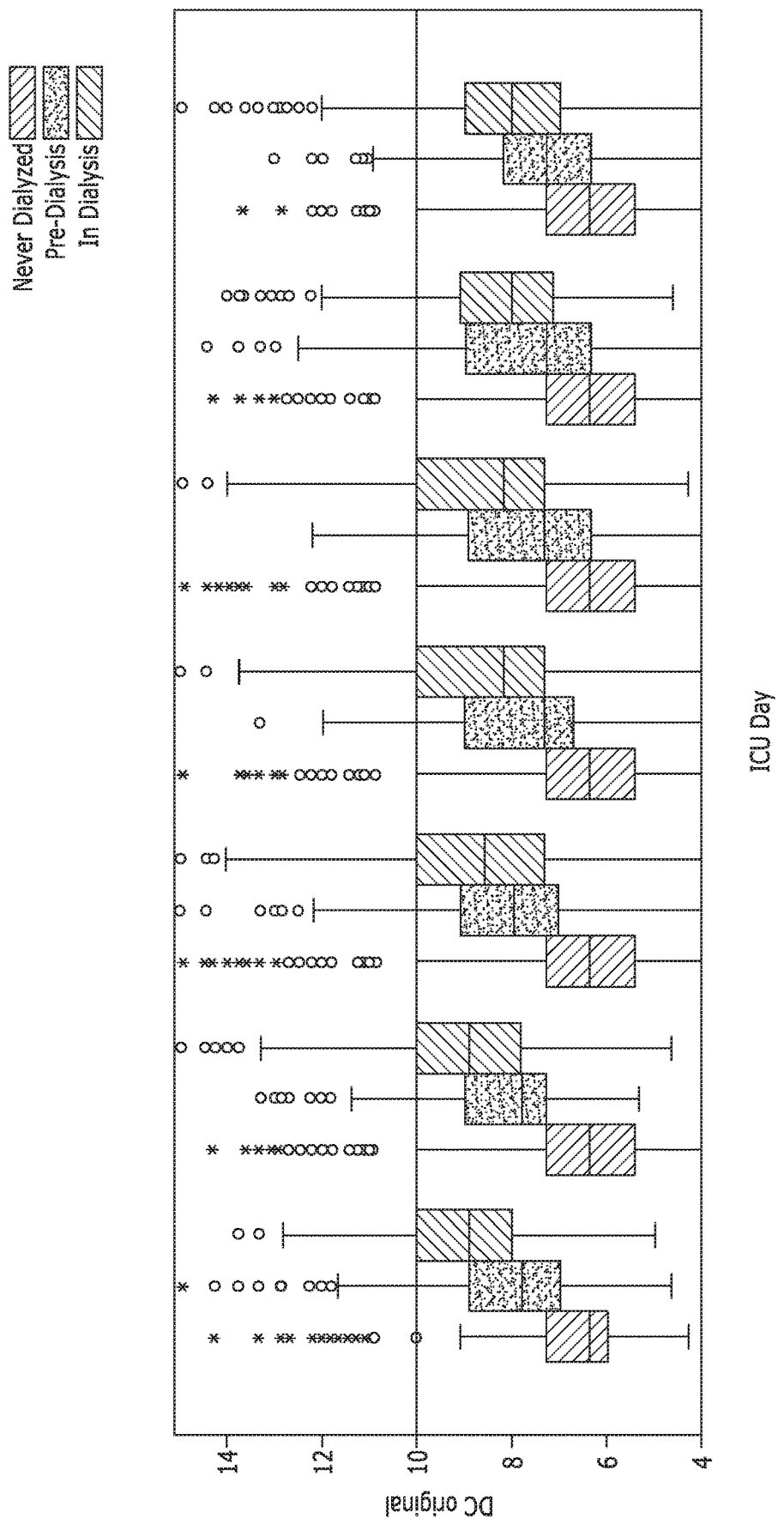
FIG. 22 illustrates progression of D/C in dialysis, not in dialysis and never-dialyzed patients during first 7 days of ICU stay (Cohort 4).

The maximum D/C ratio during ICU stay was significantly different between dialyzed and non-dialyzed patients (non-dialyzed D/C ratio 1.3 IQR (1.1-1.4) and dialyzed 2.0 IQR (1.6-2.5), p<0.01) (FIG. 21, Cohort 3; FIG. 22, Cohort 4).

Figure 23:
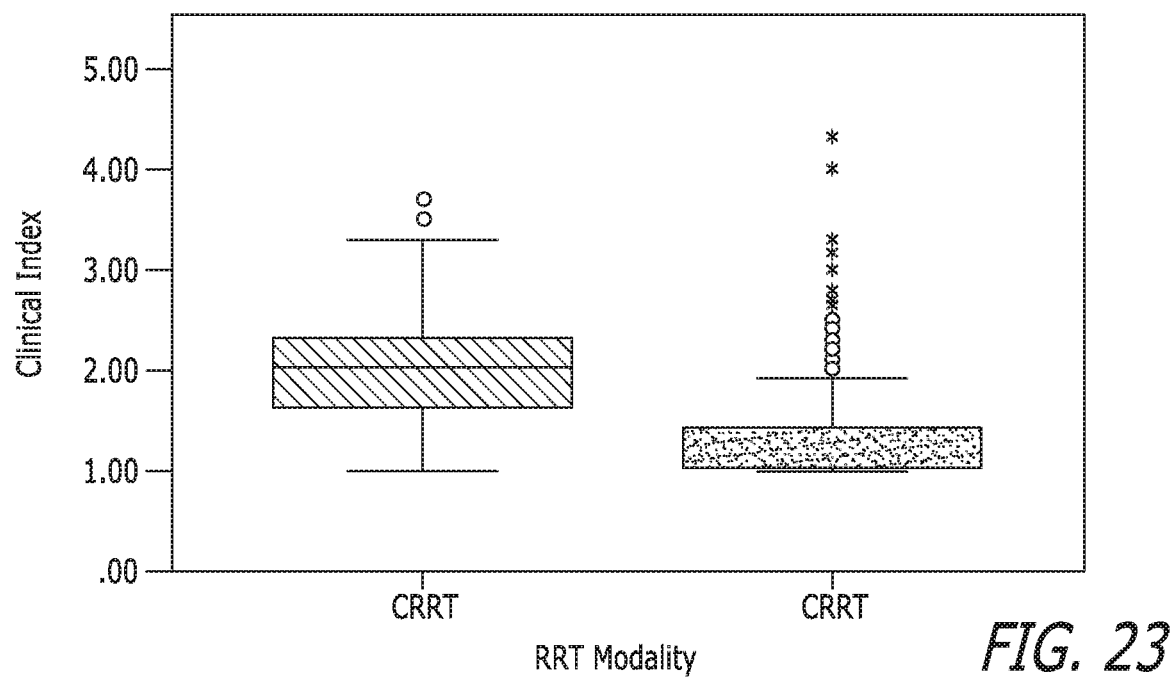
FIG. 23 illustrates clinical index at days patients were submitted to RRT by modality (Cohort 2).
Figure 24:
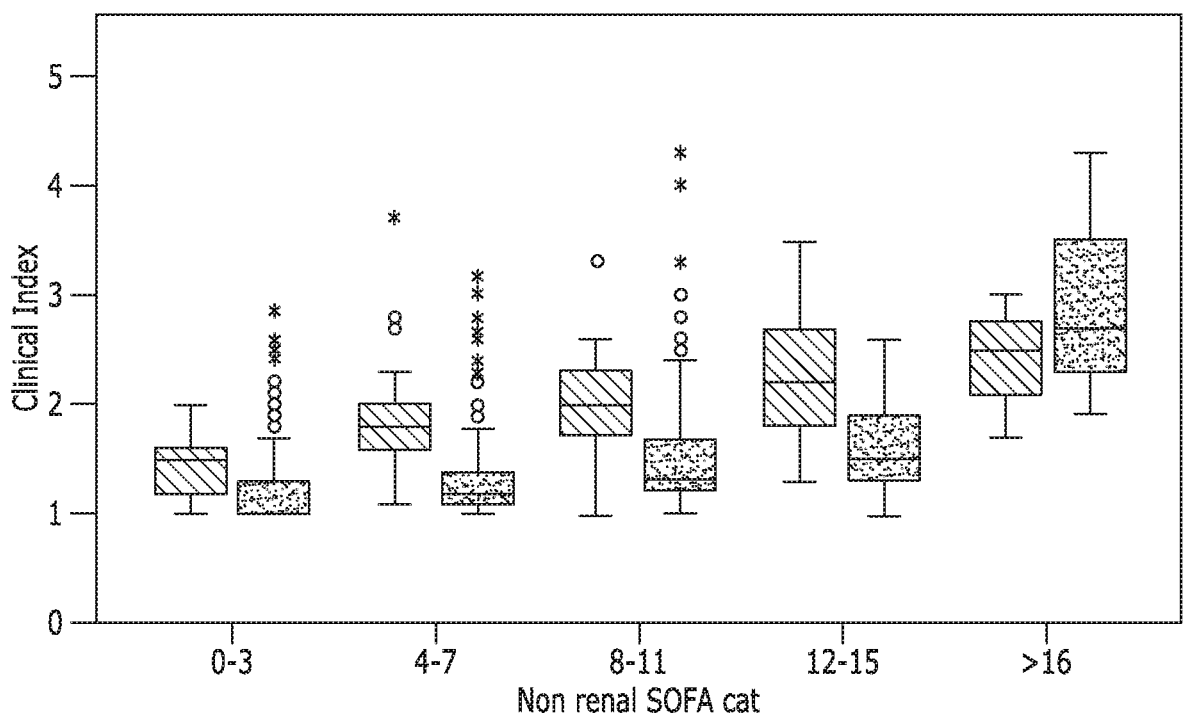
FIG. 24 illustrates D/C ratio at day patients started CRRT and IHD by quintiles of non-renal SOFA score.
Figure 25A:
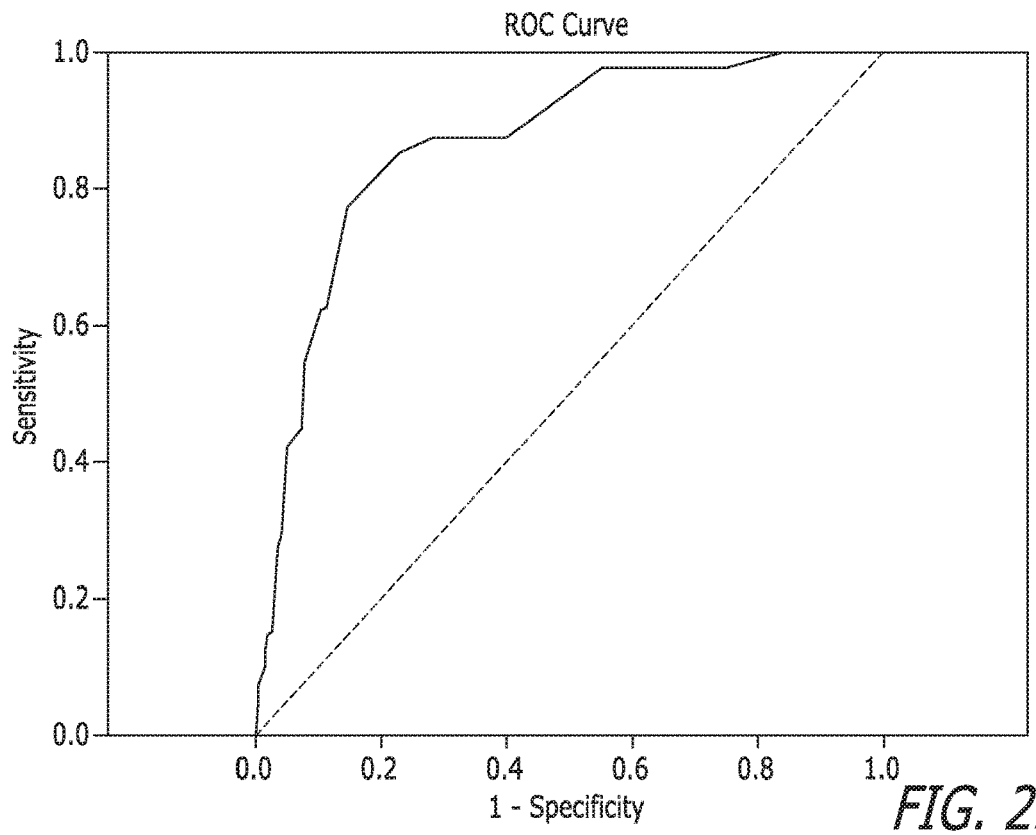
FIGS. 25A-B illustrate ROC for D/C ratio predicting dialysis in North America (FIG. 23A) and in all regions (FIG. 23B). North America AUC 0.864—CI (0.803-0.924). All regions: AUC 0.777—CI (0.717-0.838).
Figure 25B:
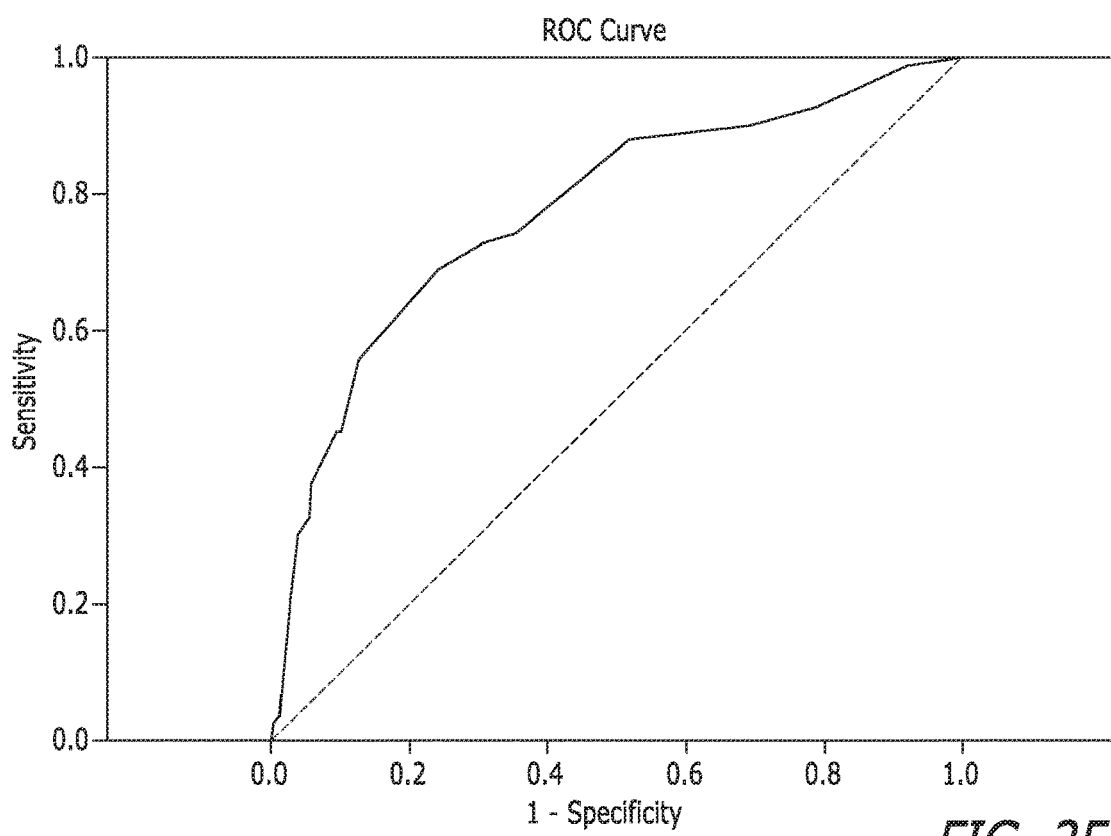
Figure 26:
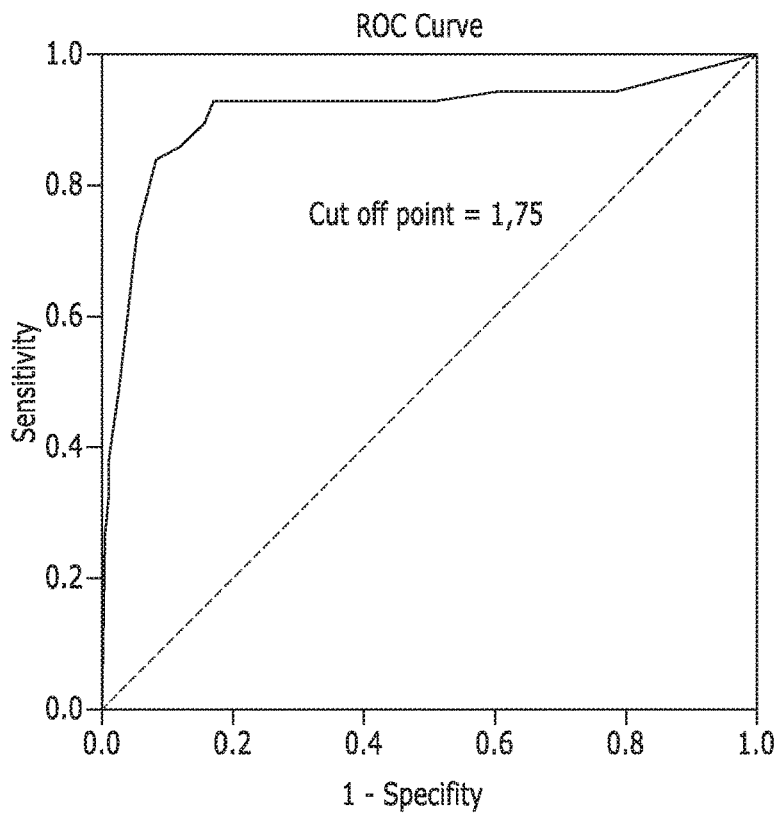
FIG. 26 illustrates ROC to predict dialysis D/C ratio max during 7 days of ICU for all patients. Legend area under the ROC curve 0.907—CI (0.852-0.963).
Figure 27:
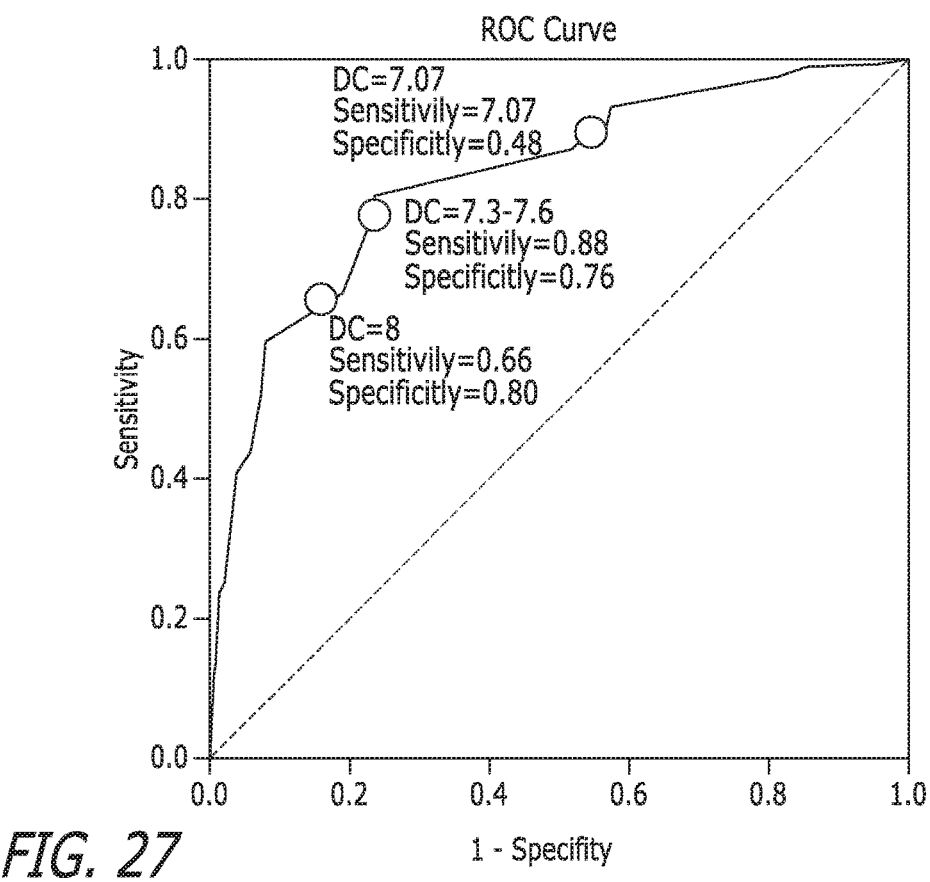
FIG. 27 ROC to predict dialysis D/C max during 7 days of ICU for Cohort 4.
Figure 28:
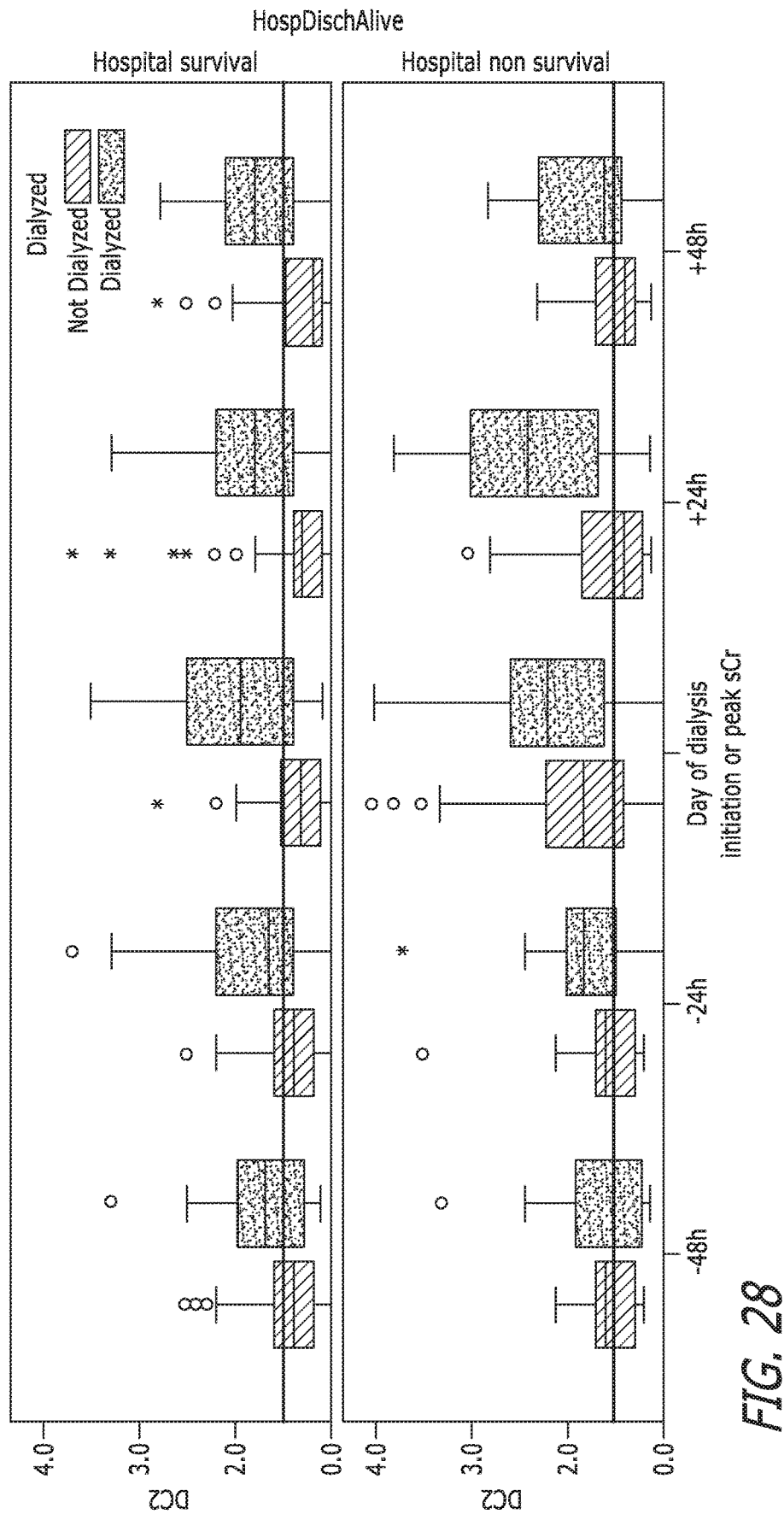
FIG. 28 illustrates progression of D/C ratio in survivors and non-survivors in all centers (Cohort 2).
Figure 29:
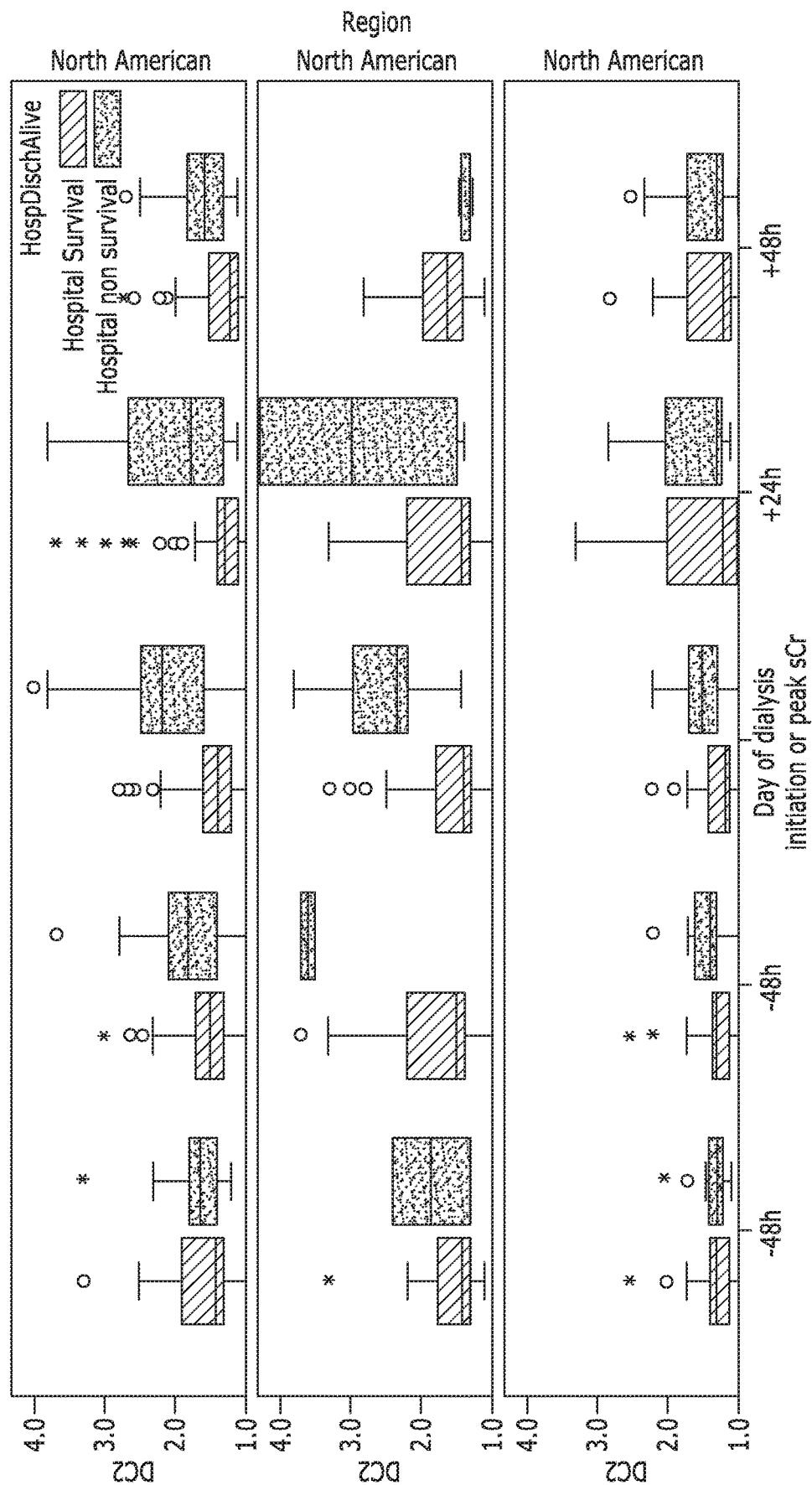
FIG. 29 illustrates progression of D/C ratio in survivors and non-survivors by region (Cohort 2).
Figure 30:
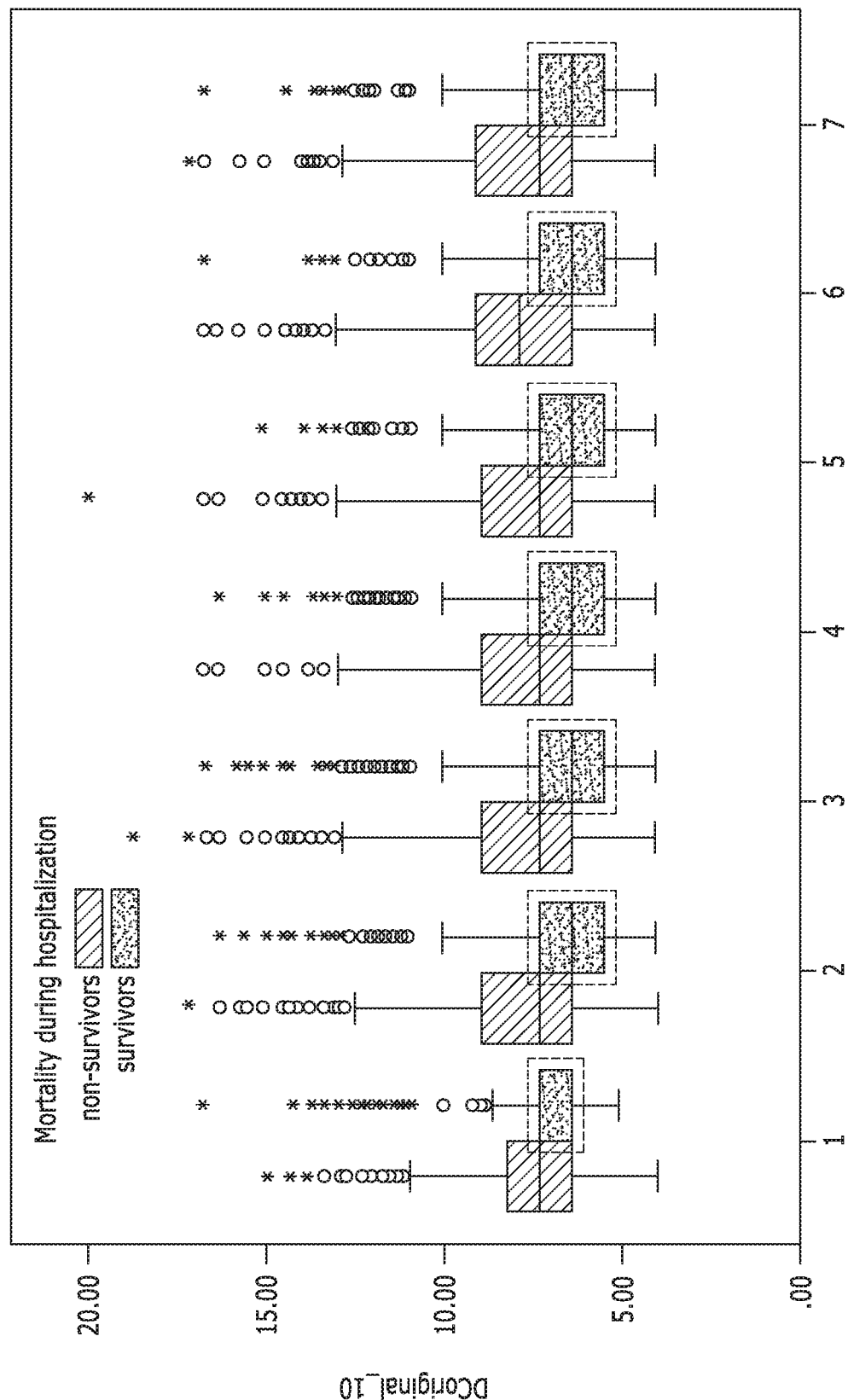
FIG. 30 illustrates progression of D/C ratio in survivors and non-survivors by ICU admission day (Cohort 4).
Figure 31:
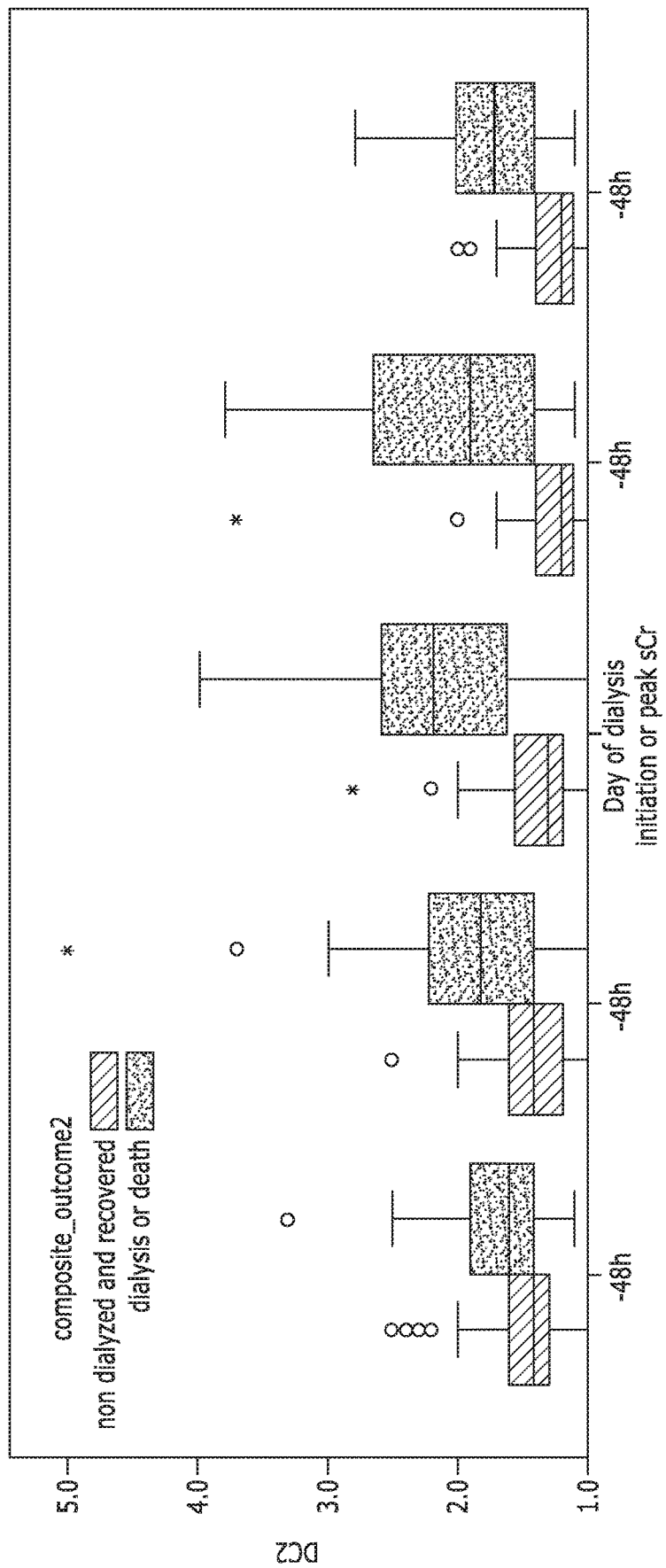
FIG. 31 illustrates changes in D/C ratio predict composite outcome of dialysis or death.

There was a significant difference of D/C ratio for different modalities at RRT initiation. Intermittent modalities tended to be started in less severely ill patients. The D/C ratio was significantly higher in days patients were submitted to CRRT procedures; CI CRRT days 2.00 IQR (1.6-2.3) vs IHD days 1.1 IQR (1-1.4); p<0.01 (FIG. 24, Cohort 3). The difference persisted across patients within different categories of non-renal SOFA. The D/C ratio was significantly higher between patients submitted to CRRT vs intermittent modalities within non renal SOFA of 4-11 (FIG. 23).

The D/C Ratio Reliably Predicts the Need for Dialysis

We evaluated the performance of two different calculations of the D/C ratio to predict the need of dialysis at day of peak sCr. The discriminative ability of the ratios were evaluated by calculating the area under the receiver operating characteristic (ROC) curve. Table 10 and FIGS. 25A-B, 26, and 27 show the performance of the D/C Ratio at different time points prior to dialysis initiation in different regions and in North America. Utilizing the Maximum value of the D/C ratio over 7 days of ICU admission the AUC for predicting dialysis improved considerably to 0.907—CI (0.852-0.963).

TABLE 10

Area under the ROC curve for the D/C ratio predicting dialysis need by Region.

| | North America | | Asia | | South America | | Total | |
|---|---|---|---|---|---|---|---|---|
| −48 h | 78 | .643 | 29 | .712 | 26 | .528 | 133 | .605 |
| −24 h | 132 | .788 | 43 | .513 | 40 | .674 | 215 | .666 |
| day of dialysis initiation | 240 | .864 | 68 | .697 | 73 | .730 | 381 | .777 |
| +24 h | 196 | | 50 | | 56 | | 302 | |
| +48 h | 159 | | 49 | | 50 | | 258 | |

D/C Ratio Changes are Associated with Mortality and can be Utilized to Predict Outcomes Progressive changes in the D/C ratio correlated with hospital mortality and composite outcomes of dialysis or death (FIGS. 28, 29, 30, and 31). Patients who did not need dialysis and survived had a progressive reduction in the D/C ratio whereas those who required dialysis or died had an increasing ratio.

Figure 32:
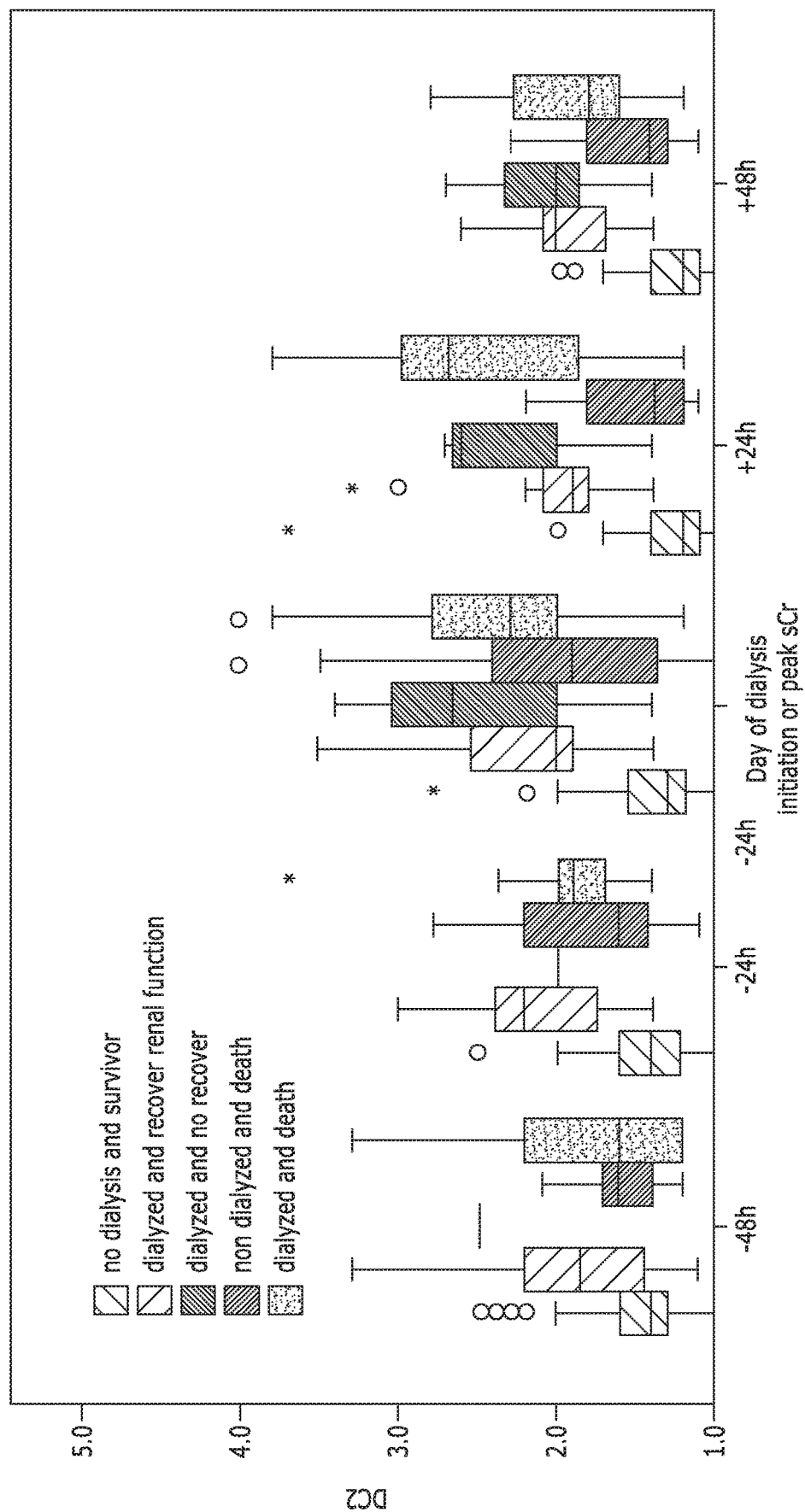
FIG. 32 illustrates changes in D/C ratio in patients based on renal functional recovery.

We further assessed the utility of the D/C ratio in distinguishing patients who recover kidney function. As shown in FIG. 32, patients who were dialyzed and died had the highest D/C ratios, followed by those who were dialyzed and recovered. Non-dialyzed patients with recovery had the lowest ratios whereas those who were not dialyzed and died had D/C ratios that were also elevated. Dialyzed patients who recovered had an improvement in their D/C ratios within 48 hrs of starting dialysis. These data show that both the magnitude and trends in the ratio can be utilized to guide management and inform prognosis. This would be helpful in determining not only when to initiate therapy but to inform decisions for transitions in therapy modality, changes in dose, stopping therapy for efficacy or futility.

Gradations of Demand Capacity Mismatch can Predict Response to Intervention

Figure 33:
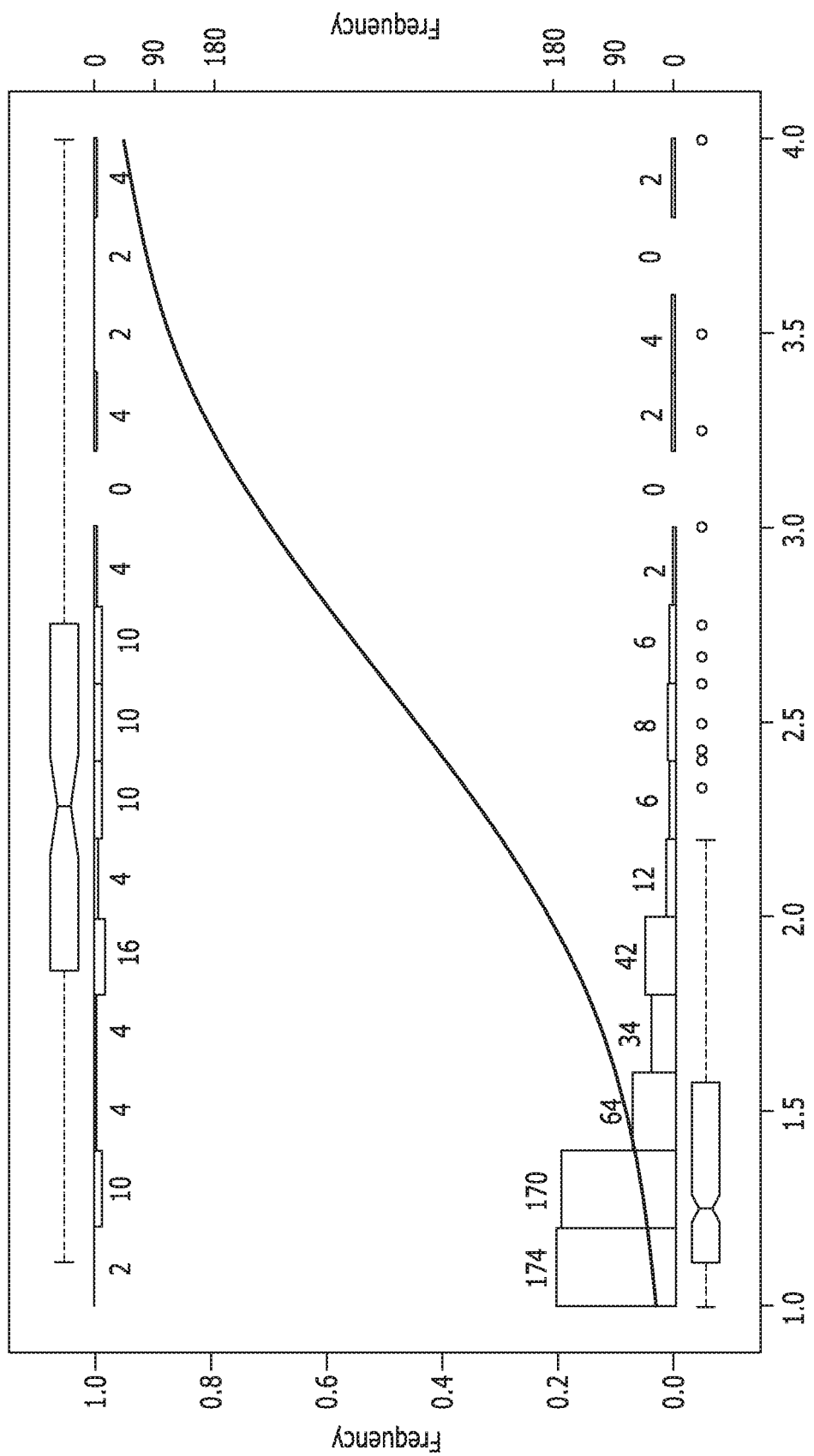
FIG. 33 illustrates distribution of D/C ratios in dialyzed and non-dialyzed patients on day of dialysis or peak serum creatinine can delineate threshold levels for dialysis need and adverse outcomes.

To enable the utilization of the D/C ratio for clinical care it is necessary to demonstrate that gradations of the ratio reflect outcomes. This can be achieved by establishing thresholds for the score for a floor and ceiling and demonstrating the association of these thresholds with clinical outcomes.
Floor: Score level below which dialysis is infrequent
Ceiling: Score above which dialysis is inevitable
Outcomes: Mortality, Renal recovery, Composite of survival and recovery vs. death or dialysis Additionally dynamic measurements of the ratio should support the thresholds for intervention. In essence, the gradations facilitate the application of the ratio for individualized management as dynamic changes can guide decisions for intervention and changes in therapy based on the patient's response. As shown in FIG. 33 we plotted the distribution of the D/C ratios in non-dialyzed vs dialyzed patients on day of dialysis (for dialyzed patients) and peak creatinine for non-dialyzed patients. A logistic regression was performed to predict the probability of dialysis need and is shown in the red line. The boxplot of score values in dialyzed and non-dialyzed patients is shown at the top and bottom of the graph. The numbers of patients are shown over each bar of the histogram. The data demonstrates that high dialysis probabilities are only found at the high score values and cut offs for the threshold can thus be established for the floor and ceiling.

Figure 34:
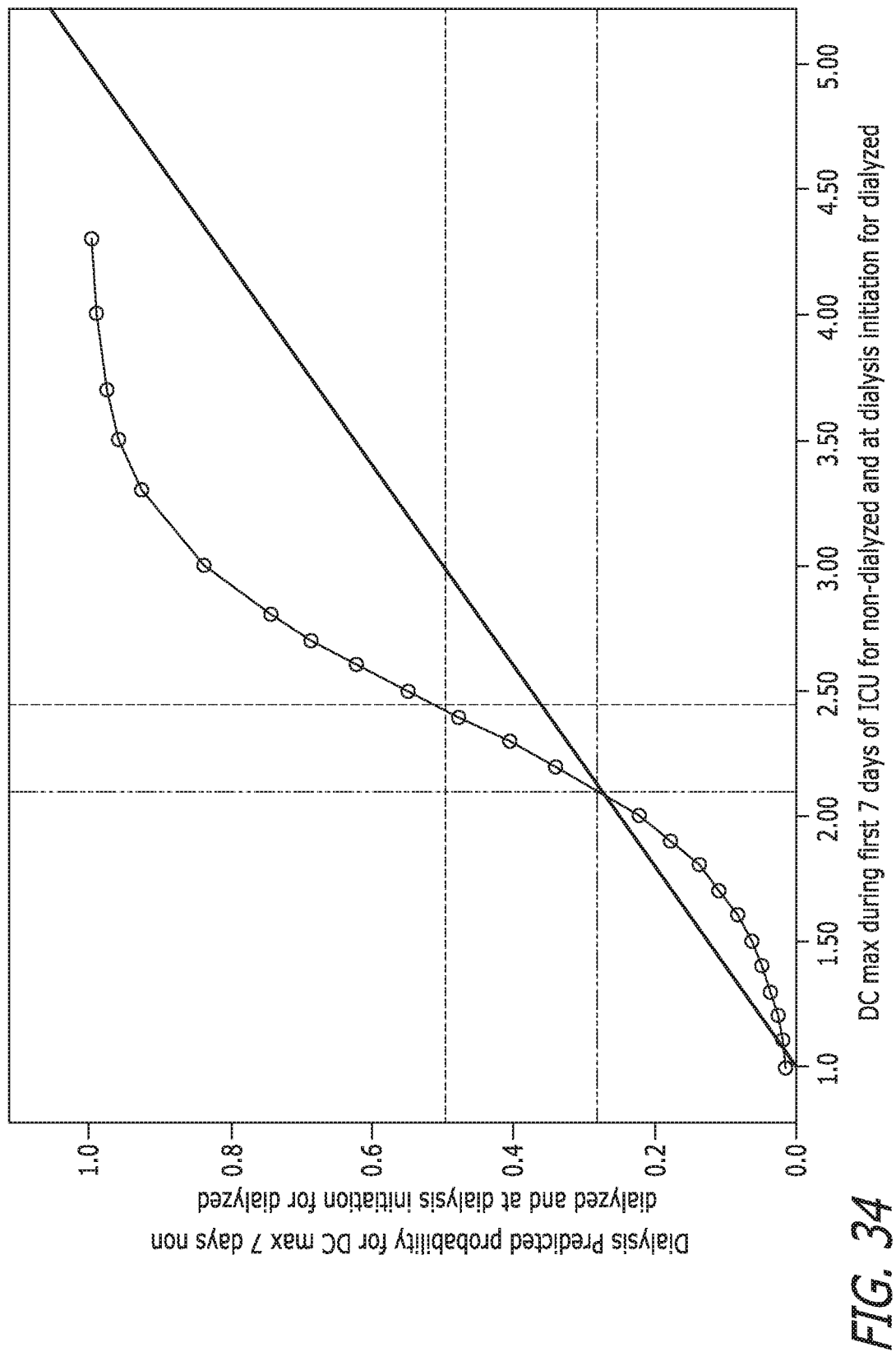
FIG. 34 illustrates dialysis predication need based on logistic regression (Cohort 3.

The distribution of D/C ratios can also be correlated with the composite outcomes of death, dialysis need and recovery of kidney function. As shown in FIG. 34, patients who were not dialyzed and recovered renal function had D/c ratios that were in the less than 2 and dialyzed patients had ratios>2. The x axis plots the ratios and the Y axis the percent of patients based on the composite outcomes of dialysis or death and non-dialysis and recovery.

Based on these data we can determine hinge points in D/C ratio score that correlate with outcomes to establish
   a. Lower boundary below which high likelihood of survival and recovery without dialysis
   b. Upper boundary above which high likelihood of death with or without dialysis or non-recovery
      1. <1.5 no dialysis and recovery
      2. 1.5-1.8 dialysis and recovery
      3. >1.9 no dialysis and death
      4. 2.0-2.5 dialysis and non-recovery
      5. >2.5 dialysis and death Does the D/C Ratio Correlate with Physician Decisions for Initiating Dialysis?

Figure 35:
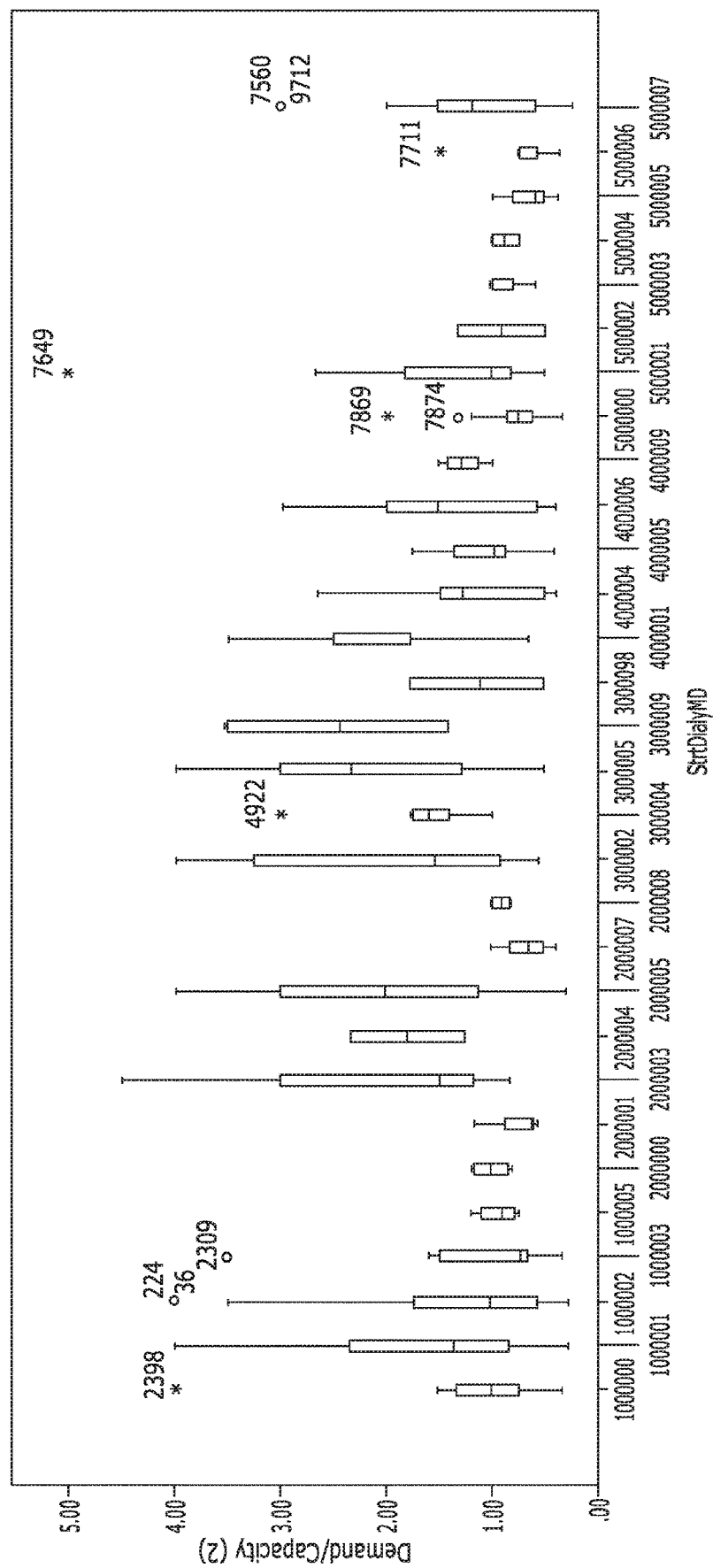
FIG. 35 illustrates the range of D/C ratios for individual physicians to initiate dialysis in ICU patients (Cohort 1).
Figure 36:
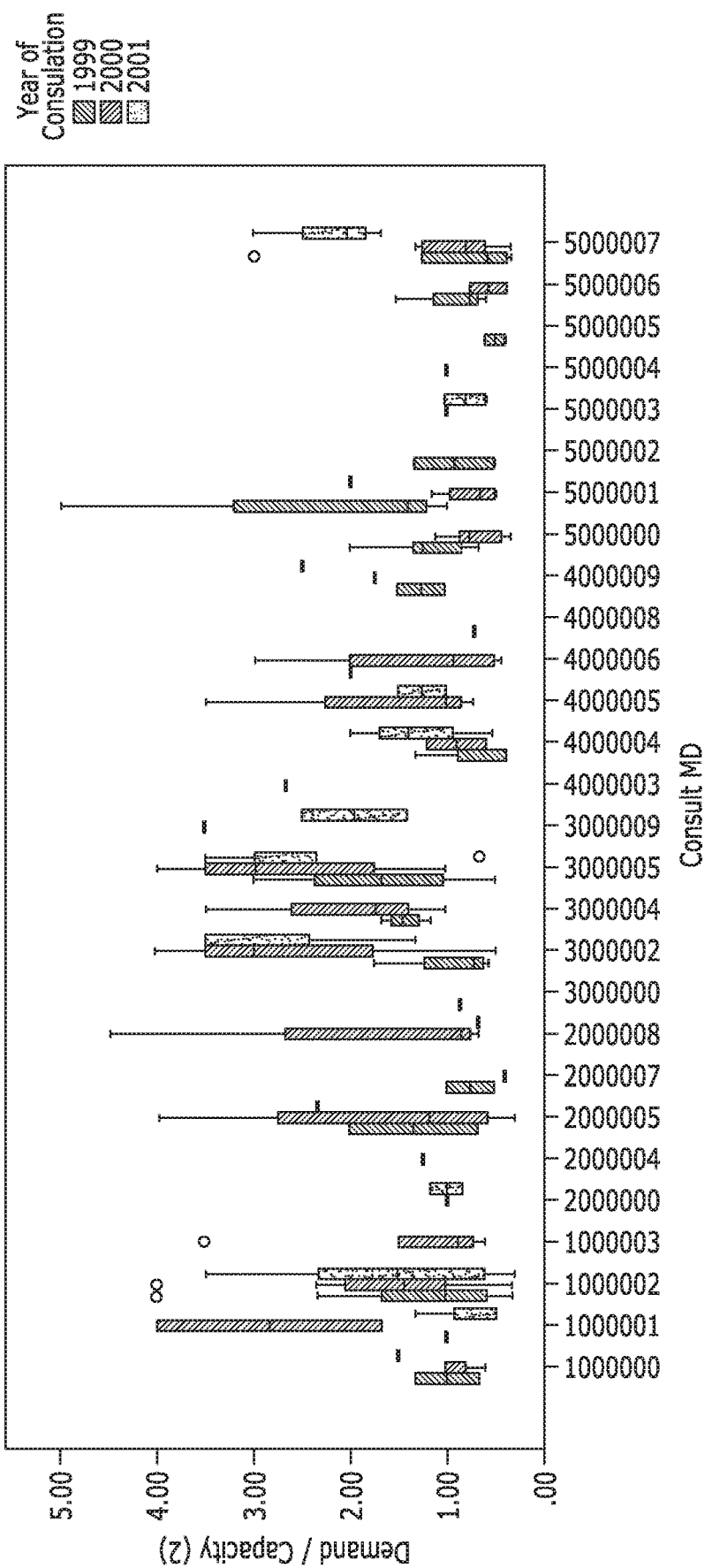
FIG. 36 illustrates D/C ratios at dialysis initiation by consult MD by year of consultation (Cohort 1).

In the PICARD study (Cohort 1), we tracked individual physician decisions over the years of the study. On analysis of this data we correlated the modality choice and time to start dialysis with the D/C ratio for individual physicians and saw how these changed over the years of the study. As shown in tracked individual physician decisions over the years of the study. On analysis of this data we correlated the modality choice and time to start dialysis with the D/C ratio for individual physicians and saw how these changed over the years of the study. As shown in FIG. 35 individual physicians have a wide range of D/C ratios for initiating dialysis and these variations persist over the different years of the study (FIG. 36).

Figure 37:
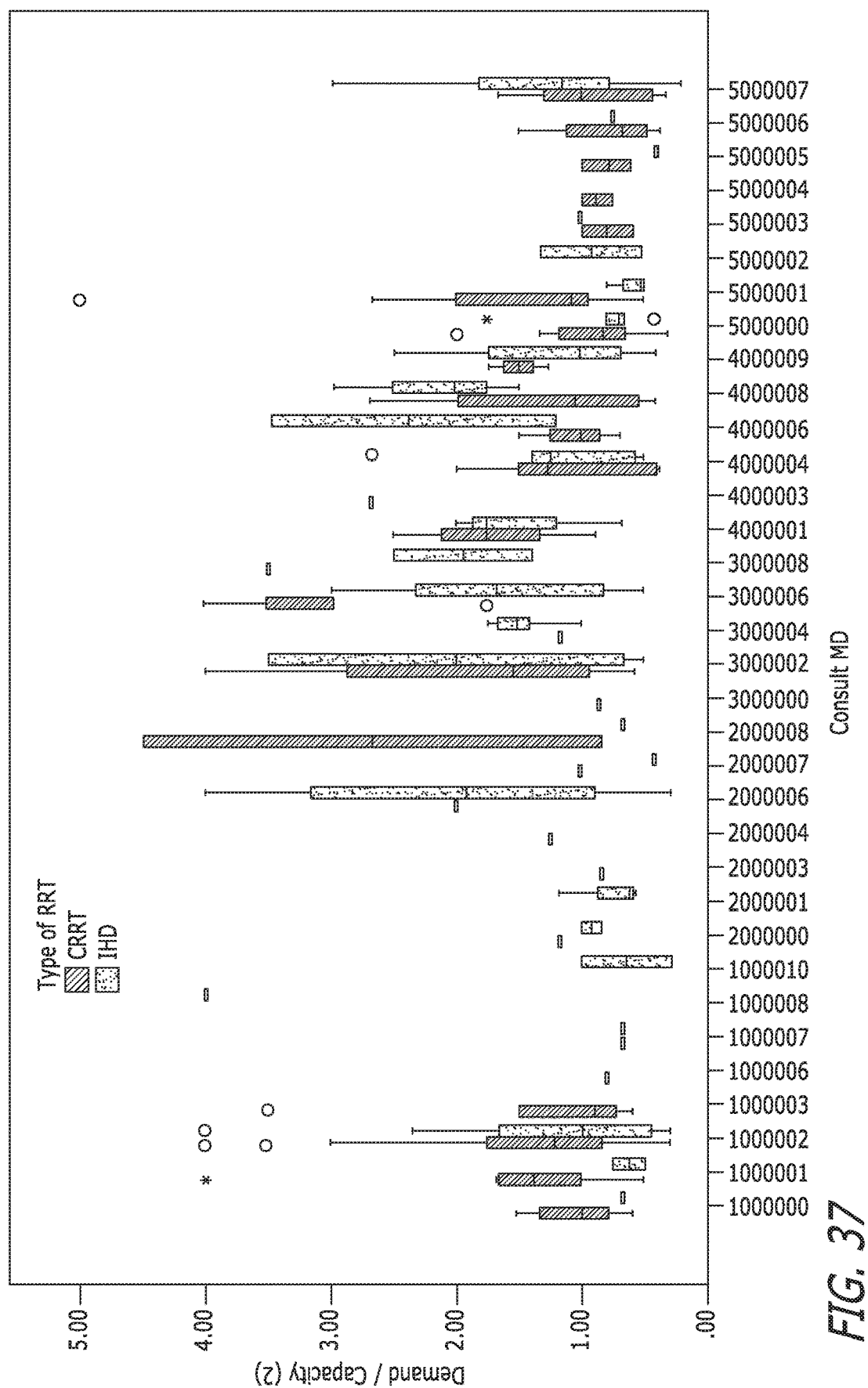
FIG. 37 illustrates a box plot representation of D/C ratio for each physician starting RRT by modality (Cohort 1). Legend: CRRT: Continuous Renal Replacement Therapy; IHD: Intermitent Hemodialysis.

The patterns for initiating RRT and modality choice were also over a wide range of D/C ratios in individual patients and varied across centers over 3 years (FIG. 37).

We further tested the concept that there is wide variability in when to initiate RRT by surveying clinicians utilizing real cases from our registry (Cohort 2) to assess their decision making. We presented 22 cases derived from the 5 centers to nephrologists and intensivists at the 5 centers using survey monkey. The clinical presentation included all pertinent data to peak creatinine in the non-dialyzed (n=10) and the day of dialysis in dialyzed (n=12) patients. The scenarios included the data to calculate the D/C ratio without giving the ratio. 12-28 physicians responded to each case for a total of 332 responses. MDs preferred to initiate dialysis immediately in 40%, reevaluate after some time in 29%, did not think the patient needed dialysis in 26% and considered the patient futile in 5%.

Figure 38A:
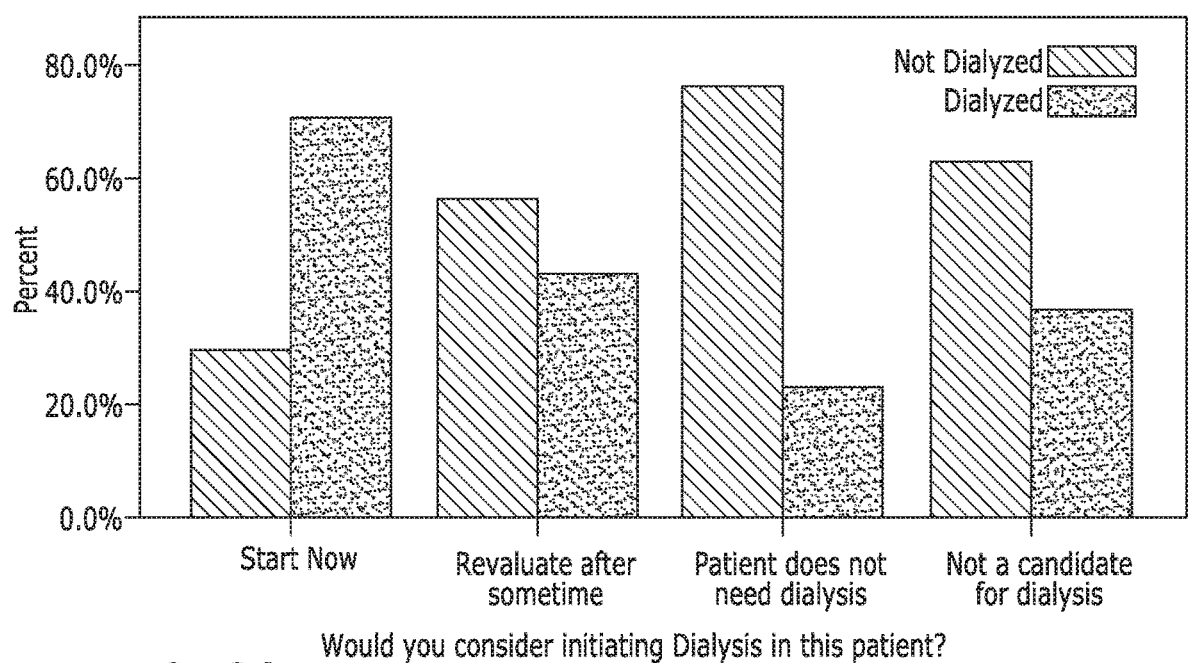
FIG. 38A illustrates physician choices and actual events and 38B illustrates a relationship of D/C ratio to physician choices
Figure 38B:
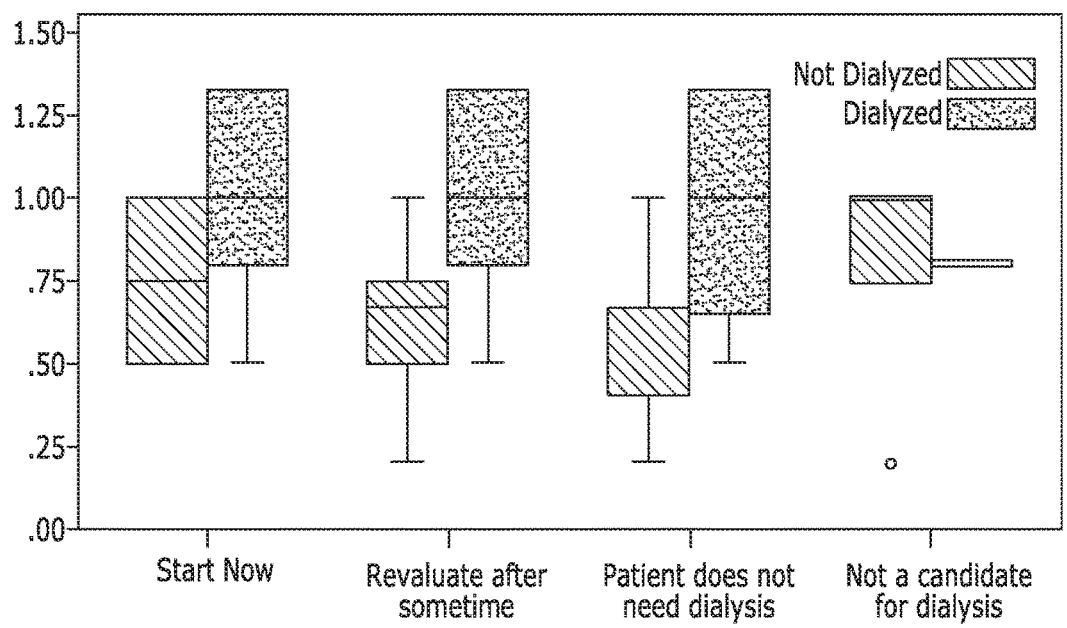

FIG. 38A shows there was substantial discordance between the physicians responses and the actual events in ⅓ of the 332 reviews, 30% on cases not receiving dialysis when there was a preference to start immediately and 20% receiving dialysis when it was felt that it was not required. Even when dialysis was not considered to be beneficial, 37% of the patients received dialysis. In the 12 cases where there were over 20 reviews each we found the 6 dialyzed mean D/C ratio=0.96 and for 6 non-dialyzed the mean ratio 0.59 (p=0.06). In dialyzed patients, the D/C ratio ranges were similar and high irrespective of the physician choices, whereas in non-dialyzed patients lower D/C ratios correlated with the decision that the patient did not need dialysis (FIG. 38B). This supports face validity that the ratio is predictive of RRT and the two middle groups show similar RRTs despite the clinical decision to wait.

For each case we also evaluated reasons for initiating dialysis and determined additional logistic factors that influence the decision. The top factors were nurse availability (27%), vascular access issues (25%), dialysis need at night (17%) and holiday and weekends (17%). Clinician's perception of futility also correlate well with their choice of withholding dialysis and a prediction that the patient would recover renal function completely was associated with a greater likelihood of considering that the patient did not need dialysis. The choice of initial modality also appears to be related to the underlying D/C ratio and logistic factors.

Summary of Data

In some embodiments, the devices, systems, and methods described can determine a D/C ratio that represents an imbalance between renal function and a patient's demand.

In some embodiments, the devices, systems, and methods described can calculate D/C ratio scores in multiple ways (D/C ratio, D/C logistic (summative score), sum ratio, multiplicative ratio) predict dialysis need and outcomes with AUC 0.83-0.87

In some embodiments, the D/C ratio is a dynamic parameter that progressively increases in AKI patients who need RRT and correlates with dialysis need, mortality and composite outcome adverse outcomes.

In some embodiments, the devices, systems, and methods described can assess, calculate, and/or determine hinge points in D/C ratio scores that correlate with outcomes to establish a lower boundary below which high likelihood of survival and recovery without dialysis, an upper boundary above which high likelihood of death with or without dialysis or non-recovery, or both.

In some embodiments, the devices, systems, and methods described can discriminate well regarding modality choice as patients selected for CRRT have significantly higher CI across the four lower quintiles of non-renal SOFA score.

In some embodiments, the devices, systems, and methods described can assist a physician's decisions for initiating dialysis. These decisions can be influenced by a combination of clinical factors, perceived severity of illness, likelihood of benefit, and logistic factors. The D/C ratio can discriminate well and may reduce uncertainty by a quantitative assessment of clinical and process of care factors that influence the decision.

In some embodiments, sequential assessment of CI allows evaluation of timing of RRT initiation using patient's characteristics as a parameter.

In some embodiments, the devices, systems, and methods described can use a D/C ratio to compare center and physician patterns regarding RRT initiation and modality choice.

In some embodiments, the devices, systems, and methods described can calculate D/C ratio scores based on simple clinical parameters that are routinely assessed in ICU. In some embodiments, these simple clinical parameters can be incorporated in EMR for an alert system and combined with a risk score for identifying high risk for AKI.

In some embodiments, the demand capacity imbalance quantification can be used for informing timing of intervention, adjustments in dose of dialysis, transitions in therapy modality, and/or stopping dialysis for efficacy and futility.

Example 2

A 73 yr old is transferred from a community hospital where he had been admitted 1 week earlier with a 3 day h/o cough, shortness of breath, and fever. At the community hospital he has right lower lobe pneumonia and is placed on antibiotics, but he fails to improve and requires intubation. During his hospital course, he improves initially and is extubated after 2 days. However, he deteriorates again with abdominal distension, fever, increasing acidosis and hypotension. The patient requires reintubation and $FiO_2$ of 70%. Urine output decreases to 500 mL/day despite diuretics every 12 hours, blood urea nitrogen (BUN) increases from baseline of 20 to 60 and creatinine from baseline 1.0 to 1.9. The patient is 10 liters positive on his cumulative fluid balance.

The patient has a past medical history of hypertension, but stopped chronic smoking 10 yrs prior. An exam reveals: wt 175 lbs (baseline 150 lbs) thin built, paralyzed heart rate (HR) 100/min, blood pressure (BP) 110/70 on dopamine 3 ug/kg/min, temperature 99 F, lungs bilateral wheezes and occasional rales, cardiovascular system heart sounds heard, abdomen distended and sluggish bowel sounds, extremities warm, trace edema. Labs reveal: White blood cell (WBC) 37.7, 70% bands, hematocrit (HCT) 30, platelets 125,000, Na 137, K 4.8, bicarb 10, anion gap 20, pH 7.27, BUN 85, creatinine 2.8, urinalysis (UA) dark, blood+, muddy granular and hyaline casts, renal tubular epithelial (RTE) cells, sputum yeast. The patient is maintained on antibiotics: Vanco, Ceftazidime, Flagyl, and amphoteracin.

The patient's clinical diagnosis is that he is a 76 yr old man with non-oliguric acute renal failure (ARF) related to pneumonia, respiratory failure, sepsis and acidemia.

At his initial evaluation after transfer his demand score is high driven by a large cumulative fluid balance of 10 L, a catabolic state from his sepsis and a high organ failure score (lung, heart, coagulation and central nervous system (CNS)) while his kidney capacity is low as he has a low urine output and his creatinine is high. His D/C ratio is computed as 1.6. On day 2 he deteriorates further and requires a higher dose of vasopressors for his blood pressure and he stops making urine. His D/C ratio is further increased to 2.2 and he is started on continuous renal replacement therapy (CRRT). The dialysis parameters are adjusted to remove fluid and correct his acidosis and provide him nutrition support to correct his catabolic state. Over the next 3 days he stabilizes with improvement in respiratory parameters and his oxygen requirements on the ventilator decrease to $FiO_2$ 40%. His fluid balance corrects with fluid removal on the dialysis, his sepsis came under control with antibiotics, and he does not need any further vasopressors for his blood pressure. His D/C ratio improves and by day 5 is down to 1.5 when he is extubated. He starts making urine. By day 8 he is able to stop dialysis as he recovers renal function and his D/C ratio on Day 6 and over the next 3 days his kidney function improved and he was taken off dialysis. His D/C ratio progressively improves and on his discharge day (day 10), his D/C ratio is down to 1.12.

This case illustrates how the D/C ratio can integrate all the pertinent data in a dynamic manner to provide guidance to initiate and stop dialysis. At the initial evaluation his D/C ratio is in the target range, for initiating dialysis and as he progresses, the improvement in the ratio is helpful in guiding discontinuation of therapy. Additionally, knowledge of the components contributing to the increased demand (fluid and catabolic status) can be targeted specifically by adjusting the operational parameters of the dialysis therapy and permit nutritional support.

Example 3

A 56 yr old man is admitted to the chronic care unit (CCU) with increasing shortness of breath, weight gain, edema and increasing abdominal girth. He has a decrease in urine output for 3-4 days and an increase in BUN and creatinine despite diuretics. His is known to have CHF for 5 yrs and is on Digoxin/Diuretics. He has cardiac catheterization and normal coronary arteries. He is admitted 6 weeks previously for worsening congestive heart failure (CHF), started on ACE inhibitors and hydrallazine/nitrates. His last creatinine 2 weeks prior to admission is at baseline 1.2-1.3 mg/dL.

The patient has a past medical history of being a paraplegic from a boating accident, atonic bladder, Insulin-Dependent Diabetes Mellitus (IDDM) for 30 yrs, familial polyposis S/P colectomy, gout, and is a chronic smoker.

An exam reveals: he is a short obese man, wt 110 kg (baseline 95-98 kg), HR 98, BP 121/72, jugular venous pressure (JVD) to ear lobe, carotids normal upstroke. Lung fields dull to mid lungs, B/L rales, point of maximal impulse (PMI) displaced, S3+Loud P2, murmurs of tricuspid regurgitation (TR), mitral regurgitation (MR); abdomen large protuberant free fluid, extremities 4+ edema, $O_2$ sat 90% on 4 L nasal cannula.

Labs reveal: WBC 13.3, Hct 36.2, Na 138, K 3.6, HCO3 37, Creatinine 1.9 mg/dl, BUN 98 mg/dl, liver function test (LFT) normal, Albumin 3.8, UA Trace protein 0-2 WBC, no casts.

The patient's clinical diagnosis is that he has acute decompensated heart failure with worsening renal function.

Initially, the patient's heart is the predominant organ requiring support. Based on the calculations of demand capacity for cardiac function his ratio is 1.5. On Day 2, despite aggressive diuretic and ionotropic regimens his heart failure continues to worsen and his D/C ratio is 2. At this point he is placed on an intraortic balloon pump to support him, while a ventricular assist device is considered as a bridge to heart transplant. On day 3, his urine output drops further and as his kidney capacity is markedly reduced. The increased demand capacity mismatch results in a D/C ratio of 2.3. At this point, dialysis is initiated to help support both his kidney and heart function. Over the next 2 days, he is placed on a ventricular assist device and his heart failure is controlled. His D/C ratio improves to 1.8. As dialysis proceeds, by day 5 his D/C ratio is 1.5, he is making more urine, and he can be taken off dialysis. Two weeks later, he receives a heart transplant and progressively improves. He goes home at 5 weeks.

For the purposes of explanation, specific are details set forth herein in order to provide a thorough understanding thereof. However, it will be apparent that the description may be practiced without these specific details. Some embodiments may be depicted using block diagram(s) or simplified form in order to avoid unnecessary obscuring of the description.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A method of treating a patient, the method comprising:
obtaining, in a processor, a plurality of measurements comprising demand parameters and capacity parameters that are related to a plurality of organs of the patient;
determining, via the processor, (i) an organ demand score for each of the plurality of organs based on demand parameters that reflect the demand placed by each organ on the remaining organs and (ii) an organ capacity score specific to each of the plurality of organs based on capacity parameters comprising functional elements required for homeostasis of each organ;
identifying an organ at risk of failure from the plurality of organs based on a mismatch between the organ demand score for the organ at risk and the organ capacity score for the organ at risk by calculating, via the processor, a demand-capacity probability score;
causing, via the processor, information to be displayed on a display screen that is indicative that the patient has organ failure and needs intervention when the demand-capacity probability score of the organ at risk is in a target range; and
providing for, via the processor, an administration of organ support to the organ at risk in the patient.

2. The method of claim 1, wherein the calculating is performed by dividing the organ demand score by the organ capacity score to provide the demand-capacity probability score.

3. The method of claim 1, wherein at least the obtaining, determining, and identifying steps can be repeated to provide a dynamic demand-capacity probability score.

4. The method of claim 3, wherein the steps are repeated at intervals of time.

5. The method of claim 3, wherein the dynamic demand-capacity probability score can be used to determine a change in therapy needed.

6. The method of claim 1, wherein the plurality of measurements includes at least one of a heart rate, a blood pressure, a cardiac output, a urine sample, a blood sample, a liquid input value, a liquid output value, a sequential organ failure assessment score for the patient, an INR value, a $pO_2$ value, a $CO_2$ removal value, a FeV1 test value, a pH value or a combination thereof.

7. The method of claim 6, wherein the blood sample is used to determine blood pH, bilirubin levels, albumin levels, or a combination thereof.

8. The method of claim 6, wherein each of the urine sample, the blood sample, the liquid input value, the liquid output value, the heart rate, and the sequential organ failure assessment score has a result that is given as a score.

9. The method of claim 8, wherein the result is given as a score that is in a range of 0 to 100.

10. The method of claim 1, wherein the organ failure is heart failure, lung failure, kidney failure, liver failure, brain failure, or a combination thereof.

11. The method of claim 1, wherein the organ support is a molecular adsorbents recirculating system (MARS), cell based liver support, a balloon pump, a ventricular assist device (VAD), a heartmate, a ventilator, an ECMO, an ECCOR, dialysis, or a combination thereof.

12. The method of claim 1, further including:
Determining, via the processor, the patient does not need intervention when the demand-capacity probability score is in a low range; and
determining, via the processor, the patient has organ failure and intervention is futile when the demand-capacity probability score is in a high range.

13. The method of claim 1, wherein:
the two or more organs comprises a kidney;
the plurality of measurements comprise a urine sample, a blood sample, a liquid input value, a liquid output value, and a sequential organ failure assessment score;
the organ demand scores comprise a kidney demand score;
the organ capacity scores comprise a kidney capacity score;
the organ at risk comprises a kidney; and
the administration of organ support is dialysis.

14. The method of claim 1, wherein the plurality of measurements include at least one of a patient temperature, a patient body weight, a blood pH, a serum sodium level, a phosphate level, a nitrogen balance, a protein catabolic rate, an energy requirement, a glucose level, a serum potassium level, a respiratory rate, an oxygenation level, a blood pressure, a heart rate, a vasopressor use, a urine volume, an estimated GFR level, a cumulative fluid balance, a hematocrit percentage, a WBC level, a platelet level, a bilirubin level, an INR level, or an albumin level.

15. The method of claim 1, wherein the organ demand further comprises one or more of a fluid score, an organ assessment score, and a solute score.

16. The method of claim 15, wherein the fluid score is calculated based on plasma and extracellular compartmental distribution, accumulated fluid volume, or a combination thereof.

17. The method of claim 15, wherein the solute score is calculated based on one or more of catabolic state, catabolic rate, and nitrogen balance.

18. The method of claim 1, wherein at least the obtaining, determining, and identifying steps can be repeated to measure a change in the organ demand scores and the organ capacity scores over time for the plurality of organs.

19. An apparatus that provides for a determination of organ intervention treatment for a patient, the apparatus comprising:
an interface configured to receive a plurality of measurements comprising demand and capacity parameters that are related to a plurality of organs of the patient; and
a processor communicatively coupled to the interface and configured to:
determine (i) an organ demand score for each of the plurality of organs based on demand parameters that reflect the demand placed by each organ on the remaining organs and (i) an organ capacity score for specific to each of the plurality of organs based on capacity parameters comprising functional elements required for homeostasis for each organ;
identify the probability an organ at risk of failure from the plurality of organs based on a mismatch between the organ demand score for the organ at risk and the organ capacity score for the organ at risk by calculating, via the processor, a demand-capacity probability score;
cause information to be displayed on a display screen indicative that the patient needs intervention based on the demand-capacity probability score; and cause an administration of organ support to the organ at risk in the patient when the demand-capacity probability score is in a target range or cause organ support to the organ at risk in the patient to be terminated when the demand-capacity score is above or below the target range.

20. The apparatus of claim 19, wherein the processor is configured to cause organ support to the patient to be adjusted when the demand-capacity probability score deviates from an initial value.

21. The apparatus of claim 19, wherein demand-capacity probability score is dynamic such that the processor determines a new value for the demand-capacity score after new measurements are received.

* * * * *